US008648045B2

(12) United States Patent
Shoshan-Barmatz et al.

(10) Patent No.: US 8,648,045 B2
(45) Date of Patent: Feb. 11, 2014

(54) VDAC1 COMPOSITIONS AND METHODS OF USE THEREOF FOR REGULATING APOPTOSIS

(75) Inventors: Varda Shoshan-Barmatz, Omer (IL); Salah Abu-Hamad, Shalom (IL); Laetitia Arzoine, Herzliya (IL); Hilal Zaid, Hamesholash (IL)

(73) Assignee: Ben Gurion University of the Negev Research and Development Authority Ltd., Beer Sheva (IL)

( * ) Notice: Subject to any disclaimer, the term of this patent is extended or adjusted under 35 U.S.C. 154(b) by 0 days.

(21) Appl. No.: 13/397,548

(22) Filed: Feb. 15, 2012

(65) Prior Publication Data

US 2012/0214741 A1      Aug. 23, 2012

Related U.S. Application Data

(63) Continuation-in-part of application No. 11/817,869, filed as application No. PCT/IL2006/000311 on Mar. 9, 2006, now Pat. No. 8,119,601.

(60) Provisional application No. 60/736,291, filed on Nov. 15, 2005, provisional application No. 60/659,876, filed on Mar. 10, 2005.

(51) Int. Cl.
  *C07K 14/435* (2006.01)
  *A61K 38/17* (2006.01)
  *C12N 15/00* (2006.01)
  *C12N 5/02* (2006.01)

(52) U.S. Cl.
  USPC ....... 514/18.9; 514/12.2; 514/19.2; 514/19.3; 435/320.1; 435/375; 530/324; 536/23.5

(58) Field of Classification Search
  None
  See application file for complete search history.

(56) References Cited

U.S. PATENT DOCUMENTS

| | | |
|---|---|---|
| 5,288,707 A | 2/1994 | Metternich |
| 5,391,377 A | 2/1995 | Barnwell |
| 5,550,251 A | 8/1996 | Hirschmann |
| 5,552,534 A | 9/1996 | Hirschmann |
| 5,780,235 A | 7/1998 | Bandman |
| 5,811,392 A | 9/1998 | Gilon |
| 5,910,478 A | 6/1999 | Hlavka |
| 5,965,539 A | 10/1999 | Sebti |
| 6,165,732 A | 12/2000 | Korsmeyer et al. |
| 6,291,247 B1 | 9/2001 | Riopelle |
| 2004/0096444 A1 | 5/2004 | Pizzo |
| 2005/0085420 A1 | 4/2005 | Korsmeyer |
| 2005/0234116 A1 | 10/2005 | Sugiyama |

FOREIGN PATENT DOCUMENTS

| | | |
|---|---|---|
| WO | 02/083712 | 10/2002 |
| WO | 03/031650 | 4/2003 |
| WO | 2004/016230 | 2/2004 |

OTHER PUBLICATIONS

Lazar et al Mol. Cell. Biol., vol. 8, pp. 1247-1252, 1988.*
Wells, 1990, Biochemistry 29:8509-8517.*
Shi et al, Biochemical and Biophysical Research Communications, 2003, vol. 305, pp. 989-996.*
Accession No. P45879 or Q3ZCK0 or Q71SW7, Nov. 1, 1995.*
Arizone et al, (Journal of Biological Chemistry, 2009, vol. 284, No. 6, pp. 3946-3955.*
Zaid et al, Cell Death and Differentiation, 2005, vol. 12, pp. 751-760.*
Arbel et al., (2010) Voltage-dependent anion channel 1-based peptides interact with Bcl-2 to prevent antiapoptotic activity. J Biol Chem 285(9): 6053-62.
Arzoine et al., (2009) Voltage-dependent anion channel 1-based peptides interact with hexokinase to prevent its anti-apoptotic activity. J Biol Chem 284(6): 3946-55.
Azoulay-Zohar, Heftsi et al., (2004) In self-defense: hexokinase promotes voltage-dependent anion channel closure and prevents mitochondria-mediated apoptotic cell death. Biochem. J. 377(pt 2):347-355.
Blachly-Dyson, Elisabeth et al., (1993) Cloning and functional expression in yeast of two human isoforms of the outer mitochondrial membrane channel, the voltage-dependent anion channel. J Biol Chem. 268(3):1835-41.
Cochran, Adrea et al., (2001) Tryptophan zippers: Stable, monomeric-hairpins. Proc Natl Acad Sci USA 98 (10):5578-5583.
Colombini, Marco (2004) VDAC: The channel at the interface between mitochondria and the cytosol. Molecular and Cellular Biochemistry 256/257(1-2):107-115.
Godbole, A. et al., (2003) VDAC is a conserved element of death pathways in plant and animal systems. Biochim. Biophys. Acta. 1642(1-2):87-96.
Jarver, Peter and Langel, Ulo (2004) The use of cell-penetrating peptides as a tool for gene regulation. Drug Discov Today 9(9):395-402.
Kayser H. et al Database UniProt; May 1, 1991 XP002395032 Accession No. vdac1_human Database accession No. P21796, Q5FVE7, Q9UIQ5, Q9UPL0.
Kim R., Unknotting the roles of Bcl-2 and Bcl-xL in cell death, Biochem Biophys Res Commun., 2005 vol. 333, No. 2; pp. 336-343.

(Continued)

*Primary Examiner* — Bridget E Bunner
*Assistant Examiner* — Fozia Hamud
(74) *Attorney, Agent, or Firm* — Rodney J. Fuller; Booth Udall Fuller, PLC

(57) ABSTRACT

The present invention relates generally to the mitochondrial protein, voltage-dependent anion channel (VDAC), polynucleotides encoding same and variants thereof, as well as peptide fragments, peptide derivatives and analogs. In particular, the present invention is directed to VDAC1 and specific amino acid and polynucleotide sequences thereof useful in inducing or regulating apoptosis and to pharmaceutical compositions comprising same useful in the treatment of diseases associated with aberrant apoptosis.

11 Claims, 16 Drawing Sheets

(56) References Cited

OTHER PUBLICATIONS

Lawen A. et al., Voltage-dependent anion-selective channel 1 (VDAC1)—a mitochondrial protein, rediscovered as a novel enzyme in the plasma membrane, International Journal of Biochemistry and Cell Biology, Exter, GB, Feb. 2005 vol. 37, No. 2; pp. 277-282.

Lazar et al., (1988) Transforming growth factor alpha: mutation of aspartic acid 47 and leucine 48 results in different biological activities. Mol Cell Biol, 8: 1247-52.

Li, Lin et al., (2004) A small molecule Smac mimic potentiates TRAIL- and TNF alpha-mediated cell death. Science 305(5689):1471-4.

Mendoza, F. J. et al., (2005) Anti-tumor chemotherapy utilizing peptide based approaches-apoptotic pathways, kinases and proteasome targets. Arch Immunol Ther Exp (Warsz) 53:47-60.

Messina A. et al., Characterization of the Human Porin Isoform 1 (HVDAC1) Gene by Amplification on the Whole Human Genome: A Tool for Porin Deficiency Analysis, Biochemical and Biophysical Research Communications, Apr. 21, 2000 vol. 270, No. 3; pp. 787-792.

Oupicky, David (2002) Development of long-circulating polyelectrolyte complexes for systemic delivery of genes. J Drug Target. 10(2):93-98.

Pillai, Omathanu and Panchagnula, Ramesh (2001) Polymers in drug delivery. Curr Opin Chem Biol. 5(4):447-51.

Sapra, Puja and Allen, Theresa M. (2004) Improved outcome when B-cell lymphoma is treated with combinations of immunoliposomal anticancer drugs targeted to both the CD19 and CD20 epitopes. Clin Cancer Res. 10(7):2530-7.

Schatzlein, Andreas G. (2003) Targeting of Synthetic Gene Delivery Systems. J Biomed Biotechnol. 2003 (2):149-158.

Shi Yong et al., Identificiation of the protein—protein contact site and interaction mode of human VDAC1 wtih Bcl-2 family proteins, Biochemical and Biophysical Research Communications, Jun. 13, 2003 vol. 305, No. 4; pp. 989-996.

Shimizu, Shigeon et al., (1999) Bcl-2 family proteins regulate the release of apoptogenic cytochrome c by the mitochondrial channel VDAC. Nature 399(6735):483-487.

Shimizu S. et al., Essential Role of Voltage-dependent Anion Channel in Various Forms of Apoptosis in Mammalian Cells, The Journal of Cell Biology, Jan. 22, 2001 vol. 152, No. 2; pp. 237-250.

Shoshan-Barmatz Varda and Gincel D., The Voltage-Dependent Anion Channel, Characterization, Modulation, and Role in Mitochondrial Function in Cell Life and Death, Cell Biochemistry and Biophysics, 2003 vol. 39, No. 3; pp. 279-292.

Sugiyama Tomoyasu et al., Activation of mitochondrial voltage-dependent anion channel by a pro-apoptotic BH3-only protein Bim, Oncogene, Jul. 25, 2002 vol. 21, No. 32; pp. 4944-4956.

Tatiana K Rostovtseva et al., "On the role of VDAC in Apoptosis: Fact and fiction", Journal of Bioenergetics and biomembranes 2005; 37(3): 129-42.

Tsujimoto, Yoshihide and Shimizu, Shigeomi (2002) The voltage-dependent anion channel: an essential player in apoptosis. Biochimie 849(2-3):187-193.

Wagner, Ernst et al., (2005) Targeting of Polyplexes: Toward Synthetic Virus Vector Systems. Adv Genet. 53PA:333-354.

Walensky L. D. (2004) Activation of apoptosis in vivo by a hydrocarbon-stapled BH3 helix. Science. 305 (5689):1466-1470.

Wells, (1990) Additivity of mutational effects in proteins. Biochemistry 29: 8509-17.

Zabala, Maider et al., (2004) Optimization of the Tet-on system to regulate interleukin 12 expression in the liver for the treatment of hepatic tumors. Cancer Res. 64(8):2799-2804.

Zaid H. et al., The voltage-dependent anion channel-1 modulates apoptotic cell death, Cell Death and Differentiation, Jul. 2005 vol. 12, No. 7; pp. 751-760.

Zalk, Ran et al., (2005) Oligomeric states of the voltage-dependent anion channel and cytochrome c release from mitochondria. Biochem J. 386(pt 1):73-83.

Zheng, Yanhua et al., (2004) Essential role of the voltage-dependent anion channel (VDAC) in mitochondrial permeability transition pore opening and cytochrome c release induced by arsenic trioxide. Oncogene 23(6):1239-1247.

Abu-Hamad, S. et al., (2009) The VDAC1 N-terminus is essential both for apoptosis and the protective effect of anti-apoptotic proteins. J Cell Sci. 122: 1906-1916.

European Search Report for European Patent Application No. 10178317 dated Aug. 30, 2011.

International Preliminary Report on Patentability for PCT/IL2006/000311 dated Sep. 12, 2007.

International Search Report for PCT/IL2006/000311 dated Apr. 2, 2007.

* cited by examiner

FIGURE 3A 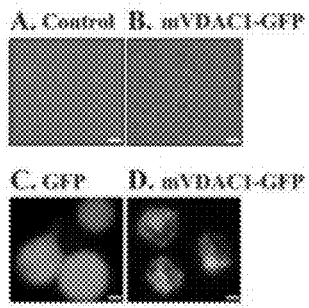 FIGURE 3B 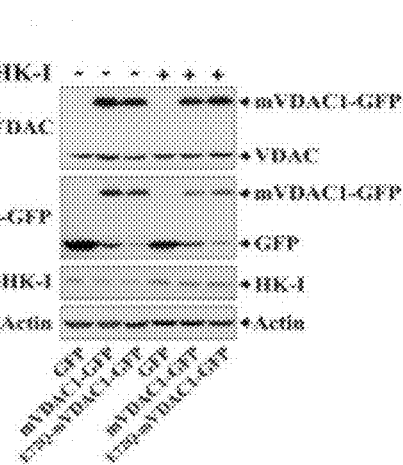
FIGURE 3C
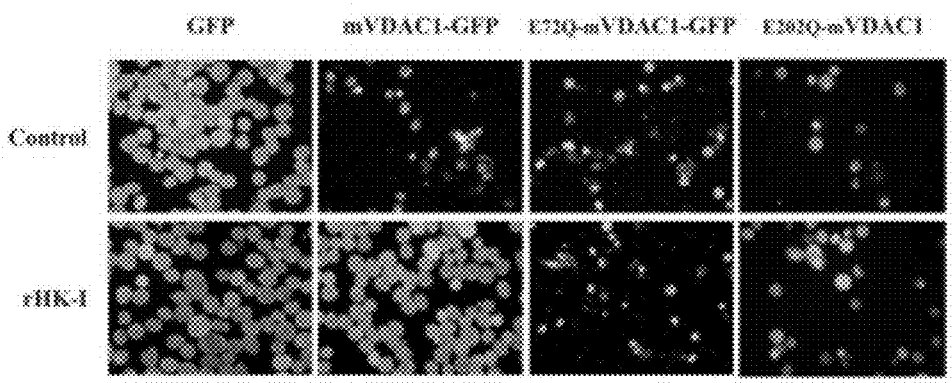
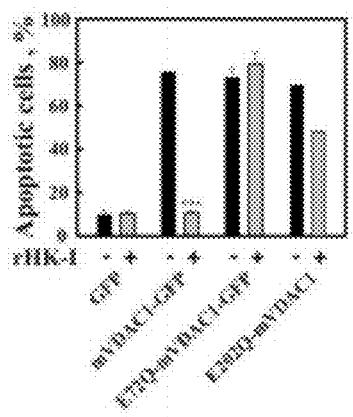 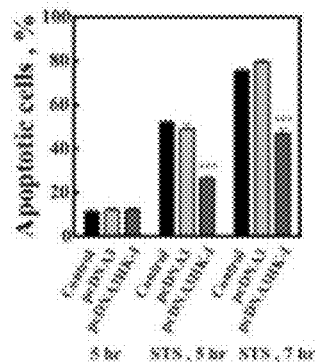
FIGURE 3D FIGURE 3E

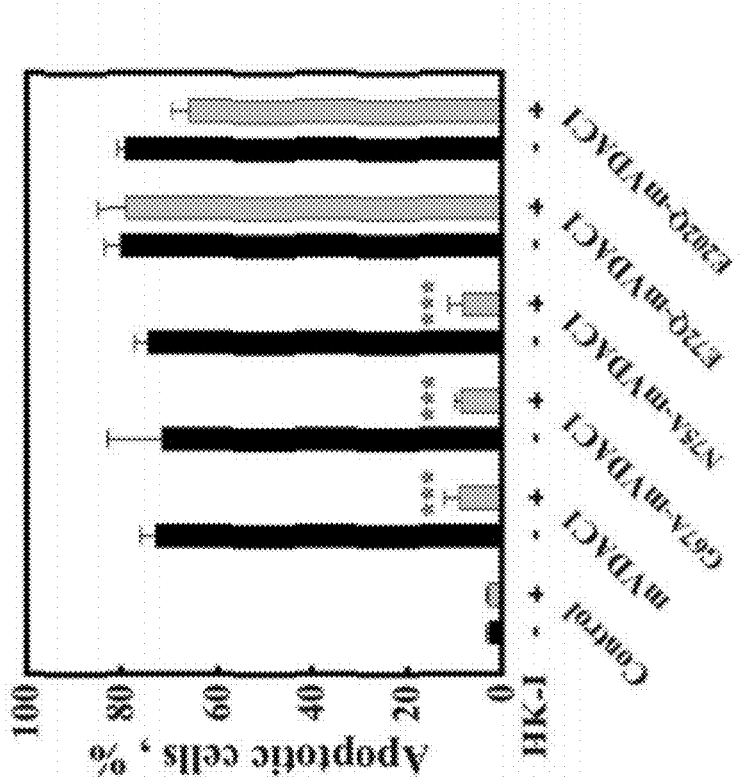
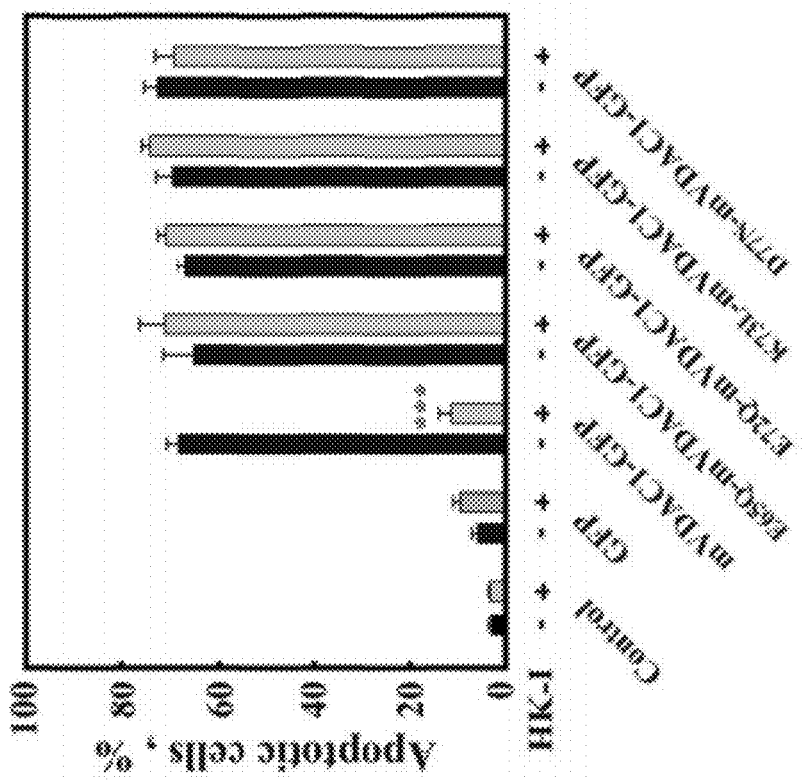
FIGURE 4A
FIGURE 4B

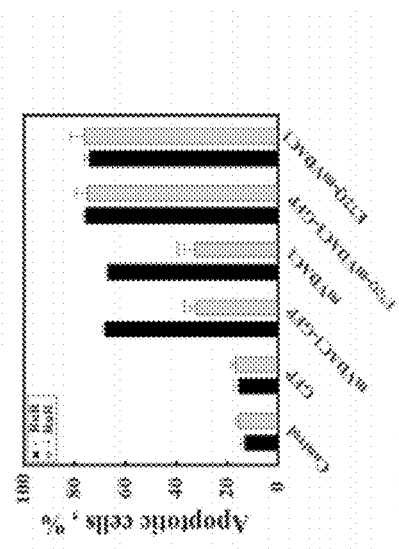
FIGURE 5A
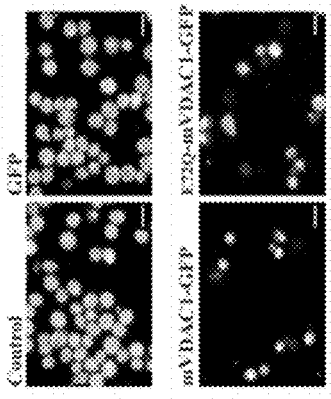
FIGURE 5B
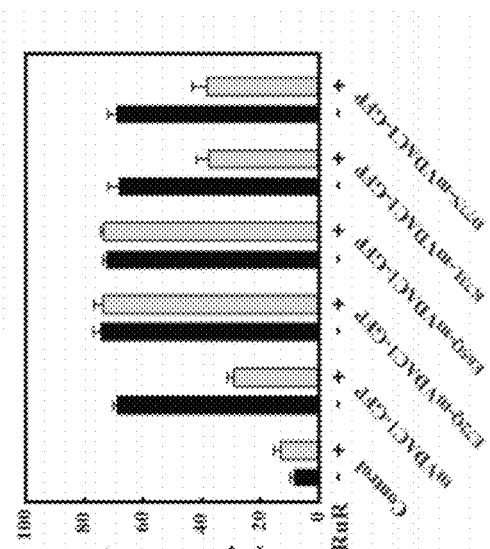
FIGURE 5C
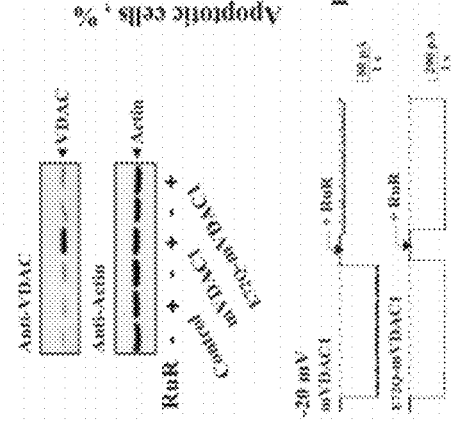
FIGURE 5D
FIGURE 5E (SEQ ID NO:21)

FIGURE 8A

```
HUMAN VDAC1    1 MAVPPTYADL GKSARDVFTK GYGFGLIKLD LKTKSENGLE FTSSGSANTE TTKVTGSLET KYRWTEYGLT FTEKWNTDNT
MOUSE VDAC1    1 MAVPPTYADL GKSARDVFTK GYGFGLIKLD LKTKSENGLE FTSSGSANTE TTKVNGSLET KYRWTEYGLT FTEKWNTDNT
RAT VDAC1      1 MAVPPTYADL GKSARDVFTK GYGFGLIKLD LKTKSENGLE FTSSGSANTE TTKVNGSLET KYRWTEYGLT FTEKWNTDNT

81 LGTEITVEDQ LARGLKLTFD SSFSPNTGKK NAKIKTGYKR EHINLGCDMD FDIAGPSIRG ALVLGYEGWL AGYQMNFETA
              81 LGTEITVEDQ LARGLKLTFD SSFSPNTGKK NAKIKTGYKR EHINLGCDVD FDIAGPSIRG ALVLGYEGWL AGYQMNFETS
              81 LGTEITVEDQ LARGLKLTFD SSFSPNTGKK NAKIKTGYKR EHINLGCDVD FDIAGPSIRG ALVLGYEGWL AGYQMNFETS

161 KSRVTQSNFA VGYKTDEFQL HTNVNDGTEF GGSIYQKVNK KLETAVNLAW TAGNSNTRFG IAAKYQIDPD ACFSAKVNNS
             161 KSRVTQSNFA VGYKTDEFQL HTNVNDGTEF GGSIYQKVNK KLETAVNLAW TAGNSNTRFG IAAKYQVDPD ACFSAKVNNS
             161 KSRVTQSNFA VGYKTDEFQL HTNVNDGTEF GGSIYQKVNK KLETAVNLAW TAGNSNTRFG IAAKYQVDPD ACFSAKVNNS

241 SLIGLGYTQT LKPGIKLTLS ALLDGKNVNA GGHKLGLGLE FQA        (SEQ ID NO:21)
             241 SLIGLGYTQT LKPGIKLTLS ALLDGKNVNA GGHKLGLGLE FQA        (SEQ ID NO:24)
             241 SLIGLGYTQT LKPGIKLTLS ALLDGKNVNA GGHKLGLGLE FQA        (SEQ ID NO:27)
```

FIGURE 8B

```
HUMAN VDAC2    1 MATHGQTCAR PMCIPPSYAD LGKAARDIFN KGFGFGLVKL DVKTKSCSGV EFSTSGSSNT DTGKVTGTLE TKYKWCEYGL
MOUSE VDAC2    1 MAECCVPVCP RPMCIPPPYA DLGKAARDIF NKGFGFGLVK LDVKTKSCSG VEFSTSGSSN TDTGKVSGTL ETKYKWCEYG
RAT VDAC2      1 MAECCVPVCQ RPICIPPPYA DLGKAARDIF NKGFGFGLVK LDVKTKSCSG VEFSTSGSSN TDTGKVSGTL ETKYKWCEYG

81 TFTEKWNTDN TLGTEIAIED QICQGLKLTF DTTFSPNTGK KSGKIKSSYK RECINLGCDV DFDFAGPAIH GSAVFGYEGW
              81 LTFTEKWNTD NTLGTEIAIE DQICQGLKLT FDTTFSPNTG KKSGKIKSAY KRECINLGCD VDFDFAGPAI HGSAVFGYEG
              81 LTFTEKWNTD NTLGTEIAIE DQICQGLKLT FDTTFSPNTG KKSGKIKSAY KRECINLGCD VDFDFAGPAI HGSAVFGYEG

161 LAGYQMTFDS AKSKLTRNNF AVGYRTGDFQ LHTNVNDGTE FGGSIYQKVC EDLDTSVNLA WTSGTNCTRF GIAAKYQLDP
             161 WLAGYQMTFD SAKSKLTRSN FAVGYRTGDF QLHTNVNNGT EFGGSIYQKV CEDFDTSVNL AWTSGTNCTR FGIAAKYQLD
             161 WLAGYQMTFD SAKSKLTRSN FAVGYRTGDF QLHTNVNNGT EFGGSIYQKV CEDFDTSVNL AWTSGTNCTR FGIAAKYQLD

241 TASISAKVNN SSLIGVGYTQ TLRPGVKLTL SALVDGKSIN AGHKVGLAL  ELEA       (SEQ ID NO:22)
             241 PTASISAKVN NSSLIGVGYT QTLRPGVKLT LSALVDGKSF NAGGHKLGLA LELEA      (SEQ ID NO:25)
             241 PTASISAKVN NSSLIGVGYT QTLRPGVKLT LSALVDGKSF NAGGHKLGLA LELEA      (SEQ ID NO:28)
```

FIGURE 8C

```
HUMAN VDAC3   1 MCNTPTYCDL GKAAKDVFNK GYGFGMVKID LKTKSCSGVE FSTSGHAYTD TGKASGNLET KYKVCNYGLT FTQKWNTDNT
MOUSE VDAC3   1 MCNTPTYCDL GKAAKDVFNK GYGFGMVKID LKTKSCSGVE FSTSGHAYTD TGKASGNLET KYKVCNYGLT FTQKWNTDNT
RAT VDAC3     1 MCSTPTYCDL GKAAKDVFNK GYGFGMVKID LKTKSCSGVE FSTSGHAYTD TGKASGNLET KYKVCNYGLI FTQKWNTDNT

81 LGTEISWENK LAEGLKLTLD TIFVPNTGKK SGKLKASYKR DCFSVGSNVD IDFSGPTIYG WAVLAFEGWL AGYQMSFDTA
             81 LGTEISWENK LAEGLKLTLD TIFVPNTGKK SGKLKASYRR DCFSLGSNVD IDFSGPTIYG WAVLAFEGWL AGYQMSFDTA
             81 LGTEISWENK LAEGLKLTVD TIFVPNTGKK SGKLKASYRR DCFSVGSKVD IDFSGPTIYG WAVLAFEGWL AGYQMSFDTA

161 KSKLSQNNFA LGYKAADFQL HTHVNDGTEF GGSIYQKVNE KIETSINLAW TAGSNNTRFG IAAKYMLDCR TSLSAKVNNA
            161 KSKLSQNNFA LGYKAADFQL HTHVNDGTEF GGSIYQKVNE RIETSINLAW TAGSNNTRFG IAAKYKLDCR TSLSAKVNNA
            161 KSKLCQNNFA LGYKAEDFQL HTHVNDGTEF GGSIYQRVNE KIETSINLAW TAGSNNTRFG IAAKYRLDCR TSLSAKVNNA

241 SLIGLGYTQT LRPGVKLTLS ALIDGKNFSA GGHKVGLGFE LEA  (SEQ ID NO:23)
            241 SLIGLGYTQT LRPGVKLTLS ALIDGKNFNA GGHKVGLGFE LEA  (SEQ ID NO:26)
            241 SLIGLGYTQS LRPGVKLTLS ALVDGKNFNA GGHKVGLGFE LEA  (SEQ ID NO:29)
```

FIGURE 8D

COMPARISON OF THE VDAC1-3 SEQUENCES IN 2 CYTOSOLIC β-LOOPS

```
VDAC1  71 FTEKWNTDNT LGTEITVEDQ       (POSITIONS 71-90 OF SEQ ID NO:21)
VDAC2  71 TKYKWCEYGL TFTEKWNTDN       (POSITIONS 71-90 OF SEQ ID NO:22)
VDAC3  71 FTQKWNTDNT LGTEISWENK       (POSITIONS 71-90 OF SEQ ID NO:23)

VDAC1 181 HTNVNDGTEF GGSIYQKVNK KLETAVNLAW   (POSITIONS 181-210 OF SEQ ID NO:21)
VDAC2 181 AVGYRTGDFQ LHTNVNDGTE FGGSIYQKVC   (POSITIONS 181-210 OF SEQ ID NO:22)
VDAC3 181 HTHVNDGTEF GGSIYQKVNE KIETSIN      (POSITIONS 181-207 OF SEQ ID NO:23)
```

FIGURE 9
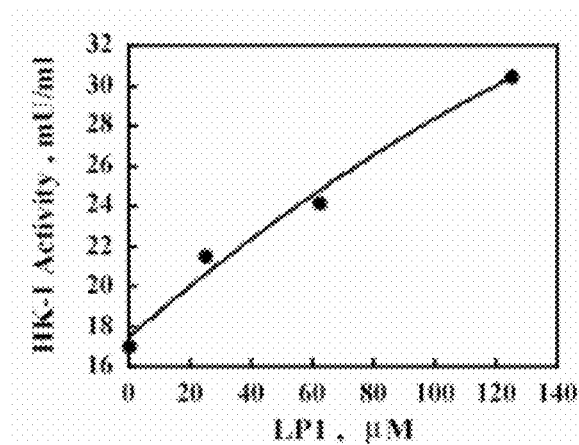
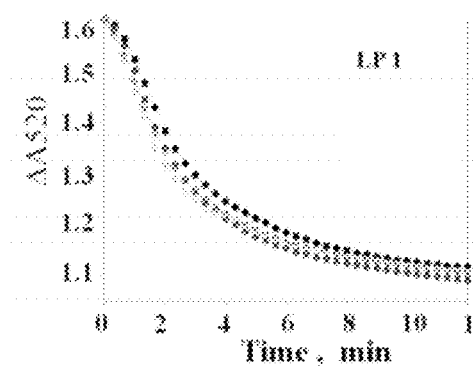
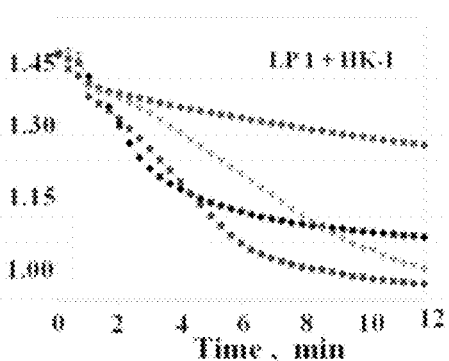

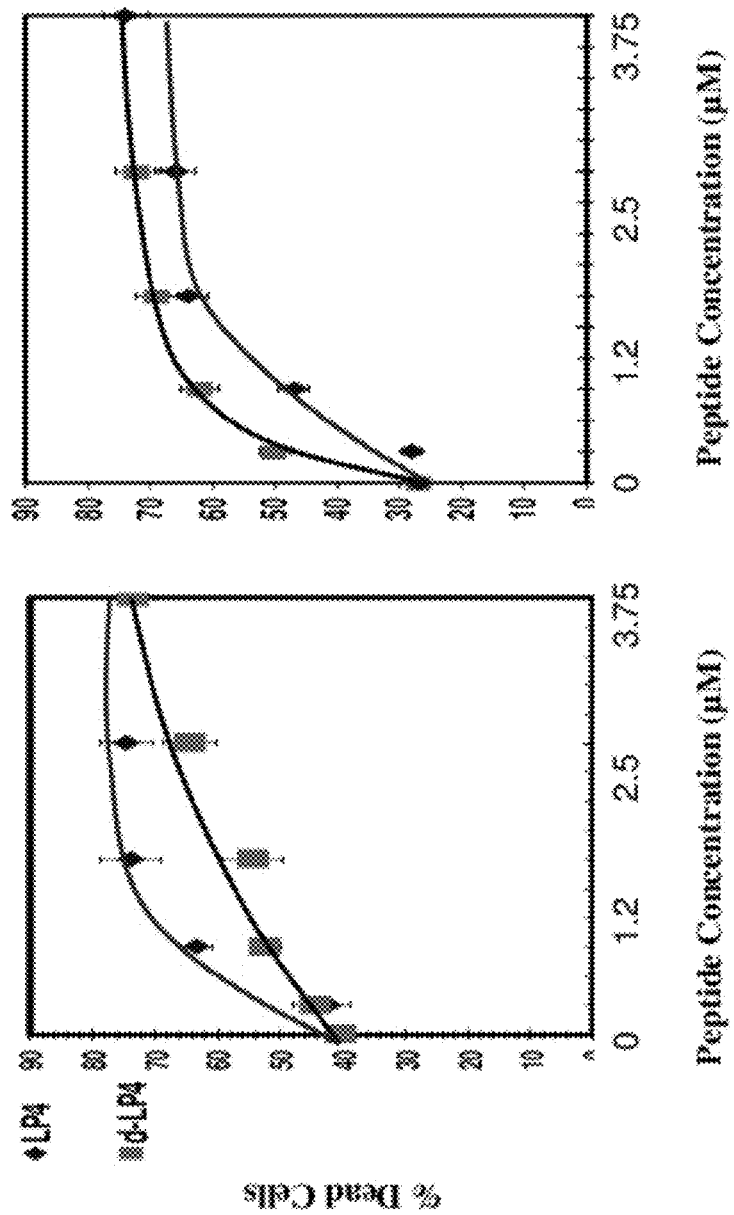

SEQUENCE LISTING

<160> NUMBER OF SEQ ID NOS: 78

<210> SEQ ID NO 1
<211> LENGTH: 26
<212> TYPE: PRT

-continued

```
<213> ORGANISM: Artificial Sequence
<220> FEATURE:
<223> OTHER INFORMATION: SYNTHETIC PEPTIDE

<400> SEQUENCE: 1

Met Ala Val Pro Pro Thr Tyr Ala Asp Leu Gly Lys Ser Ala Arg Asp
1               5                   10                  15

Val Phe Thr Lys Gly Tyr Gly Phe Gly Leu
            20                  25

<210> SEQ ID NO 2
<211> LENGTH: 15
<212> TYPE: PRT
<213> ORGANISM: Artificial Sequence
<220> FEATURE:
<223> OTHER INFORMATION: SYNTHETIC PEPTIDE

<400> SEQUENCE: 2

Trp Thr Glu Tyr Gly Leu Thr Phe Thr Glu Lys Trp Asn Thr Asp
1               5                   10                  15

<210> SEQ ID NO 3
<211> LENGTH: 20
<212> TYPE: PRT
<213> ORGANISM: Artificial Sequence
<220> FEATURE:
<223> OTHER INFORMATION: SYNTHETIC PEPTIDE

<400> SEQUENCE: 3

Ser Ser Phe Ser Pro Asn Thr Gly Lys Lys Asn Ala Lys Ile Lys Thr
1               5                   10                  15

Gly Tyr Lys Arg
            20

<210> SEQ ID NO 4
<211> LENGTH: 18
<212> TYPE: PRT
<213> ORGANISM: Artificial Sequence
<220> FEATURE:
<223> OTHER INFORMATION: SYNTHETIC PEPTIDE

<400> SEQUENCE: 4

Glu Thr Ala Lys Ser Arg Val Thr Gln Ser Asn Phe Ala Val Gly Tyr
1               5                   10                  15

Lys Thr

<210> SEQ ID NO 5
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 5

Lys Lys Leu Glu Thr Ala Val Asn Leu Ala Trp Thr Ala Gly Asn Ser
1               5                   10                  15

Asn

<210> SEQ ID NO 6
<211> LENGTH: 78
<212> TYPE: DNA
<213> ORGANISM: Artificial Sequence
<220> FEATURE:
<223> OTHER INFORMATION: NUCLEOTIDE SEQUENCE CORRESPONDING TO SYNTHETIC
      PEPTIDE
```

-continued

<210> SEQ ID NO 6

<400> SEQUENCE: 6

```
atggctgtgc cacccacgta tgccgatctt ggcaaatctg ccagggatgt cttcaccaag    60
ggctatggat ttggctta                                                  78
```

<210> SEQ ID NO 7
<211> LENGTH: 48
<212> TYPE: DNA
<213> ORGANISM: Artificial Sequence
<220> FEATURE:
<223> OTHER INFORMATION: NUCLEOTIDE SEQUENCE CORRESPONDING TO SYNTHETIC
      PEPTIDE

<400> SEQUENCE: 7

```
tggactgagt acggcctgac gtttacagag aaatggaata ccgacaat                 48
```

<210> SEQ ID NO 8
<211> LENGTH: 69
<212> TYPE: DNA
<213> ORGANISM: Artificial Sequence
<220> FEATURE:
<223> OTHER INFORMATION: NUCLEOTIDE SEQUENCE CORRESPONDING TO SYNTHETIC
      PEPTIDE

<400> SEQUENCE: 8

```
tcatccttct cacctaacac tgggaaaaaa aatgctaaaa tcaagacagg gtacaagcgg    60
gagcacatt                                                            69
```

<210> SEQ ID NO 9
<211> LENGTH: 54
<212> TYPE: DNA
<213> ORGANISM: Artificial Sequence
<220> FEATURE:
<223> OTHER INFORMATION: NUCLEOTIDE SEQUENCE CORRESPONDING TO SYNTHETIC
      PEPTIDE

<400> SEQUENCE: 9

```
gagactgcaa atcccgagt gacccagagc aactttgcag ttggctacaa gact            54
```

<210> SEQ ID NO 10
<211> LENGTH: 51
<212> TYPE: DNA
<213> ORGANISM: Artificial Sequence
<220> FEATURE:
<223> OTHER INFORMATION: NUCLEOTIDE SEQUENCE CORRESPONDING TO SYNTHETIC
      PEPTIDE

<400> SEQUENCE: 10

```
aagaagttgg agaccgctgt caatcttgcc tggacagcag gaaacagtaa c              51
```

<210> SEQ ID NO 11
<211> LENGTH: 43
<212> TYPE: PRT
<213> ORGANISM: Artificial Sequence
<220> FEATURE:
<223> OTHER INFORMATION: SYNTHETIC PEPTIDE

<400> SEQUENCE: 11

```
Met Arg Gln Ile Lys Ile Trp Phe Gln Asn Arg Met Lys Trp Lys
1               5                   10                  15

Lys Met Ala Val Pro Pro Thr Tyr Ala Asp Leu Gly Lys Ser Ala Arg
            20                  25                  30

Asp Val Phe Thr Lys Gly Tyr Gly Phe Gly Leu
        35                  40
```

```
<210> SEQ ID NO 12
<211> LENGTH: 42
<212> TYPE: PRT
<213> ORGANISM: Artificial Sequence
<220> FEATURE:
<223> OTHER INFORMATION: SYNTHETIC PEPTIDE

<400> SEQUENCE: 12

Met Arg Gln Ile Lys Ile Trp Phe Gln Asn Arg Arg Met Lys Trp Lys
1               5                   10                  15

Lys Ser Trp Thr Trp Glu Trp Thr Glu Tyr Gly Leu Thr Phe Thr Glu
            20                  25                  30

Lys Trp Asn Thr Asp Lys Trp Thr Trp Lys
        35                  40

<210> SEQ ID NO 13
<211> LENGTH: 47
<212> TYPE: PRT
<213> ORGANISM: Artificial Sequence
<220> FEATURE:
<223> OTHER INFORMATION: SYNTHETIC PEPTIDE

<400> SEQUENCE: 13

Met Arg Gln Ile Lys Ile Trp Phe Gln Asn Arg Arg Met Lys Trp Lys
1               5                   10                  15

Lys Ser Trp Thr Trp Glu Ser Ser Phe Ser Pro Asn Thr Gly Lys Lys
            20                  25                  30

Asn Ala Lys Ile Lys Thr Gly Tyr Lys Arg Lys Trp Thr Trp Lys
        35                  40                  45

<210> SEQ ID NO 14
<211> LENGTH: 45
<212> TYPE: PRT
<213> ORGANISM: Artificial Sequence
<220> FEATURE:
<223> OTHER INFORMATION: SYNTHETIC PEPTIDE

<400> SEQUENCE: 14

Met Arg Gln Ile Lys Ile Trp Phe Gln Asn Arg Arg Met Lys Trp Lys
1               5                   10                  15

Lys Ser Trp Thr Trp Glu Glu Thr Ala Lys Ser Arg Val Thr Gln Ser
            20                  25                  30

Asn Phe Ala Val Gly Tyr Lys Thr Lys Trp Thr Trp Lys
        35                  40                  45

<210> SEQ ID NO 15
<211> LENGTH: 44
<212> TYPE: PRT
<213> ORGANISM: Artificial Sequence
<220> FEATURE:
<223> OTHER INFORMATION: SYNTHETIC PEPTIDE

<400> SEQUENCE: 15

Met Arg Gln Ile Lys Ile Trp Phe Gln Asn Arg Arg Met Lys Trp Lys
1               5                   10                  15

Lys Ser Trp Thr Trp Glu Lys Lys Leu Glu Thr Ala Val Asn Leu Ala
            20                  25                  30

Trp Thr Ala Gly Asn Ser Asn Lys Trp Thr Trp Lys
        35                  40

<210> SEQ ID NO 16
<211> LENGTH: 132
<212> TYPE: DNA
<213> ORGANISM: Artificial Sequence
```

```
<220> FEATURE:
<223> OTHER INFORMATION: NUCLEOTIDE SEQUENCE CORRESPONDING TO SYNTHETIC
      PEPTIDE

<400> SEQUENCE: 16
atgcgtcaga ttaaaatttg gtttcagaat cgtcgtatga aatggaaaaa aatggctgtg     60
ccacccacgt atgccgatct tggcaaatct gccagggatg tcttcaccaa gggctatgga    120
tttggcttat ga                                                        132

<210> SEQ ID NO 17
<211> LENGTH: 132
<212> TYPE: DNA
<213> ORGANISM: Artificial Sequence
<220> FEATURE:
<223> OTHER INFORMATION: NUCLEOTIDE SEQUENCE CORRESPONDING TO SYNTHETIC
      PEPTIDE

<400> SEQUENCE: 17
atgcgtcaga ttaaaatttg gtttcagaat cgtcgtatga aatggaaaaa atcctggacc     60
tgggaatgga ctgagtacgg cctgacgttt acagagaaat ggaataccga caataaatgg    120
acctggaaat ga                                                        132

<210> SEQ ID NO 18
<211> LENGTH: 153
<212> TYPE: DNA
<213> ORGANISM: Artificial Sequence
<220> FEATURE:
<223> OTHER INFORMATION: NUCLEOTIDE SEQUENCE CORRESPONDING TO SYNTHETIC
      PEPTIDE

<400> SEQUENCE: 18
atgcgtcaga ttaaaatttg gtttcagaat cgtcgtatga aatggaaaaa atcctggacc     60
tgggaatcat ccttctcacc taacactggg aaaaaaaatg ctaaaatcaa gacagggtac    120
aagcgggagc acattaaatg gacctggaaa tga                                 153

<210> SEQ ID NO 19
<211> LENGTH: 138
<212> TYPE: DNA
<213> ORGANISM: Artificial Sequence
<220> FEATURE:
<223> OTHER INFORMATION: NUCLEOTIDE SEQUENCE CORRESPONDING TO SYNTHETIC
      PEPTIDE

<400> SEQUENCE: 19
atgcgtcaga ttaaaatttg gtttcagaat cgtcgtatga aatggaaaaa atcctggacc     60
tgggaagaga ctgcaaaatc ccgagtgacc cagagcaact ttgcagttgg ctacaagact    120
aaatggacct ggaaatga                                                  138

<210> SEQ ID NO 20
<211> LENGTH: 135
<212> TYPE: DNA
<213> ORGANISM: Artificial Sequence
<220> FEATURE:
<223> OTHER INFORMATION: NUCLEOTIDE SEQUENCE CORRESPONDING TO SYNTHETIC
      PEPTIDE

<400> SEQUENCE: 20
atgcgtcaga ttaaaatttg gtttcagaat cgtcgtatga aatggaaaaa atcctggacc     60
tgggaaaaga agttggagac cgctgtcaat cttgcctgga cagcaggaaa cagtaacaaa    120
tggacctgga aatga                                                     135
```

```
<210> SEQ ID NO 21
<211> LENGTH: 283
<212> TYPE: PRT
<213> ORGANISM: HOMO SAPIENS
<300> PUBLICATION INFORMATION:
<308> DATABASE ACCESSION NUMBER: NP_00365
<309> DATABASE ENTRY DATE: 2005-12-25
<313> RELEVANT RESIDUES IN SEQ ID NO: (1)..(283)

<400> SEQUENCE: 21

Met Ala Val Pro Pro Thr Tyr Ala Asp Leu Gly Lys Ser Ala Arg Asp
1               5                   10                  15

Val Phe Thr Lys Gly Tyr Gly Phe Gly Leu Ile Lys Leu Asp Leu Lys
            20                  25                  30

Thr Lys Ser Glu Asn Gly Leu Glu Phe Thr Ser Ser Gly Ser Ala Asn
        35                  40                  45

Thr Glu Thr Thr Lys Val Thr Gly Ser Leu Glu Thr Lys Tyr Arg Trp
    50                  55                  60

Thr Glu Tyr Gly Leu Thr Phe Thr Glu Lys Trp Asn Thr Asp Asn Thr
65                  70                  75                  80

Leu Gly Thr Glu Ile Thr Val Glu Asp Gln Leu Ala Arg Gly Leu Lys
                85                  90                  95

Leu Thr Phe Asp Ser Ser Phe Ser Pro Asn Thr Gly Lys Lys Asn Ala
            100                 105                 110

Lys Ile Lys Thr Gly Tyr Lys Arg Glu His Ile Asn Leu Gly Cys Asp
        115                 120                 125

Met Asp Phe Asp Ile Ala Gly Pro Ser Ile Arg Gly Ala Leu Val Leu
    130                 135                 140

Gly Tyr Glu Gly Trp Leu Ala Gly Tyr Gln Met Asn Phe Glu Thr Ala
145                 150                 155                 160

Lys Ser Arg Val Thr Gln Ser Asn Phe Ala Val Gly Tyr Lys Thr Asp
                165                 170                 175

Glu Phe Gln Leu His Thr Asn Val Asn Asp Gly Thr Glu Phe Gly Gly
            180                 185                 190

Ser Ile Tyr Gln Lys Val Asn Lys Lys Leu Glu Thr Ala Val Asn Leu
        195                 200                 205

Ala Trp Thr Ala Gly Asn Ser Asn Thr Arg Phe Gly Ile Ala Ala Lys
    210                 215                 220

Tyr Gln Ile Asp Pro Asp Ala Cys Phe Ser Ala Lys Val Asn Asn Ser
225                 230                 235                 240

Ser Leu Ile Gly Leu Gly Tyr Thr Gln Thr Leu Lys Pro Gly Ile Lys
                245                 250                 255

Leu Thr Leu Ser Ala Leu Leu Asp Gly Lys Asn Val Asn Ala Gly Gly
            260                 265                 270

His Lys Leu Gly Leu Gly Leu Glu Phe Gln Ala
        275                 280

<210> SEQ ID NO 22
<211> LENGTH: 294
<212> TYPE: PRT
<213> ORGANISM: HOMO SAPIENS
<300> PUBLICATION INFORMATION:
<308> DATABASE ACCESSION NUMBER: NP_00366
<309> DATABASE ENTRY DATE: 2005-10-18
<313> RELEVANT RESIDUES IN SEQ ID NO: (1)..(294)

<400> SEQUENCE: 22

Met Ala Thr His Gly Gln Thr Cys Ala Arg Pro Met Cys Ile Pro Pro
1               5                   10                  15
```

```
Ser Tyr Ala Asp Leu Gly Lys Ala Ala Arg Asp Ile Phe Asn Lys Gly
            20                  25                  30

Phe Gly Phe Gly Leu Val Lys Leu Asp Val Lys Thr Lys Ser Cys Ser
        35                  40                  45

Gly Val Glu Phe Ser Thr Ser Gly Ser Ser Asn Thr Asp Thr Gly Lys
    50                  55                  60

Val Thr Gly Thr Leu Glu Thr Lys Tyr Lys Trp Cys Glu Tyr Gly Leu
65                  70                  75                  80

Thr Phe Thr Glu Lys Trp Asn Thr Asp Asn Thr Leu Gly Thr Glu Ile
                85                  90                  95

Ala Ile Glu Asp Gln Ile Cys Gln Gly Leu Lys Leu Thr Phe Asp Thr
            100                 105                 110

Thr Phe Ser Pro Asn Thr Gly Lys Lys Ser Gly Lys Ile Lys Ser Ser
        115                 120                 125

Tyr Lys Arg Glu Cys Ile Asn Leu Gly Cys Asp Val Asp Phe Asp Phe
    130                 135                 140

Ala Gly Pro Ala Ile His Gly Ser Ala Val Phe Gly Tyr Glu Gly Trp
145                 150                 155                 160

Leu Ala Gly Tyr Gln Met Thr Phe Asp Ser Ala Lys Ser Lys Leu Thr
                165                 170                 175

Arg Asn Asn Phe Ala Val Gly Tyr Arg Thr Gly Asp Phe Gln Leu His
            180                 185                 190

Thr Asn Val Asn Asp Gly Thr Glu Phe Gly Gly Ser Ile Tyr Gln Lys
        195                 200                 205

Val Cys Glu Asp Leu Asp Thr Ser Val Asn Leu Ala Trp Thr Ser Gly
    210                 215                 220

Thr Asn Cys Thr Arg Phe Gly Ile Ala Ala Lys Tyr Gln Leu Asp Pro
225                 230                 235                 240

Thr Ala Ser Ile Ser Ala Lys Val Asn Asn Ser Ser Leu Ile Gly Val
                245                 250                 255

Gly Tyr Thr Gln Thr Leu Arg Pro Gly Val Lys Leu Thr Leu Ser Ala
            260                 265                 270

Leu Val Asp Gly Lys Ser Ile Asn Ala Gly Gly His Lys Val Gly Leu
        275                 280                 285

Ala Leu Glu Leu Glu Ala
    290

<210> SEQ ID NO 23
<211> LENGTH: 283
<212> TYPE: PRT
<213> ORGANISM: HOMO SAPIENS
<300> PUBLICATION INFORMATION:
<308> DATABASE ACCESSION NUMBER: NP_005653
<309> DATABASE ENTRY DATE: 2005-10-17
<313> RELEVANT RESIDUES IN SEQ ID NO: (1)..(283)

<400> SEQUENCE: 23

Met Cys Asn Thr Pro Thr Tyr Cys Asp Leu Gly Lys Ala Ala Lys Asp
1               5                   10                  15

Val Phe Asn Lys Gly Tyr Gly Phe Gly Met Val Lys Ile Asp Leu Lys
            20                  25                  30

Thr Lys Ser Cys Ser Gly Val Glu Phe Ser Thr Ser Gly His Ala Tyr
        35                  40                  45

Thr Asp Thr Gly Lys Ala Ser Gly Asn Leu Glu Thr Lys Tyr Lys Val
    50                  55                  60

Cys Asn Tyr Gly Leu Thr Phe Thr Gln Lys Trp Asn Thr Asp Asn Thr
```

-continued

```
                65                  70                  75                  80
Leu Gly Thr Glu Ile Ser Trp Glu Asn Lys Leu Ala Glu Gly Leu Lys
                    85                  90                  95

Leu Thr Leu Asp Thr Ile Phe Val Pro Asn Thr Gly Lys Lys Ser Gly
                100                 105                 110

Lys Leu Lys Ala Ser Tyr Lys Arg Asp Cys Phe Ser Val Gly Ser Asn
                115                 120                 125

Val Asp Ile Asp Phe Ser Gly Pro Thr Ile Tyr Gly Trp Ala Val Leu
130                 135                 140

Ala Phe Glu Gly Trp Leu Ala Gly Tyr Gln Met Ser Phe Asp Thr Ala
145                 150                 155                 160

Lys Ser Lys Leu Ser Gln Asn Asn Phe Ala Leu Gly Tyr Lys Ala Ala
                165                 170                 175

Asp Phe Gln Leu His Thr His Val Asn Asp Gly Thr Glu Phe Gly Gly
                180                 185                 190

Ser Ile Tyr Gln Lys Val Asn Glu Lys Ile Glu Thr Ser Ile Asn Leu
                195                 200                 205

Ala Trp Thr Ala Gly Ser Asn Asn Thr Arg Phe Gly Ile Ala Ala Lys
210                 215                 220

Tyr Met Leu Asp Cys Arg Thr Ser Leu Ser Ala Lys Val Asn Asn Ala
225                 230                 235                 240

Ser Leu Ile Gly Leu Gly Tyr Thr Gln Thr Leu Arg Pro Gly Val Lys
                245                 250                 255

Leu Thr Leu Ser Ala Leu Ile Asp Gly Lys Asn Phe Ser Ala Gly Gly
                260                 265                 270

His Lys Val Gly Leu Gly Phe Glu Leu Glu Ala
                275                 280

<210> SEQ ID NO 24
<211> LENGTH: 283
<212> TYPE: PRT
<213> ORGANISM: MUS MUSCULUS
<300> PUBLICATION INFORMATION:
<308> DATABASE ACCESSION NUMBER: NP_035824
<309> DATABASE ENTRY DATE: 2005-12-11
<313> RELEVANT RESIDUES IN SEQ ID NO: (1)..(283)

<400> SEQUENCE: 24

Met Ala Val Pro Pro Thr Tyr Ala Asp Leu Gly Lys Ser Ala Arg Asp
1               5                   10                  15

Val Phe Thr Lys Gly Tyr Gly Phe Gly Leu Ile Lys Leu Asp Leu Lys
                20                  25                  30

Thr Lys Ser Glu Asn Gly Leu Glu Phe Thr Ser Ser Gly Ser Ala Asn
                35                  40                  45

Thr Glu Thr Thr Lys Val Asn Gly Ser Leu Glu Thr Lys Tyr Arg Trp
        50                  55                  60

Thr Glu Tyr Gly Leu Thr Phe Thr Glu Lys Trp Asn Thr Asp Asn Thr
65                  70                  75                  80

Leu Gly Thr Glu Ile Thr Val Glu Asp Gln Leu Ala Arg Gly Leu Lys
                85                  90                  95

Leu Thr Phe Asp Ser Ser Phe Ser Pro Asn Thr Gly Lys Lys Asn Ala
                100                 105                 110

Lys Ile Lys Thr Gly Tyr Lys Arg Glu His Ile Asn Leu Gly Cys Asp
                115                 120                 125

Val Asp Phe Asp Ile Ala Gly Pro Ser Ile Arg Gly Ala Leu Val Leu
130                 135                 140
```

```
Gly Tyr Glu Gly Trp Leu Ala Gly Tyr Gln Met Asn Phe Glu Thr Ser
145                 150                 155                 160

Lys Ser Arg Val Thr Gln Ser Asn Phe Ala Val Gly Tyr Lys Thr Asp
                165                 170                 175

Glu Phe Gln Leu His Thr Asn Val Asn Asp Gly Thr Glu Phe Gly Gly
            180                 185                 190

Ser Ile Tyr Gln Lys Val Asn Lys Leu Glu Thr Ala Val Asn Leu
        195                 200                 205

Ala Trp Thr Ala Gly Asn Ser Asn Thr Arg Phe Gly Ile Ala Ala Lys
    210                 215                 220

Tyr Gln Val Asp Pro Asp Ala Cys Phe Ser Ala Lys Val Asn Asn Ser
225                 230                 235                 240

Ser Leu Ile Gly Leu Gly Tyr Thr Gln Thr Leu Lys Pro Gly Ile Lys
                245                 250                 255

Leu Thr Leu Ser Ala Leu Leu Asp Gly Lys Asn Val Asn Ala Gly Gly
            260                 265                 270

His Lys Leu Gly Leu Gly Leu Glu Phe Gln Ala
        275                 280
```

<210> SEQ ID NO 25
<211> LENGTH: 295
<212> TYPE: PRT
<213> ORGANISM: MUS MUSCULUS
<300> PUBLICATION INFORMATION:
<308> DATABASE ACCESSION NUMBER: NP_035825
<309> DATABASE ENTRY DATE: 2005-12-11
<313> RELEVANT RESIDUES IN SEQ ID NO: (1)..(295)

<400> SEQUENCE: 25

```
Met Ala Glu Cys Cys Val Pro Val Cys Pro Arg Pro Met Cys Ile Pro
1               5                   10                  15

Pro Pro Tyr Ala Asp Leu Gly Lys Ala Ala Arg Asp Ile Phe Asn Lys
            20                  25                  30

Gly Phe Gly Phe Gly Leu Val Lys Leu Asp Val Lys Thr Lys Ser Cys
        35                  40                  45

Ser Gly Val Glu Phe Ser Thr Ser Gly Ser Ser Asn Thr Asp Thr Gly
    50                  55                  60

Lys Val Ser Gly Thr Leu Glu Thr Lys Tyr Lys Trp Cys Glu Tyr Gly
65                  70                  75                  80

Leu Thr Phe Thr Glu Lys Trp Asn Thr Asp Asn Thr Leu Gly Thr Glu
                85                  90                  95

Ile Ala Ile Glu Asp Gln Ile Cys Gln Gly Leu Lys Leu Thr Phe Asp
            100                 105                 110

Thr Thr Phe Ser Pro Asn Thr Gly Lys Lys Ser Gly Lys Ile Lys Ser
        115                 120                 125

Ala Tyr Lys Arg Glu Cys Ile Asn Leu Gly Cys Asp Val Asp Phe Asp
    130                 135                 140

Phe Ala Gly Pro Ala Ile His Gly Ser Ala Val Phe Gly Tyr Glu Gly
145                 150                 155                 160

Trp Leu Ala Gly Tyr Gln Met Thr Phe Asp Ser Ala Lys Ser Lys Leu
                165                 170                 175

Thr Arg Ser Asn Phe Ala Val Gly Tyr Arg Thr Gly Asp Phe Gln Leu
            180                 185                 190

His Thr Asn Val Asn Asn Gly Thr Glu Phe Gly Gly Ser Ile Tyr Gln
        195                 200                 205

Lys Val Cys Glu Asp Phe Asp Thr Ser Val Asn Leu Ala Trp Thr Ser
    210                 215                 220
```

```
Gly Thr Asn Cys Thr Arg Phe Gly Ile Ala Ala Lys Tyr Gln Leu Asp
225                 230                 235                 240

Pro Thr Ala Ser Ile Ser Ala Lys Val Asn Asn Ser Ser Leu Ile Gly
                245                 250                 255

Val Gly Tyr Thr Gln Thr Leu Arg Pro Gly Val Lys Leu Thr Leu Ser
            260                 265                 270

Ala Leu Val Asp Gly Lys Ser Phe Asn Ala Gly Gly His Lys Leu Gly
        275                 280                 285

Leu Ala Leu Glu Leu Glu Ala
    290             295

<210> SEQ ID NO 26
<211> LENGTH: 283
<212> TYPE: PRT
<213> ORGANISM: MUS MUSCULUS
<300> PUBLICATION INFORMATION:
<308> DATABASE ACCESSION NUMBER: NP_035826
<309> DATABASE ENTRY DATE: 2005-12-11
<313> RELEVANT RESIDUES IN SEQ ID NO: (1)..(283)

<400> SEQUENCE: 26

Met Cys Asn Thr Pro Thr Tyr Cys Asp Leu Gly Lys Ala Ala Lys Asp
1               5                   10                  15

Val Phe Asn Lys Gly Tyr Gly Phe Gly Met Val Lys Ile Asp Leu Lys
            20                  25                  30

Thr Lys Ser Cys Ser Gly Val Glu Phe Ser Thr Ser Gly His Ala Tyr
        35                  40                  45

Thr Asp Thr Gly Lys Ala Ser Gly Asn Leu Glu Thr Lys Tyr Lys Val
    50                  55                  60

Cys Asn Tyr Gly Leu Thr Phe Thr Gln Lys Trp Asn Thr Asp Asn Thr
65                  70                  75                  80

Leu Gly Thr Glu Ile Ser Trp Glu Asn Lys Leu Ala Glu Gly Leu Lys
                85                  90                  95

Leu Thr Leu Asp Thr Ile Phe Val Pro Asn Thr Gly Lys Lys Ser Gly
            100                 105                 110

Lys Leu Lys Ala Ser Tyr Arg Arg Asp Cys Phe Ser Leu Gly Ser Asn
        115                 120                 125

Val Asp Ile Asp Phe Ser Gly Pro Thr Ile Tyr Gly Trp Ala Val Leu
    130                 135                 140

Ala Phe Glu Gly Trp Leu Ala Gly Tyr Gln Met Ser Phe Asp Thr Ala
145                 150                 155                 160

Lys Ser Lys Leu Ser Gln Asn Asn Phe Ala Leu Gly Tyr Lys Ala Ala
                165                 170                 175

Asp Phe Gln Leu His Thr His Val Asn Asp Gly Thr Glu Phe Gly Gly
            180                 185                 190

Ser Ile Tyr Gln Lys Val Asn Glu Arg Ile Glu Thr Ser Ile Asn Leu
        195                 200                 205

Ala Trp Thr Ala Gly Ser Asn Asn Thr Arg Phe Gly Ile Ala Ala Lys
    210                 215                 220

Tyr Lys Leu Asp Cys Arg Thr Ser Leu Ser Ala Lys Val Asn Asn Ala
225                 230                 235                 240

Ser Leu Ile Gly Leu Gly Tyr Thr Gln Thr Leu Arg Pro Gly Val Lys
                245                 250                 255

Leu Thr Leu Ser Ala Leu Ile Asp Gly Lys Asn Phe Asn Ala Gly Gly
            260                 265                 270

His Lys Val Gly Leu Gly Phe Glu Leu Glu Ala
        275                 280
```

-continued

```
                275                 280

<210> SEQ ID NO 27
<211> LENGTH: 283
<212> TYPE: PRT
<213> ORGANISM: RATTUS NORVEGICUS
<300> PUBLICATION INFORMATION:
<308> DATABASE ACCESSION NUMBER: NP_112643
<309> DATABASE ENTRY DATE: 2005-10-17
<313> RELEVANT RESIDUES IN SEQ ID NO: (1)..(283)

<400> SEQUENCE: 27

Met Ala Val Pro Pro Thr Tyr Ala Asp Leu Gly Lys Ser Ala Arg Asp
1               5                   10                  15

Val Phe Thr Lys Gly Tyr Gly Phe Gly Leu Ile Lys Leu Asp Leu Lys
            20                  25                  30

Thr Lys Ser Glu Asn Gly Leu Glu Phe Thr Ser Ser Gly Ser Ala Asn
        35                  40                  45

Thr Glu Thr Thr Lys Val Asn Gly Ser Leu Glu Thr Lys Tyr Arg Trp
    50                  55                  60

Thr Glu Tyr Gly Leu Thr Phe Thr Glu Lys Trp Asn Thr Asp Asn Thr
65                  70                  75                  80

Leu Gly Thr Glu Ile Thr Val Glu Asp Gln Leu Ala Arg Gly Leu Lys
                85                  90                  95

Leu Thr Phe Asp Ser Ser Phe Ser Pro Asn Thr Gly Lys Lys Asn Ala
            100                 105                 110

Lys Ile Lys Thr Gly Tyr Lys Arg Glu His Ile Asn Leu Gly Cys Asp
        115                 120                 125

Val Asp Phe Asp Ile Ala Gly Pro Ser Ile Arg Gly Ala Leu Val Leu
    130                 135                 140

Gly Tyr Glu Gly Trp Leu Ala Gly Tyr Gln Met Asn Phe Glu Thr Ser
145                 150                 155                 160

Lys Ser Arg Val Thr Gln Ser Asn Phe Ala Val Gly Tyr Lys Thr Asp
                165                 170                 175

Glu Phe Gln Leu His Thr Asn Val Asn Asp Gly Thr Glu Phe Gly Gly
            180                 185                 190

Ser Ile Tyr Gln Lys Val Asn Lys Lys Leu Glu Thr Ala Val Asn Leu
        195                 200                 205

Ala Trp Thr Ala Gly Asn Ser Asn Thr Arg Phe Gly Ile Ala Ala Lys
    210                 215                 220

Tyr Gln Val Asp Pro Asp Ala Cys Phe Ser Ala Lys Val Asn Asn Ser
225                 230                 235                 240

Ser Leu Ile Gly Leu Gly Tyr Thr Gln Thr Leu Lys Pro Gly Ile Lys
                245                 250                 255

Leu Thr Leu Ser Ala Leu Leu Asp Gly Lys Asn Val Asn Ala Gly Gly
            260                 265                 270

His Lys Leu Gly Leu Gly Leu Glu Phe Gln Ala
        275                 280

<210> SEQ ID NO 28
<211> LENGTH: 295
<212> TYPE: PRT
<213> ORGANISM: RATTUS NORVEGICUS
<300> PUBLICATION INFORMATION:
<308> DATABASE ACCESSION NUMBER: NP_112644
<309> DATABASE ENTRY DATE: 2005-04-20
<313> RELEVANT RESIDUES IN SEQ ID NO: (1)..(295)

<400> SEQUENCE: 28
```

```
Met Ala Glu Cys Cys Val Pro Val Cys Gln Arg Pro Ile Cys Ile Pro
1               5                   10                  15

Pro Pro Tyr Ala Asp Leu Gly Lys Ala Arg Asp Ile Phe Asn Lys
            20                  25                  30

Gly Phe Gly Phe Gly Leu Val Lys Leu Asp Val Lys Thr Lys Ser Cys
            35                  40                  45

Ser Gly Val Glu Phe Ser Thr Ser Gly Ser Ser Asn Thr Asp Thr Gly
50                  55                  60

Lys Val Ser Gly Thr Leu Glu Thr Lys Tyr Lys Trp Cys Glu Tyr Gly
65                  70                  75                  80

Leu Thr Phe Thr Glu Lys Trp Asn Thr Asp Asn Thr Leu Gly Thr Glu
                85                  90                  95

Ile Ala Ile Glu Asp Gln Ile Cys Gln Gly Leu Lys Leu Thr Phe Asp
                100                 105                 110

Thr Thr Phe Ser Pro Asn Thr Gly Lys Lys Ser Gly Lys Ile Lys Ser
            115                 120                 125

Ala Tyr Lys Arg Glu Cys Ile Asn Leu Gly Cys Asp Val Asp Phe Asp
            130                 135                 140

Phe Ala Gly Pro Ala Ile His Gly Ser Ala Val Phe Gly Tyr Glu Gly
145                 150                 155                 160

Trp Leu Ala Gly Tyr Gln Met Thr Phe Asp Ser Ala Lys Ser Lys Leu
                165                 170                 175

Thr Arg Ser Asn Phe Ala Val Gly Tyr Arg Thr Gly Asp Phe Gln Leu
                180                 185                 190

His Thr Asn Val Asn Gly Thr Glu Phe Gly Gly Ser Ile Tyr Gln
                195                 200                 205

Lys Val Cys Glu Asp Phe Asp Thr Ser Val Asn Leu Ala Trp Thr Ser
210                 215                 220

Gly Thr Asn Cys Thr Arg Phe Gly Ile Ala Ala Lys Tyr Gln Leu Asp
225                 230                 235                 240

Pro Thr Ala Ser Ile Ser Ala Lys Val Asn Asn Ser Ser Leu Ile Gly
            245                 250                 255

Val Gly Tyr Thr Gln Thr Leu Arg Pro Gly Val Lys Leu Thr Leu Ser
            260                 265                 270

Ala Leu Val Asp Gly Lys Ser Phe Asn Ala Gly Gly His Lys Leu Gly
            275                 280                 285

Leu Ala Leu Glu Leu Glu Ala
            290                 295

<210> SEQ ID NO 29
<211> LENGTH: 283
<212> TYPE: PRT
<213> ORGANISM: RATTUS NORVEGICUS
<300> PUBLICATION INFORMATION:
<308> DATABASE ACCESSION NUMBER: NP_112645
<309> DATABASE ENTRY DATE: 2005-04-20
<313> RELEVANT RESIDUES IN SEQ ID NO: (1)..(283)

<400> SEQUENCE: 29

Met Cys Ser Thr Pro Thr Tyr Cys Asp Leu Gly Lys Ala Ala Lys Asp
1               5                   10                  15

Val Phe Asn Lys Gly Tyr Gly Phe Gly Met Val Lys Ile Asp Leu Lys
            20                  25                  30

Thr Lys Ser Cys Ser Gly Val Glu Phe Ser Thr Ser Gly His Ala Tyr
            35                  40                  45

Thr Asp Thr Gly Lys Ala Ser Gly Asn Leu Glu Thr Lys Tyr Lys Val
50                  55                  60
```

| | | | | | | | | | | | | | | | |
|---|---|---|---|---|---|---|---|---|---|---|---|---|---|---|---|
|Cys|Asn|Tyr|Gly|Leu|Ile|Phe|Thr|Gln|Lys|Trp|Asn|Thr|Asp|Asn|Thr|
|65| | | |70| | | |75| | | |80| | | |

| | | | | | | | | | | | | | | | |
|---|---|---|---|---|---|---|---|---|---|---|---|---|---|---|---|
|Leu|Gly|Thr|Glu|Ile|Ser|Trp|Glu|Asn|Lys|Leu|Ala|Glu|Gly|Leu|Lys|
| | | | |85| | | |90| | | |95| | | |

| | | | | | | | | | | | | | | | |
|---|---|---|---|---|---|---|---|---|---|---|---|---|---|---|---|
|Leu|Thr|Val|Asp|Thr|Ile|Phe|Val|Pro|Asn|Thr|Gly|Lys|Lys|Ser|Gly|
| | | |100| | | |105| | | |110| | | | |

| | | | | | | | | | | | | | | | |
|---|---|---|---|---|---|---|---|---|---|---|---|---|---|---|---|
|Lys|Leu|Lys|Ala|Ser|Tyr|Arg|Arg|Asp|Cys|Phe|Ser|Val|Gly|Ser|Lys|
| | |115| | | |120| | | |125| | | | | |

| | | | | | | | | | | | | | | | |
|---|---|---|---|---|---|---|---|---|---|---|---|---|---|---|---|
|Val|Asp|Ile|Asp|Phe|Ser|Gly|Pro|Thr|Ile|Tyr|Gly|Trp|Ala|Val|Leu|
| |130| | | |135| | | |140| | | | | | |

| | | | | | | | | | | | | | | | |
|---|---|---|---|---|---|---|---|---|---|---|---|---|---|---|---|
|Ala|Phe|Glu|Gly|Trp|Leu|Ala|Gly|Tyr|Gln|Met|Ser|Phe|Asp|Thr|Ala|
|145| | | |150| | | |155| | | |160| | | |

| | | | | | | | | | | | | | | | |
|---|---|---|---|---|---|---|---|---|---|---|---|---|---|---|---|
|Lys|Ser|Lys|Leu|Cys|Gln|Asn|Asn|Phe|Ala|Leu|Gly|Tyr|Lys|Ala|Glu|
| | | |165| | | |170| | | |175| | | | |

| | | | | | | | | | | | | | | | |
|---|---|---|---|---|---|---|---|---|---|---|---|---|---|---|---|
|Asp|Phe|Gln|Leu|His|Thr|His|Val|Asn|Asp|Gly|Thr|Glu|Phe|Gly|Gly|
| | |180| | | |185| | | |190| | | | | |

| | | | | | | | | | | | | | | | |
|---|---|---|---|---|---|---|---|---|---|---|---|---|---|---|---|
|Ser|Ile|Tyr|Gln|Arg|Val|Asn|Glu|Lys|Ile|Glu|Thr|Ser|Ile|Asn|Leu|
| |195| | | |200| | | |205| | | | | | |

| | | | | | | | | | | | | | | | |
|---|---|---|---|---|---|---|---|---|---|---|---|---|---|---|---|
|Ala|Trp|Thr|Ala|Gly|Ser|Asn|Asn|Thr|Arg|Phe|Gly|Ile|Ala|Ala|Lys|
|210| | | |215| | | |220| | | | | | | |

| | | | | | | | | | | | | | | | |
|---|---|---|---|---|---|---|---|---|---|---|---|---|---|---|---|
|Tyr|Arg|Leu|Asp|Cys|Arg|Thr|Ser|Leu|Ser|Ala|Lys|Val|Asn|Asn|Ala|
|225| | | |230| | | |235| | | |240| | | |

| | | | | | | | | | | | | | | | |
|---|---|---|---|---|---|---|---|---|---|---|---|---|---|---|---|
|Ser|Leu|Ile|Gly|Leu|Gly|Tyr|Thr|Gln|Ser|Leu|Arg|Pro|Gly|Val|Lys|
| | | |245| | | |250| | | |255| | | | |

| | | | | | | | | | | | | | | | |
|---|---|---|---|---|---|---|---|---|---|---|---|---|---|---|---|
|Leu|Thr|Leu|Ser|Ala|Leu|Val|Asp|Gly|Lys|Asn|Phe|Asn|Ala|Gly|Gly|
| | |260| | | |265| | | |270| | | | | |

| | | | | | | | |
|---|---|---|---|---|---|---|---|
|His|Lys|Val|Gly|Leu|Gly|Phe|Glu|Leu|Glu|Ala|
| |275| | | |280| | | | | |

<210> SEQ ID NO 30
<211> LENGTH: 852
<212> TYPE: DNA
<213> ORGANISM: Homo sapiens
<300> PUBLICATION INFORMATION:
<308> DATABASE ACCESSION NUMBER: NM_003374
<309> DATABASE ENTRY DATE: 2005-12-24
<313> RELEVANT RESIDUES IN SEQ ID NO: (1)..(852)

<400> SEQUENCE: 30

```
atggctgtgc acccacgta tgccgatctt ggcaaatctg ccaggdatgt cttcaccaag      60
ggctatggat ttggcttaat aaagcttgat ttgaaaacaa atctgagaa tggattggaa     120
tttacaagct caggctcagc caacactgag accaccaaag tgacgggcag tctggaaacc     180
aagtacagat ggactgagta cggcctgacg tttacagaga atggaatac cgacaataca     240
ctaggcaccg agattactgt ggaagatcag cttgcacgtg actgaagct gaccttcgat     300
tcatccttct cacctaacac tgggaaaaaa atgctaaaa tcaagacagg gtacaagcgg     360
gagcacatta acctgggctg cgacatggat ttcgacattg ctgggccttc catccgggt     420
gctctggtgc taggttacga gggctggctg ccggctacc agatgaattt tgagactgca     480
aaatcccgag tgacccagag caactttgca gttggctaca agactgatga attccagctt     540
cacactaatg tgaatgacgg gacagagttt ggcggctcca tttaccagaa agtgaacaag     600
aagttggaga ccgctgtcaa tcttgcctgg acagcaggaa acagtaacac gcgcttcgga     660
atagcagcca agtatcagat tgaccctgac gcctgcttct cggctaaagt gaacaactcc     720
agcctgatag gtttaggata cactcagact ctaaagccag gtattaaact gacactgtca     780
```

```
gctcttctgg atggcaagaa cgtcaatgct ggtggccaca agcttggtct aggactggaa    840
tttcaagcat aa                                                        852
```

<210> SEQ ID NO 31
<211> LENGTH: 885
<212> TYPE: DNA
<213> ORGANISM: Homo sapiens
<300> PUBLICATION INFORMATION:
<308> DATABASE ACCESSION NUMBER: NM_003375 18-OCT-2005
<309> DATABASE ENTRY DATE: 2005-10-18
<313> RELEVANT RESIDUES IN SEQ ID NO: (1)..(885)

<400> SEQUENCE: 31

```
atggcgaccc acggacagac ttgcgcgcgt ccaatgtgta ttcctccatc atatgctgac     60
cttggcaaag ctgccagaga tattttcaac aaaggatttg gttttgggtt ggtgaaactg    120
gatgtgaaaa caaagtcttg cagtggcgtg gaattttcaa cgtccggttc atctaataca    180
gacactggta agttactgga gaccttggag accaaataca gtggtgtgga gtatggtctg    240
actttcacag aaaagtggaa cactgataac actctgggaa cagaaatcgc aattgaagac    300
cagatttgtc aaggtttgaa actgacattt gatactacct tctcaccaaa cacaggaaag    360
aaaagtggta aaatcaagtc ttccttacaag agggagtgta taaaccttgg ttgtgatgtt    420
gactttgatt ttgctggacc tgcaatccat ggttcagctg tctttggtta tgagggctgg    480
cttgctggct accagatgac ctttgacagt gccaatcaa agctgacaag gataactttt     540
gcagtgggct acaggactgg ggacttccag ctacacacta tgtcaacga tgggacagaa    600 tttggaggat caatttatca gaaagtttgt gaagatcttg acacttcagt aaaccttgct    660
tggacatcag gtaccaactg cactcgtttt ggcattgcag ctaaatatca gttggatccc    720
actgcttcca tttctgcaaa agtcaacaac tctagcttaa ttggagtagg ctatactcag    780
actctgaggc ctggtgtgaa gcttacactc tctgctctgg tagatgggaa gagcattaat    840
gctggaggcc acaaggttgg gctcgccctg gagttggagg cttaa                   885
```

<210> SEQ ID NO 32
<211> LENGTH: 852
<212> TYPE: DNA
<213> ORGANISM: Homo sapiens
<300> PUBLICATION INFORMATION:
<308> DATABASE ACCESSION NUMBER: NM_005662
<309> DATABASE ENTRY DATE: 2005-10-17
<313> RELEVANT RESIDUES IN SEQ ID NO: (1)..(852)

<400> SEQUENCE: 32

```
atgtgtaaca caccaacgta ctgtgaccta ggaaaggctg ctaaggatgt cttcaacaaa     60
ggatatggct ttggcatggt caagatagac ctgaaaacca agtcttgtag tggagtggaa    120
ttttctactt ctggtcatgc ttacactgat acagggaaag catcaggcaa cctagaaacc    180
aaatataagg tctgtaacta tggacttacc ttcacccaga aatggaacac agacaatact    240
ctagggacag aaatctcttg ggagaataag ttggctgaag ggttgaaact gactcttgat    300
accatatttg taccgaacac aggaaagaag agtgggaaat tgaaggcctc ctataaacgg    360
gattgtttta gtgttggcag taatgttgat atagattttt ctggaccaac catctatggc    420
tgggctgtgt tggccttcga agggtggctt gctggctatc agatgagttt tgacacagcc    480
aaatccaaac tgtcacagaa taatttcgcc ctgggttaca aggctgcgga cttccagctg    540
cacacacatg tgaacgatgg cactgaattt ggaggttcta tctaccgaaa ggtgaatgag    600
aagattgaaa catccataaa ccttgcttgg acagctggga gtaacaacac ccgttttggc    660
```

| | |
|---|---|
| attgctgcta agtacatgct ggattgtaga acttctctct ctgctaaagt aaataatgcc | 720 |
| agcctgattg gactgggtta tactcagacc cttcgaccag gagtcaaatt gactttatca | 780 |
| gctttaatcg atgggaagaa cttcagtgca ggaggtcaca aggttggctt gggatttgaa | 840 |
| ctggaagctt aa | 852 |

<210> SEQ ID NO 33
<211> LENGTH: 852
<212> TYPE: DNA
<213> ORGANISM: MUS MUSCULUS
<300> PUBLICATION INFORMATION:
<308> DATABASE ACCESSION NUMBER: NM_011694
<309> DATABASE ENTRY DATE: 2005-12-11
<313> RELEVANT RESIDUES IN SEQ ID NO: (1)..(852)

<400> SEQUENCE: 33

| | |
|---|---|
| atggccgtgc ctcccacata cgccgatctt ggcaagtccg ccagggatgt cttcaccaag | 60 |
| ggctacggct ttggcttaat aaaacttgat ttgaaaacga agtcagagaa tggattggaa | 120 |
| tttaccagct caggctctgc caacacggaa accaccaaag tgaacggcag cctggaaacc | 180 |
| aagtacagat ggactgagta tgggctgacg tttacagaga agtggaacac agacaacacc | 240 |
| ctgggcactg agatcactgt ggaagaccag cttgctcgtg gactgaagct cacctttgat | 300 |
| tcgtcattct cgccgaacac tgggaaaaaa aatgctaaaa tcaagacagg gtacaagagg | 360 |
| gagcacatca acctcggctg tgacgtggac tttgacatcg ctgggccctc gatccggggc | 420 |
| gctctggtgc ttggctatga gggttggctg gctggctacc agatgaattt tgagacctcg | 480 |
| aagtcccgag tgacccagag caacttcgca gttggctata agacggatga attccagctt | 540 |
| catactaatg tgaatgacgg gacagagttt ggtggctcca tttaccagaa ggtgaacaag | 600 |
| aagttggaga ctgctgtcaa tctcgcctgg actgcaggaa acagtaacac tcgcttcgga | 660 |
| atagcagcca gtatcaggt cgaccctgat gcctgctttt cggccaaagt gaacaactct | 720 |
| agcctgattg gcttagggta cactcagacc ctaaaaccag gtatcaaact gacgttgtca | 780 |
| gccctgctcg atggcaagaa cgtcaatgcg ggtggccaca gcttggcct aggactggaa | 840 |
| tttcaagcat aa | 852 |

<210> SEQ ID NO 34
<211> LENGTH: 888
<212> TYPE: DNA
<213> ORGANISM: MUS MUSCULUS
<300> PUBLICATION INFORMATION:
<308> DATABASE ACCESSION NUMBER: NM_011695 11-DEC-2005
<309> DATABASE ENTRY DATE: 2005-12-11
<313> RELEVANT RESIDUES IN SEQ ID NO: (1)..(888)

<400> SEQUENCE: 34

| | |
|---|---|
| atggctgagt gctgtgtacc ggtatgccca cggccgatgt gtatccctcc accctatgct | 60 |
| gacctcggca aagctgccag agacattttc aacaaggat ttggctttgg gctggtgaag | 120 |
| ctggatgtga agacgaagtc atgcagcggt gtggaatttt caacatctgg ctcatctaat | 180 |
| acagacactg gtaaagttag cgggaccttg gagaccaagt acaaatggtg tgagtatggt | 240 |
| ctgactttca cagagaagtg gaacaccgat aacactctgg ggacagagat tgcaattgaa | 300 |
| gaccagattt gtcaaggttt gaactgact tttgacacca ccttttcacc gaacacagga | 360 |
| aagaaaagtg gtaaaatcaa gtctgcttac aagagggagt gtataaacct cggctgtgat | 420 |
| gttgactttg atttgctgg acctgccatc catggggtcag ctgtctttgg ttacgagggc | 480 |
| tggcttgctg ggtaccaaat gaccttgac agtgccaagt caaagctgac aaggagtaac | 540 |

```
tttgcagtcg gctacaggac tgggaacttc cagctacaca caaatgtaaa taatgggaca      600
gaatttggag gatcaattta tcagaaagta tgtgaagatt ttgacacttc agtaaacctc      660
gcttggacat caggtaccaa ctgcactcgt tttggcattg cagctaaata ccagttggat      720
cctactgctt ctatctctgc aaaggtcaac aactctagtt taattggagt gggctatact      780
cagactctga ggcctggtgt gaagcttaca ctgtctgctc tggtagacgg aagagcttt       840 aatgctggag gccacaaact tgggcttgcc ttggaattgg aggcttaa                   888

<210> SEQ ID NO 35
<211> LENGTH: 852
<212> TYPE: DNA
<213> ORGANISM: MUS MUSCULUS

<400> SEQUENCE: 35
atgtgtaaca caccaactta ttgcgaccta ggaaaggctg ccaaggatgt ctttaacaaa       60
gggtatgggt ttggcatggt caagatagat ctgaaaacca gtcttgtag tggagtggaa      120 ttttctactt caggtcatgc ttatactgat acagggaaag catcaggcaa cctagagacc      180
aaatataagg tctgcaacta tgggctcacc ttcacccaaa gtggaataca agacaatact      240
cttgggacag aaatctcttg ggagaataag ttggctgaag ggttgaaact gactcttgat      300
accatatttg taccaaacac aggaaagaag agtgggaaat taaaggcctc ctatagacgg      360
gattgtttta gtctcggcag taatgttgat atagattttt ctggaccgac catctatggc      420
tgggctgtgt tggcctttga aggttggctt gctggctatc agatgagttt tgacacagcc      480
aaatccaaac tgtctcagaa taatttcgct cttggttaca aggctgcaga cttccagctg      540
catactcacg tgaatgatgg cactgagttt ggaggctcaa tctaccagaa agttaacgag      600
aggattgaaa cgtcaataaa cctggcatgg acagctggca gcaacaacac tcgttttggc      660
atcgctgcta aatataagct ggattgtaga acttctctat ctgccaaagt aaacaatgcc      720
agtttaattg gactgggtta tacgcagacc ctccgaccag gagtcaaact gaccctgtca      780
gctttaatag atggaaagaa cttcaatgca ggaggccaca aggttggatt gggatttgaa      840
ctggaggctt ag                                                         852

<210> SEQ ID NO 36
<211> LENGTH: 852
<212> TYPE: DNA
<213> ORGANISM: RATTUS NORVEGICUS
<300> PUBLICATION INFORMATION:
<308> DATABASE ACCESSION NUMBER: NM_031353
<309> DATABASE ENTRY DATE: 2005-10-17
<313> RELEVANT RESIDUES IN SEQ ID NO: (1)..(852)

<400> SEQUENCE: 36
atggctgtgc ctcccacata tgctgatctt ggcaagtccg ccaggatgt cttcaccaag        60 ggctacggct ttggcttaat aaaacttgat ttgaaaacga agtccgagaa tggattggaa      120
tttactagct caggttctgc caacacggag accaccaaag tgaacggcag tctggaaacc      180
aagtacagat ggaccgagta tgggctgacg tttactgaga agtggaacac agacaacacc      240
ctgggcactg agatcaccgt ggaagaccag cttgctcgtg gactgaagct gacctttgat      300
tcatctttct cgcctaacac tgggaaaaaa aatgctaaaa tcaagacagg gtacaagagg      360
gagcatatca acctgggctg tgatgtggac tttgacatcg ctgggccctc aatccggggc      420
gctctgctgc ttggctatga gggttggctg gctggctacc agatgaattt tgagacctcg      480
aagtcccgag tgacccagag caactttgca gttggctaca agacggacga attccagctt      540
```

```
catactaatg tgaatgatgg gacggagttt ggtggctcca tttaccagaa ggtgaacaag    600
aagttggaga ctgctgtcaa tctcgcctgg accgcaggaa acagtaacac tcgctttgga    660
atagcagcca agtatcaggt cgaccctgat gcctgctttt cggccaaagt gaacaactcc    720
agtctaattg gcttagggta cactcagacc ctaaaaccag gtatcaaact gacactgtca    780
gccctgctgg atgcaagaa cgtcaatgcg ggtggccaca agcttggttt aggactggaa    840
tttcaagcat aa                                                         852
```

<210> SEQ ID NO 37
<211> LENGTH: 888
<212> TYPE: DNA
<213> ORGANISM: RATTUS NORVEGICUS
<300> PUBLICATION INFORMATION:
<308> DATABASE ACCESSION NUMBER: NM_031354
<309> DATABASE ENTRY DATE: 2005-04-20
<313> RELEVANT RESIDUES IN SEQ ID NO: (1)..(888)

<400> SEQUENCE: 37

```
atggctgaat gttgtgtacc ggtatgccaa cggccaattt gtatccctcc accctatgct     60
gaccttggca aagctgccag agatattttc aacaaaggat tggttttggg ttggtaaag   120 ctggatgtga aaacgaagtc atgcagtggt gtggaatttt caacatctgg ctcatctaat   180
acagacactg gtaaagtcag tgggaccttg agaccaagt acaaatggtg tgagtatggt   240
ctgactttca cagagaaatg gaacactgac aacactctgg ggacggagat tgcaattgaa   300
gaccagattt gtcaaggttt gaaactgacc tttgacacca cgttttcacc aaacacagga   360
aagaaaagtg gtaaaatcaa gtctgcttac aagagggaat gtataaacct tggctgtgat   420
gttgattttg attttgctgg acctgccatc catgggtcag ccgtctttgg ttacgagggc   480
tggcttgctg ggtaccagat gacctttgac agtgccaagt caaagctgac aaggagtaac   540
ttcgcagttg gctacaggac tggggacttc agctacaca caaatgtaaa taatgggaca   600
gaatttggag gatcaattta tcagaaagta tgtgaagatt ttgacacttc agtaaacctt   660
gcttggacat caggtaccaa ctgcactcgt tttggcattg cagctaaata ccagttggac   720
cccactgctt ctatttctgc aaaggtcaac aactctagtt taattggagt gggctatact   780
cagactctga ggcctggtgt gaagcttaca ctgtctgctc tggtagacgg aagagctttt   840
aatgctggag gccacaaact tgggcttgcc ttggaattgg aggcttaa                 888
```

<210> SEQ ID NO 38
<211> LENGTH: 852
<212> TYPE: DNA
<213> ORGANISM: RATTUS NORVEGICUS
<300> PUBLICATION INFORMATION:
<308> DATABASE ACCESSION NUMBER: NM_031355
<309> DATABASE ENTRY DATE: 2005-04-20
<313> RELEVANT RESIDUES IN SEQ ID NO: (1)..(852)

<400> SEQUENCE: 38

```
atgtgtagca caccaactta ctgcgaccta ggaaaggctg ccaaggatgt ctttaacaaa     60
gggtatgggt ttggcatggt caaaatagat ctgaaaacca agtcttgtag tggagtggaa   120
ttttctactt ctggtcatgc ttatactgat acagggaaag catcaggcaa cctagagacc   180
aaatataagg tctgtaacta cggctcatc ttcacccaaa agtggaatac agacaatact    240
cttgggacag aaatctcttg ggagaataag ttggctgaag ggttgaaact gacggttgat   300
accatatttg taccaaacac agggaagaag agtgggaaat taaggcctc ctatagacgg   360 gattgtttta gtgtgggcag taaggttgac atagattttt ctggaccgac catctatggc   420
```

-continued

```
tgggccgtgt tggcctttga aggttggctt gctggctacc agatgagttt tgacacagcc    480
aaatccaaac tgtgtcagaa taattttgct cttggttaca aggctgaaga cttccaactg    540
catactcatg taaacgatgg cactgaattt ggaggctcca tctaccagag agttaatgag    600
aagatcgaaa catcaataaa cctggcatgg acagctggca gcaacaacac tcgttttggc    660
atcgctgcta gtataggct ggattgtaga acttctctgt ctgccaaagt aaacaatgcc    720
agtttaattg gactgggtta tacgcagagt ctccgaccgg gagtcaaact gaccctgtca    780
gctttagtgg atggaaagaa cttcaatgca ggaggccaca aggttggctt gggatttgaa    840
ctggaagctt aa                                                         852
```

<210> SEQ ID NO 39
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 39

Met Arg Gln Ile Lys Ile Trp Phe Gln Asn Arg Arg Met Lys Trp Lys
1               5                   10                  15

Lys

<210> SEQ ID NO 40
<211> LENGTH: 51
<212> TYPE: DNA
<213> ORGANISM: Artificial Sequence
<220> FEATURE:
<223> OTHER INFORMATION: NUCLEOTIDE SEQUENCE CORRESPONDING TO SYNTHETIC
      PEPTIDE

<400> SEQUENCE: 40
atgcgtcaga ttaaaatttg gtttcagaat cgtcgtatga aatggaaaaa a              51

<210> SEQ ID NO 41
<211> LENGTH: 5
<212> TYPE: PRT
<213> ORGANISM: Artificial Sequence
<220> FEATURE:
<223> OTHER INFORMATION: SYNTHETIC PEPTIDE

<400> SEQUENCE: 41

Ser Trp Thr Trp Glu
1               5

<210> SEQ ID NO 42
<211> LENGTH: 5
<212> TYPE: PRT
<213> ORGANISM: Artificial Sequence
<220> FEATURE:
<223> OTHER INFORMATION: SYNTHETIC PEPTIDE

<400> SEQUENCE: 42

Lys Trp Thr Trp Lys
1               5

<210> SEQ ID NO 43
<211> LENGTH: 283
<212> TYPE: PRT
<213> ORGANISM: homo sapiens
<220> FEATURE:
<221> NAME/KEY: VARIANT
<222> LOCATION: (72)..(72)
<223> OTHER INFORMATION: E72Q SUBSTITUTION

<400> SEQUENCE: 43

```
Met Ala Val Pro Pro Thr Tyr Ala Asp Leu Gly Lys Ser Ala Arg Asp
1               5                   10                  15
Val Phe Thr Lys Gly Tyr Gly Phe Gly Leu Ile Lys Leu Asp Leu Lys
            20                  25                  30
Thr Lys Ser Glu Asn Gly Leu Glu Phe Thr Ser Ser Gly Ser Ala Asn
        35                  40                  45
Thr Glu Thr Thr Lys Val Thr Gly Ser Leu Glu Thr Lys Tyr Arg Trp
50                  55                  60
Thr Glu Tyr Gly Leu Thr Phe Thr Gln Lys Trp Asn Thr Asp Asn Thr
65                  70                  75                  80
Leu Gly Thr Glu Ile Thr Val Glu Asp Gln Leu Ala Arg Gly Leu Lys
                85                  90                  95
Leu Thr Phe Asp Ser Ser Phe Ser Pro Asn Thr Gly Lys Lys Asn Ala
            100                 105                 110
Lys Ile Lys Thr Gly Tyr Lys Arg Glu His Ile Asn Leu Gly Cys Asp
        115                 120                 125
Met Asp Phe Asp Ile Ala Gly Pro Ser Ile Arg Gly Ala Leu Val Leu
130                 135                 140
Gly Tyr Glu Gly Trp Leu Ala Gly Tyr Gln Met Asn Phe Glu Thr Ala
145                 150                 155                 160
Lys Ser Arg Val Thr Gln Ser Asn Phe Ala Val Gly Tyr Lys Thr Asp
                165                 170                 175
Glu Phe Gln Leu His Thr Asn Val Asn Asp Gly Thr Glu Phe Gly Gly
            180                 185                 190
Ser Ile Tyr Gln Lys Val Asn Lys Lys Leu Glu Thr Ala Val Asn Leu
        195                 200                 205
Ala Trp Thr Ala Gly Asn Ser Asn Thr Arg Phe Gly Ile Ala Ala Lys
210                 215                 220
Tyr Gln Ile Asp Pro Asp Ala Cys Phe Ser Ala Lys Val Asn Asn Ser
225                 230                 235                 240
Ser Leu Ile Gly Leu Gly Tyr Thr Gln Thr Leu Lys Pro Gly Ile Lys
                245                 250                 255
Leu Thr Leu Ser Ala Leu Leu Asp Gly Lys Asn Val Asn Ala Gly Gly
            260                 265                 270
His Lys Leu Gly Leu Gly Leu Glu Phe Gln Ala
        275                 280
```

<210> SEQ ID NO 44
<211> LENGTH: 283
<212> TYPE: PRT
<213> ORGANISM: homo sapiens
<220> FEATURE:
<221> NAME/KEY: VARIANT
<222> LOCATION: (87)..(87)
<223> OTHER INFORMATION: E87Q SUBSTITUTION
<220> FEATURE:
<221> NAME/KEY: VARIANT
<222> LOCATION: (88)..(88)
<223> OTHER INFORMATION: D88N SUBSTITUTION

<400> SEQUENCE: 44

```
Met Ala Val Pro Pro Thr Tyr Ala Asp Leu Gly Lys Ser Ala Arg Asp
1               5                   10                  15
Val Phe Thr Lys Gly Tyr Gly Phe Gly Leu Ile Lys Leu Asp Leu Lys
            20                  25                  30
Thr Lys Ser Glu Asn Gly Leu Glu Phe Thr Ser Ser Gly Ser Ala Asn
```

```
                35                  40                  45
Thr Glu Thr Thr Lys Val Thr Gly Ser Leu Glu Thr Lys Tyr Arg Trp
 50                  55                  60

Thr Glu Tyr Gly Leu Thr Phe Thr Glu Lys Trp Asn Thr Asp Asn Thr
 65                  70                  75                  80

Leu Gly Thr Glu Ile Thr Val Gln Asn Gln Leu Ala Arg Gly Leu Lys
                     85                  90                  95

Leu Thr Phe Asp Ser Ser Phe Ser Pro Asn Thr Gly Lys Lys Asn Ala
                    100                 105                 110

Lys Ile Lys Thr Gly Tyr Lys Arg Glu His Ile Asn Leu Gly Cys Asp
            115                 120                 125

Met Asp Phe Asp Ile Ala Gly Pro Ser Ile Arg Gly Ala Leu Val Leu
    130                 135                 140

Gly Tyr Glu Gly Trp Leu Ala Gly Tyr Gln Met Asn Phe Glu Thr Ala
145                 150                 155                 160

Lys Ser Arg Val Thr Gln Ser Asn Phe Ala Val Gly Tyr Lys Thr Asp
                    165                 170                 175

Glu Phe Gln Leu His Thr Asn Val Asn Asp Gly Thr Glu Phe Gly Gly
                180                 185                 190

Ser Ile Tyr Gln Lys Val Asn Lys Lys Leu Glu Thr Ala Val Asn Leu
            195                 200                 205

Ala Trp Thr Ala Gly Asn Ser Asn Thr Arg Phe Gly Ile Ala Ala Lys
    210                 215                 220

Tyr Gln Ile Asp Pro Asp Ala Cys Phe Ser Ala Lys Val Asn Asn Ser
225                 230                 235                 240

Ser Leu Ile Gly Leu Gly Tyr Thr Gln Thr Leu Lys Pro Gly Ile Lys
                    245                 250                 255

Leu Thr Leu Ser Ala Leu Leu Asp Gly Lys Asn Val Asn Ala Gly Gly
                260                 265                 270

His Lys Leu Gly Leu Gly Leu Glu Phe Gln Ala
            275                 280

<210> SEQ ID NO 45
<211> LENGTH: 283
<212> TYPE: PRT
<213> ORGANISM: homo sapiens
<220> FEATURE:
<221> NAME/KEY: VARIANT
<222> LOCATION: (65)..(65)
<223> OTHER INFORMATION: E65Q SUBSTITUTION

<400> SEQUENCE: 45

Met Ala Val Pro Pro Thr Tyr Ala Asp Leu Gly Lys Ser Ala Arg Asp
 1               5                  10                  15

Val Phe Thr Lys Gly Tyr Gly Phe Gly Leu Ile Lys Leu Asp Leu Lys
                20                  25                  30

Thr Lys Ser Glu Asn Gly Leu Glu Phe Thr Ser Ser Gly Ser Ala Asn
            35                  40                  45

Thr Glu Thr Thr Lys Val Thr Gly Ser Leu Glu Thr Lys Tyr Arg Trp
 50                  55                  60

Thr Gln Tyr Gly Leu Thr Phe Thr Glu Lys Trp Asn Thr Asp Asn Thr
 65                  70                  75                  80

Leu Gly Thr Glu Ile Thr Val Glu Asp Gln Leu Ala Arg Gly Leu Lys
                     85                  90                  95

Leu Thr Phe Asp Ser Ser Phe Ser Pro Asn Thr Gly Lys Lys Asn Ala
                    100                 105                 110
```

```
Lys Ile Lys Thr Gly Tyr Lys Arg Glu His Ile Asn Leu Gly Cys Asp
        115                 120                 125

Met Asp Phe Asp Ile Ala Gly Pro Ser Ile Arg Gly Ala Leu Val Leu
    130                 135                 140

Gly Tyr Glu Gly Trp Leu Ala Gly Tyr Gln Met Asn Phe Glu Thr Ala
145                 150                 155                 160

Lys Ser Arg Val Thr Gln Ser Asn Phe Ala Val Gly Tyr Lys Thr Asp
                165                 170                 175

Glu Phe Gln Leu His Thr Asn Val Asn Asp Gly Thr Glu Phe Gly Gly
            180                 185                 190

Ser Ile Tyr Gln Lys Val Asn Lys Leu Glu Thr Ala Val Asn Leu
            195                 200                 205

Ala Trp Thr Ala Gly Asn Ser Asn Thr Arg Phe Gly Ile Ala Ala Lys
    210                 215                 220

Tyr Gln Ile Asp Pro Asp Ala Cys Phe Ser Ala Lys Val Asn Asn Ser
225                 230                 235                 240

Ser Leu Ile Gly Leu Gly Tyr Thr Gln Thr Leu Lys Pro Gly Ile Lys
                245                 250                 255

Leu Thr Leu Ser Ala Leu Leu Asp Gly Lys Asn Val Asn Ala Gly Gly
            260                 265                 270

His Lys Leu Gly Leu Gly Leu Glu Phe Gln Ala
        275                 280

<210> SEQ ID NO 46
<211> LENGTH: 283
<212> TYPE: PRT
<213> ORGANISM: homo sapiens
<220> FEATURE:
<221> NAME/KEY: VARIANT
<222> LOCATION: (73)..(73)
<223> OTHER INFORMATION: K73L SUBSTITUTION

<400> SEQUENCE: 46

Met Ala Val Pro Pro Thr Tyr Ala Asp Leu Gly Lys Ser Ala Arg Asp
1               5                   10                  15

Val Phe Thr Lys Gly Tyr Gly Phe Gly Leu Ile Lys Leu Asp Leu Lys
                20                  25                  30

Thr Lys Ser Glu Asn Gly Leu Glu Phe Thr Ser Ser Gly Ser Ala Asn
            35                  40                  45

Thr Glu Thr Thr Lys Val Thr Gly Ser Leu Glu Thr Lys Tyr Arg Trp
        50                  55                  60

Thr Glu Tyr Gly Leu Thr Phe Thr Glu Leu Trp Asn Thr Asp Asn Thr
65                  70                  75                  80

Leu Gly Thr Glu Ile Thr Val Glu Asp Gln Leu Ala Arg Gly Leu Lys
                85                  90                  95

Leu Thr Phe Asp Ser Ser Phe Ser Pro Asn Thr Gly Lys Lys Asn Ala
            100                 105                 110

Lys Ile Lys Thr Gly Tyr Lys Arg Glu His Ile Asn Leu Gly Cys Asp
        115                 120                 125

Met Asp Phe Asp Ile Ala Gly Pro Ser Ile Arg Gly Ala Leu Val Leu
    130                 135                 140

Gly Tyr Glu Gly Trp Leu Ala Gly Tyr Gln Met Asn Phe Glu Thr Ala
145                 150                 155                 160

Lys Ser Arg Val Thr Gln Ser Asn Phe Ala Val Gly Tyr Lys Thr Asp
                165                 170                 175

Glu Phe Gln Leu His Thr Asn Val Asn Asp Gly Thr Glu Phe Gly Gly
            180                 185                 190
```

Ser Ile Tyr Gln Lys Val Asn Lys Leu Glu Thr Ala Val Asn Leu
            195                 200                 205

Ala Trp Thr Ala Gly Asn Ser Asn Thr Arg Phe Gly Ile Ala Ala Lys
        210                 215                 220

Tyr Gln Ile Asp Pro Asp Ala Cys Phe Ser Ala Lys Val Asn Asn Ser
225                 230                 235                 240

Ser Leu Ile Gly Leu Gly Tyr Thr Gln Thr Leu Lys Pro Gly Ile Lys
            245                 250                 255

Leu Thr Leu Ser Ala Leu Leu Asp Gly Lys Asn Val Asn Ala Gly Gly
        260                 265                 270

His Lys Leu Gly Leu Gly Leu Glu Phe Gln Ala
            275                 280

<210> SEQ ID NO 47
<211> LENGTH: 283
<212> TYPE: PRT
<213> ORGANISM: homo sapiens
<220> FEATURE:
<221> NAME/KEY: VARIANT
<222> LOCATION: (77)..(77)
<223> OTHER INFORMATION: D77N SUBSTITUTION

<400> SEQUENCE: 47

Met Ala Val Pro Pro Thr Tyr Ala Asp Leu Gly Lys Ser Ala Arg Asp
1               5                   10                  15

Val Phe Thr Lys Gly Tyr Gly Phe Gly Leu Ile Lys Leu Asp Leu Lys
            20                  25                  30

Thr Lys Ser Glu Asn Gly Leu Glu Phe Thr Ser Ser Gly Ser Ala Asn
        35                  40                  45

Thr Glu Thr Thr Lys Val Thr Gly Ser Leu Glu Thr Lys Tyr Arg Trp
50                  55                  60

Thr Glu Tyr Gly Leu Thr Phe Thr Glu Lys Trp Asn Thr Asn Asn Thr
65                  70                  75                  80

Leu Gly Thr Glu Ile Thr Val Glu Asp Gln Leu Ala Arg Gly Leu Lys
            85                  90                  95

Leu Thr Phe Asp Ser Ser Phe Ser Pro Asn Thr Gly Lys Lys Asn Ala
        100                 105                 110

Lys Ile Lys Thr Gly Tyr Lys Arg Glu His Ile Asn Leu Gly Cys Asp
        115                 120                 125

Met Asp Phe Asp Ile Ala Gly Pro Ser Ile Arg Gly Ala Leu Val Leu
130                 135                 140

Gly Tyr Glu Gly Trp Leu Ala Gly Tyr Gln Met Asn Phe Glu Thr Ala
145                 150                 155                 160

Lys Ser Arg Val Thr Gln Ser Asn Phe Ala Val Gly Tyr Lys Thr Asp
            165                 170                 175

Glu Phe Gln Leu His Thr Asn Val Asn Asp Gly Thr Glu Phe Gly Gly
        180                 185                 190

Ser Ile Tyr Gln Lys Val Asn Lys Leu Glu Thr Ala Val Asn Leu
            195                 200                 205

Ala Trp Thr Ala Gly Asn Ser Asn Thr Arg Phe Gly Ile Ala Ala Lys
        210                 215                 220

Tyr Gln Ile Asp Pro Asp Ala Cys Phe Ser Ala Lys Val Asn Asn Ser
225                 230                 235                 240

Ser Leu Ile Gly Leu Gly Tyr Thr Gln Thr Leu Lys Pro Gly Ile Lys
            245                 250                 255

Leu Thr Leu Ser Ala Leu Leu Asp Gly Lys Asn Val Asn Ala Gly Gly

-continued

```
                  260                 265                 270

His Lys Leu Gly Leu Gly Leu Glu Phe Gln Ala
    275                 280

<210> SEQ ID NO 48
<211> LENGTH: 283
<212> TYPE: PRT
<213> ORGANISM: homo sapiens
<220> FEATURE:
<221> NAME/KEY: VARIANT
<222> LOCATION: (202)..(202)
<223> OTHER INFORMATION: E202Q SUBSTITUTION

<400> SEQUENCE: 48

Met Ala Val Pro Pro Thr Tyr Ala Asp Leu Gly Lys Ser Ala Arg Asp
1               5                   10                  15

Val Phe Thr Lys Gly Tyr Gly Phe Gly Leu Ile Lys Leu Asp Leu Lys
            20                  25                  30

Thr Lys Ser Glu Asn Gly Leu Glu Phe Thr Ser Ser Gly Ser Ala Asn
        35                  40                  45

Thr Glu Thr Thr Lys Val Thr Gly Ser Leu Glu Thr Lys Tyr Arg Trp
50                  55                  60

Thr Glu Tyr Gly Leu Thr Phe Thr Glu Lys Trp Asn Thr Asp Asn Thr
65                  70                  75                  80

Leu Gly Thr Glu Ile Thr Val Glu Asp Gln Leu Ala Arg Gly Leu Lys
            85                  90                  95

Leu Thr Phe Asp Ser Ser Phe Ser Pro Asn Thr Gly Lys Lys Asn Ala
        100                 105                 110

Lys Ile Lys Thr Gly Tyr Lys Arg Glu His Ile Asn Leu Gly Cys Asp
    115                 120                 125

Met Asp Phe Asp Ile Ala Gly Pro Ser Ile Arg Gly Ala Leu Val Leu
130                 135                 140

Gly Tyr Glu Gly Trp Leu Ala Gly Tyr Gln Met Asn Phe Glu Thr Ala
145                 150                 155                 160

Lys Ser Arg Val Thr Gln Ser Asn Phe Ala Val Gly Tyr Lys Thr Asp
            165                 170                 175

Glu Phe Gln Leu His Thr Asn Val Asn Asp Gly Thr Glu Phe Gly Gly
        180                 185                 190

Ser Ile Tyr Gln Lys Val Asn Lys Lys Leu Gln Thr Ala Val Asn Leu
    195                 200                 205

Ala Trp Thr Ala Gly Asn Ser Asn Thr Arg Phe Gly Ile Ala Ala Lys
210                 215                 220

Tyr Gln Ile Asp Pro Asp Ala Cys Phe Ser Ala Lys Val Asn Asn Ser
225                 230                 235                 240

Ser Leu Ile Gly Leu Gly Tyr Thr Gln Thr Leu Lys Pro Gly Ile Lys
            245                 250                 255

Leu Thr Leu Ser Ala Leu Leu Asp Gly Lys Asn Val Asn Ala Gly Gly
        260                 265                 270

His Lys Leu Gly Leu Gly Leu Glu Phe Gln Ala
    275                 280

<210> SEQ ID NO 49
<211> LENGTH: 283
<212> TYPE: PRT
<213> ORGANISM: homo sapiens
<220> FEATURE:
<221> NAME/KEY: VARIANT
<222> LOCATION: (75)..(75)
<223> OTHER INFORMATION: N75A SUBSTITUTION
```

```
<400> SEQUENCE: 49

Met Ala Val Pro Pro Thr Tyr Ala Asp Leu Gly Lys Ser Ala Arg Asp
1               5                   10                  15

Val Phe Thr Lys Gly Tyr Gly Phe Gly Leu Ile Lys Leu Asp Leu Lys
            20                  25                  30

Thr Lys Ser Glu Asn Gly Leu Glu Phe Thr Ser Ser Gly Ser Ala Asn
        35                  40                  45

Thr Glu Thr Thr Lys Val Thr Gly Ser Leu Glu Thr Lys Tyr Arg Trp
50                  55                  60

Thr Glu Tyr Gly Leu Thr Phe Thr Glu Lys Trp Ala Thr Asp Asn Thr
65                  70                  75                  80

Leu Gly Thr Glu Ile Thr Val Glu Asp Gln Leu Ala Arg Gly Leu Lys
                85                  90                  95

Leu Thr Phe Asp Ser Ser Phe Ser Pro Asn Thr Gly Lys Lys Asn Ala
            100                 105                 110

Lys Ile Lys Thr Gly Tyr Lys Arg Glu His Ile Asn Leu Gly Cys Asp
        115                 120                 125

Met Asp Phe Asp Ile Ala Gly Pro Ser Ile Arg Gly Ala Leu Val Leu
130                 135                 140

Gly Tyr Glu Gly Trp Leu Ala Gly Tyr Gln Met Asn Phe Glu Thr Ala
145                 150                 155                 160

Lys Ser Arg Val Thr Gln Ser Asn Phe Ala Val Gly Tyr Lys Thr Asp
                165                 170                 175

Glu Phe Gln Leu His Thr Asn Val Asn Asp Gly Thr Glu Phe Gly Gly
            180                 185                 190

Ser Ile Tyr Gln Lys Val Asn Lys Lys Leu Glu Thr Ala Val Asn Leu
        195                 200                 205

Ala Trp Thr Ala Gly Asn Ser Asn Thr Arg Phe Gly Ile Ala Ala Lys
210                 215                 220

Tyr Gln Ile Asp Pro Asp Ala Cys Phe Ser Ala Lys Val Asn Asn Ser
225                 230                 235                 240

Ser Leu Ile Gly Leu Gly Tyr Thr Gln Thr Leu Lys Pro Gly Ile Lys
                245                 250                 255

Leu Thr Leu Ser Ala Leu Leu Asp Gly Lys Asn Val Asn Ala Gly Gly
            260                 265                 270

His Lys Leu Gly Leu Gly Leu Glu Phe Gln Ala
        275                 280

<210> SEQ ID NO 50
<211> LENGTH: 283
<212> TYPE: PRT
<213> ORGANISM: homo sapiens
<220> FEATURE:
<221> NAME/KEY: VARIANT
<222> LOCATION: (67)..(67)
<223> OTHER INFORMATION: G67A SUBSTITUTION

<400> SEQUENCE: 50

Met Ala Val Pro Pro Thr Tyr Ala Asp Leu Gly Lys Ser Ala Arg Asp
1               5                   10                  15

Val Phe Thr Lys Gly Tyr Gly Phe Gly Leu Ile Lys Leu Asp Leu Lys
            20                  25                  30

Thr Lys Ser Glu Asn Gly Leu Glu Phe Thr Ser Ser Gly Ser Ala Asn
        35                  40                  45

Thr Glu Thr Thr Lys Val Thr Gly Ser Leu Glu Thr Lys Tyr Arg Trp
50                  55                  60
```

```
Thr Glu Tyr Ala Leu Thr Phe Thr Glu Lys Trp Asn Thr Asp Asn Thr
 65                  70                  75                  80

Leu Gly Thr Glu Ile Thr Val Glu Asp Gln Leu Ala Arg Gly Leu Lys
                 85                  90                  95

Leu Thr Phe Asp Ser Ser Phe Ser Pro Asn Thr Gly Lys Lys Asn Ala
            100                 105                 110

Lys Ile Lys Thr Gly Tyr Lys Arg Glu His Ile Asn Leu Gly Cys Asp
        115                 120                 125

Met Asp Phe Asp Ile Ala Gly Pro Ser Ile Arg Gly Ala Leu Val Leu
130                 135                 140

Gly Tyr Glu Gly Trp Leu Ala Gly Tyr Gln Met Asn Phe Glu Thr Ala
145                 150                 155                 160

Lys Ser Arg Val Thr Gln Ser Asn Phe Ala Val Gly Tyr Lys Thr Asp
                165                 170                 175

Glu Phe Gln Leu His Thr Asn Val Asn Asp Gly Thr Glu Phe Gly Gly
            180                 185                 190

Ser Ile Tyr Gln Lys Val Asn Lys Lys Leu Glu Thr Ala Val Asn Leu
        195                 200                 205

Ala Trp Thr Ala Gly Asn Ser Asn Thr Arg Phe Gly Ile Ala Ala Lys
210                 215                 220

Tyr Gln Ile Asp Pro Asp Ala Cys Phe Ser Ala Lys Val Asn Asn Ser
225                 230                 235                 240

Ser Leu Ile Gly Leu Gly Tyr Thr Gln Thr Leu Lys Pro Gly Ile Lys
                245                 250                 255

Leu Thr Leu Ser Ala Leu Leu Asp Gly Lys Asn Val Asn Ala Gly Gly
            260                 265                 270

His Lys Leu Gly Leu Gly Leu Glu Phe Gln Ala
        275                 280

<210> SEQ ID NO 51
<211> LENGTH: 852
<212> TYPE: DNA
<213> ORGANISM: homo sapiens
<220> FEATURE:
<221> NAME/KEY: mutation
<222> LOCATION: (215)..(215)
<223> OTHER INFORMATION: G>C

<400> SEQUENCE: 51
atggctgtgc acccacgta tgccgatctt ggcaaatctg ccagggatgt cttcaccaag      60
ggctatggat ttggcttaat aaagcttgat ttgaaaacaa atctgagaa tggattggaa     120 tttacaagct caggctcagc caacactgag accaccaaag tgacgggcag tctggaaacc     180
aagtacagat ggactgagta cggcctgacg tttacagaga atggaatac cgacaataca     240 ctaggcaccg agattactgt ggaagatcag cttgcacgtg gactgaagct gaccttcgat     300
tcatccttct cacctaacac tgggaaaaaa atgctaaaa tcaagacagg gtacaagcgg     360
gagcacatta acctgggctg cgacatggat ttcgacattg ctgggccttc catccggggt     420
gctctggtgc taggttacga gggctggctg gccggctacc agatgaattt tgagactgca     480
aaatcccgag tgacccagag caactttgca gttggctaca agactgatga attccagctt     540
cacactaatg tgaatgacgg gacagagttt ggcggctcca tttaccagaa agtgaacaag     600
aagttggaga ccgctgtcaa tcttgcctgg acagcaggaa acagtaacac gcgcttcgga     660
atagcagcca agtatcagat tgaccctgac gcctgcttct cggctaaagt gaacaactcc     720
agcctgatag gtttaggata cactcagact ctaaagccag gtattaaact gacactgtca     780
```

```
gctcttctgg atggcaagaa cgtcaatgct ggtggccaca agcttggtct aggactggaa    840
tttcaagcat aa                                                        852

<210> SEQ ID NO 52
<211> LENGTH: 852
<212> TYPE: DNA
<213> ORGANISM: homo sapiens
<220> FEATURE:
<221> NAME/KEY: mutation
<222> LOCATION: (261)..(261)
<223> OTHER INFORMATION: G>C
<220> FEATURE:
<221> NAME/KEY: mutation
<222> LOCATION: (264)..(264)
<223> OTHER INFORMATION: G>A

<400> SEQUENCE: 52
atggctgtgc cacccacgta tgccgatctt ggcaaatctg ccaggatgt cttcaccaag      60 ggctatggat ttggcttaat aaagcttgat ttgaaaacaa atctgagaa tggattggaa     120 tttacaagct caggctcagc caacactgag accaccaaag tgacgggcag tctggaaacc    180
aagtacagat ggactgagta cggcctgacg tttacacaga atggaatac cgacaataca    240 ctaggcaccg agattactgt gcaaaatcag cttgcacgtg gactgaagct gaccttcgat    300
tcatccttct cacctaacac tgggaaaaaa aatgctaaaa tcaagacagg gtacaagcgg    360
gagcacatta acctgggctg cgacatggat ttcgacattg ctgggccttc catccggggt    420
gctctggtgc taggttacga gggctggctg gccggctacc agatgaattt tgagactgca    480
aaatcccgag tgacccagag caactttgca gttggctaca agactgatga attccagctt    540
cacactaatg tgaatgacgg gacagagttt ggcggctcca tttaccagaa agtgaacaag    600
aagttggaga ccgctgtcaa tcttgcctgg acagcaggaa acagtaacac gcgcttcgga    660
atagcagcca gtatcagat tgaccctgac gcctgcttct cggctaaagt gaacaactcc    720
agcctgatag gtttaggata cactcagact ctaaagccag gtattaaact gacactgtca    780
gctcttctgg atggcaagaa cgtcaatgct ggtggccaca agcttggtct aggactggaa    840
tttcaagcat aa                                                        852

<210> SEQ ID NO 53
<211> LENGTH: 852
<212> TYPE: DNA
<213> ORGANISM: homo sapiens
<220> FEATURE:
<221> NAME/KEY: mutation
<222> LOCATION: (196)..(196)
<223> OTHER INFORMATION: G>C

<400> SEQUENCE: 53
atggctgtgc cacccacgta tgccgatctt ggcaaatctg ccaggatgt cttcaccaag      60 ggctatggat ttggcttaat aaagcttgat ttgaaaacaa atctgagaa tggattggaa     120 tttacaagct caggctcagc caacactgag accaccaaag tgacgggcag tctggaaacc    180
aagtacagat ggactcagta cggcctgacg tttacagaga atggaatac cgacaataca    240 ctaggcaccg agattactgt ggaagatcag cttgcacgtg gactgaagct gaccttcgat    300
tcatccttct cacctaacac tgggaaaaaa aatgctaaaa tcaagacagg gtacaagcgg    360
gagcacatta acctgggctg cgacatggat ttcgacattg ctgggccttc catccggggt    420
gctctggtgc taggttacga gggctggctg gccggctacc agatgaattt tgagactgca    480
aaatcccgag tgacccagag caactttgca gttggctaca agactgatga attccagctt    540
```

| cacactaatg tgaatgacgg dacagagttt ggcggctcca tttaccagaa agtgaacaag | 600 |
| aagttggaga ccgctgtcaa tcttgcctgg acagcaggaa acagtaacac gcgcttcgga | 660 |
| atagcagcca agtatcagat tgaccctgac gcctgcttct cggctaaagt gaacaactcc | 720 |
| agcctgatag gtttaggata cactcagact ctaaagccag gtattaaact gacactgtca | 780 |
| gctcttctgg atggcaagaa cgtcaatgct ggtggccaca agcttggtct aggactggaa | 840 |
| tttcaagcat aa | 852 |

<210> SEQ ID NO 54
<211> LENGTH: 852
<212> TYPE: DNA
<213> ORGANISM: homo sapiens
<220> FEATURE:
<221> NAME/KEY: mutation
<222> LOCATION: (219)..(220)
<223> OTHER INFORMATION: AA>TT

<400> SEQUENCE: 54

| atggctgtgc cacccacgta tgccgatctt ggcaaatctg ccagggatgt cttcaccaag | 60 |
| ggctatggat ttggcttaat aaagcttgat ttgaaaacaa atctgagaa tggattggaa | 120 |
| tttacaagct caggctcagc caacactgag accaccaaag tgacgggcag tctggaaacc | 180 |
| aagtacagat ggactgagta cggcctgacg tttacagagt tatggaatac cgacaataca | 240 |
| ctaggcaccg agattactgt ggaagatcag cttgcacgtg gactgaagct gaccttcgat | 300 |
| tcatccttct cacctaacac tgggaaaaaa aatgctaaaa tcaagacagg gtacaagcgg | 360 |
| gagcacatta acctgggctg cgacatggat ttcgacattg ctgggccttc catccggggt | 420 |
| gctctggtgc taggttacga gggctggctg gccggctacc agatgaattt tgagactgca | 480 |
| aaatcccgag tgacccagag caactttgca gttggctaca agactgatga attccagctt | 540 |
| cacactaatg tgaatgacgg dacagagttt ggcggctcca tttaccagaa agtgaacaag | 600 |
| aagttggaga ccgctgtcaa tcttgcctgg acagcaggaa acagtaacac gcgcttcgga | 660 |
| atagcagcca agtatcagat tgaccctgac gcctgcttct cggctaaagt gaacaactcc | 720 |
| agcctgatag gtttaggata cactcagact ctaaagccag gtattaaact gacactgtca | 780 |
| gctcttctgg atggcaagaa cgtcaatgct ggtggccaca agcttggtct aggactggaa | 840 |
| tttcaagcat aa | 852 |

<210> SEQ ID NO 55
<211> LENGTH: 852
<212> TYPE: DNA
<213> ORGANISM: homo sapiens
<220> FEATURE:
<221> NAME/KEY: mutation
<222> LOCATION: (232)..(232)
<223> OTHER INFORMATION: G>A

<400> SEQUENCE: 55

| atggctgtgc cacccacgta tgccgatctt ggcaaatctg ccagggatgt cttcaccaag | 60 |
| ggctatggat ttggcttaat aaagcttgat ttgaaaacaa atctgagaa tggattggaa | 120 |
| tttacaagct caggctcagc caacactgag accaccaaag tgacgggcag tctggaaacc | 180 |
| aagtacagat ggactgagta cggcctgacg tttacagaga atggaatac caacaataca | 240 |
| ctaggcaccg agattactgt ggaagatcag cttgcacgtg gactgaagct gaccttcgat | 300 |
| tcatccttct cacctaacac tgggaaaaaa aatgctaaaa tcaagacagg gtacaagcgg | 360 |
| gagcacatta acctgggctg cgacatggat ttcgacattg ctgggccttc catccggggt | 420 |

```
gctctggtgc taggttacga gggctggctg gccggctacc agatgaattt tgagactgca    480
aaatcccgag tgacccagag caactttgca gttggctaca agactgatga attccagctt    540
cacactaatg tgaatgacgg gacagagttt ggcggctcca tttaccagaa agtgaacaag    600
aagttggaga ccgctgtcaa tcttgcctgg acagcaggaa acagtaacac gcgcttcgga    660
atagcagcca agtatcagat tgaccctgac gcctgcttct cggctaaagt gaacaactcc    720
agcctgatag gtttaggata cactcagact ctaaagccag gtattaaact gacactgtca    780
gctcttctgg atggcaagaa cgtcaatgct ggtggccaca gcttggtct aggactggaa    840 tttcaagcat aa                                                       852

<210> SEQ ID NO 56
<211> LENGTH: 852
<212> TYPE: DNA
<213> ORGANISM: homo sapiens
<220> FEATURE:
<221> NAME/KEY: mutation
<222> LOCATION: (605)..(605)
<223> OTHER INFORMATION: G>C

<400> SEQUENCE: 56
atggctgtgc cacccacgta tgccgatctt ggcaaatctg ccagggatgt cttcaccaag     60
ggctatggat ttggcttaat aaagcttgat ttgaaaacaa atctgagaa tggattggaa    120 tttacaagct caggctcagc caacactgag accaccaaag tgacgggcag tctggaaacc    180
aagtacagat ggactgagta cggcctgacg tttacagaga atggaatac cgacaataca    240 ctaggcaccg agattactgt ggaagatcag cttgcacgtg gactgaagct gaccttcgat    300
tcatccttct cacctaacac tgggaaaaaa aatgctaaaa tcaagacagg gtacaagcgg    360
gagcacatta acctgggctg cgacatggat ttcgacattg ctgggccttc catccggggt    420
gctctggtgc taggttacga gggctggctg gccggctacc agatgaattt tgagactgca    480
aaatcccgag tgacccagag caactttgca gttggctaca agactgatga attccagctt    540
cacactaatg tgaatgacgg gacagagttt ggcggctcca tttaccagaa agtgaacaag    600
aagttgcaga ccgctgtcaa tcttgcctgg acagcaggaa acagtaacac gcgcttcgga    660
atagcagcca agtatcagat tgaccctgac gcctgcttct cggctaaagt gaacaactcc    720
agcctgatag gtttaggata cactcagact ctaaagccag gtattaaact gacactgtca    780
gctcttctgg atggcaagaa cgtcaatgct ggtggccaca gcttggtct aggactggaa    840 tttcaagcat aa                                                       852

<210> SEQ ID NO 57
<211> LENGTH: 852
<212> TYPE: DNA
<213> ORGANISM: homo sapiens
<220> FEATURE:
<221> NAME/KEY: mutation
<222> LOCATION: (176)..(177)
<223> OTHER INFORMATION: AA>GC

<400> SEQUENCE: 57
atggctgtgc cacccacgta tgccgatctt ggcaaatctg ccagggatgt cttcaccaag     60
ggctatggat ttggcttaat aaagcttgat ttgaaaacaa atctgagaa tggattggaa    120 tttacaagct caggctcagc caacactgag accaccaaag tgacgggcag tctgggcacc    180
aagtacagat ggactgagta cggcctgacg tttacagaga atggaatac cgacaataca    240 ctaggcaccg agattactgt ggaagatcag cttgcacgtg gactgaagct gaccttcgat    300
```

-continued

| | |
|---|---|
| tcatccttct cacctaacac tgggaaaaaa aatgctaaaa tcaagacagg gtacaagcgg | 360 |
| gagcacatta acctgggctg cgacatggat ttcgacattg ctgggccttc catccggggt | 420 |
| gctctggtgc taggttacga gggctggctg gccggctacc agatgaattt tgagactgca | 480 |
| aaatcccgag tgacccagag caactttgca gttggctaca agactgatga attccagctt | 540 |
| cacactaatg tgaatgacgg gacagagttt ggcggctcca tttaccagaa agtgaacaag | 600 |
| aagttggaga ccgctgtcaa tcttgcctgg acagcaggaa acagtaacac gcgcttcgga | 660 |
| atagcagcca agtatcagat tgaccctgac gcctgcttct cggctaaagt gaacaactcc | 720 |
| agcctgatag gtttaggata cactcagact ctaaagccag gtattaaact gacactgtca | 780 |
| gctcttctgg atggcaagaa cgtcaatgct ggtggccaca gcttggtct aggactggaa | 840 |
| tttcaagcat aa | 852 |

<210> SEQ ID NO 58
<211> LENGTH: 852
<212> TYPE: DNA
<213> ORGANISM: homo sapiens
<220> FEATURE:
<221> NAME/KEY: mutation
<222> LOCATION: (203)..(203)
<223> OTHER INFORMATION: G>C

<400> SEQUENCE: 58

| | |
|---|---|
| atggctgtgc cacccacgta tgccgatctt ggcaaatctg ccaggatgt cttccaccaag | 60 |
| ggctatggat ttggcttaat aaagcttgat ttgaaaacaa atctgagaa tggattggaa | 120 |
| tttacaagct caggctcagc caacactgag accaccaaag tgacgggcag tctggaaacc | 180 |
| aagtacagat ggactgagta cgccctgacg tttacagaga atggaatac cgacaataca | 240 |
| ctaggcaccg agattactgt ggaagatcag cttgcacgtg gactgaagct gaccttcgat | 300 |
| tcatccttct cacctaacac tgggaaaaaa aatgctaaaa tcaagacagg gtacaagcgg | 360 |
| gagcacatta acctgggctg cgacatggat ttcgacattg ctgggccttc catccggggt | 420 |
| gctctggtgc taggttacga gggctggctg gccggctacc agatgaattt tgagactgca | 480 |
| aaatcccgag tgacccagag caactttgca gttggctaca agactgatga attccagctt | 540 |
| cacactaatg tgaatgacgg gacagagttt ggcggctcca tttaccagaa agtgaacaag | 600 |
| aagttggaga ccgctgtcaa tcttgcctgg acagcaggaa acagtaacac gcgcttcgga | 660 |
| atagcagcca agtatcagat tgaccctgac gcctgcttct cggctaaagt gaacaactcc | 720 |
| agcctgatag gtttaggata cactcagact ctaaagccag gtattaaact gacactgtca | 780 |
| gctcttctgg atggcaagaa cgtcaatgct ggtggccaca gcttggtct aggactggaa | 840 |
| tttcaagcat aa | 852 |

<210> SEQ ID NO 59
<211> LENGTH: 22
<212> TYPE: DNA
<213> ORGANISM: ARTIFICIAL SEQUENCE
<220> FEATURE:
<223> OTHER INFORMATION: PRIMER

<400> SEQUENCE: 59

| | |
|---|---|
| gacgtttaca cagaagtgga ac | 22 |

<210> SEQ ID NO 60
<211> LENGTH: 22
<212> TYPE: DNA
<213> ORGANISM: ARTIFICIAL SEQUENCE

```
<220> FEATURE:
<223> OTHER INFORMATION: PRIMER

<400> SEQUENCE: 60
gttccacttc tgtgtaaacg tc                                          22

<210> SEQ ID NO 61
<211> LENGTH: 21
<212> TYPE: DNA
<213> ORGANISM: ARTIFICIAL SEQUENCE
<220> FEATURE:
<223> OTHER INFORMATION: PRIMER

<400> SEQUENCE: 61
tggactcagt atgggctgac g                                           21

<210> SEQ ID NO 62
<211> LENGTH: 20
<212> TYPE: DNA
<213> ORGANISM: ARTIFICIAL SEQUENCE
<220> FEATURE:
<223> OTHER INFORMATION: PRIMER

<400> SEQUENCE: 62
gcccatactg agtccatctg                                             20

<210> SEQ ID NO 63
<211> LENGTH: 21
<212> TYPE: DNA
<213> ORGANISM: ARTIFICIAL SEQUENCE
<220> FEATURE:
<223> OTHER INFORMATION: PRIMER

<400> SEQUENCE: 63
acagagctgt ggaacacaga c                                           21

<210> SEQ ID NO 64
<211> LENGTH: 22
<212> TYPE: DNA
<213> ORGANISM: ARTIFICIAL SEQUENCE
<220> FEATURE:
<223> OTHER INFORMATION: PRIMER

<400> SEQUENCE: 64
gttccacagc tctgtaaacg tc                                          22

<210> SEQ ID NO 65
<211> LENGTH: 21
<212> TYPE: DNA
<213> ORGANISM: ARTIFICIAL SEQUENCE
<220> FEATURE:
<223> OTHER INFORMATION: PRIMER

<400> SEQUENCE: 65
gaacacacag aacaccctgg g                                           21

<210> SEQ ID NO 66
<211> LENGTH: 23
<212> TYPE: DNA
<213> ORGANISM: ARTIFICIAL SEQUENCE
<220> FEATURE:
<223> OTHER INFORMATION: PRIMER

<400> SEQUENCE: 66
gtgttctgtg tgttccactt ctc                                         23
```

```
<210> SEQ ID NO 67
<211> LENGTH: 25
<212> TYPE: DNA
<213> ORGANISM: ARTIFICIAL SEQUENCE
<220> FEATURE:
<223> OTHER INFORMATION: PRIMER

<400> SEQUENCE: 67
gaagttgcag actgctgtca atctc                                              25

<210> SEQ ID NO 68
<211> LENGTH: 24
<212> TYPE: DNA
<213> ORGANISM: ARTIFICIAL SEQUENCE
<220> FEATURE:
<223> OTHER INFORMATION: PRIMER

<400> SEQUENCE: 68
gcgagattga cagcagtctg caac                                               24

<210> SEQ ID NO 69
<211> LENGTH: 17
<212> TYPE: DNA
<213> ORGANISM: ARTIFICIAL SEQUENCE
<220> FEATURE:
<223> OTHER INFORMATION: PRIMER

<400> SEQUENCE: 69
gaacacagac gccaccc                                                       17

<210> SEQ ID NO 70
<211> LENGTH: 16
<212> TYPE: DNA
<213> ORGANISM: ARTIFICIAL SEQUENCE
<220> FEATURE:
<223> OTHER INFORMATION: PRIMER

<400> SEQUENCE: 70
gtggcgtctg tgttcc                                                        16

<210> SEQ ID NO 71
<211> LENGTH: 23
<212> TYPE: DNA
<213> ORGANISM: ARTIFICIAL SEQUENCE
<220> FEATURE:
<223> OTHER INFORMATION: PRIMER

<400> SEQUENCE: 71
gatggactga gtatgccctg acg                                                23

<210> SEQ ID NO 72
<211> LENGTH: 24
<212> TYPE: DNA
<213> ORGANISM: ARTIFICIAL SEQUENCE
<220> FEATURE:
<223> OTHER INFORMATION: PRIMER

<400> SEQUENCE: 72
gtcagggcat actcagtcca tctg                                               24

<210> SEQ ID NO 73
<211> LENGTH: 43
<212> TYPE: PRT
<213> ORGANISM: Artificial Sequence
<220> FEATURE:
<223> OTHER INFORMATION: SYNTHETIC PEPTIDE

<400> SEQUENCE: 73
```

Met Ala Val Pro Pro Thr Tyr Ala Asp Leu Gly Lys Ser Ala Arg Asp
1               5                   10                  15

Val Phe Thr Lys Gly Tyr Gly Phe Gly Leu Met Arg Gln Ile Lys Ile
            20                  25                  30

Trp Phe Gln Asn Arg Arg Met Lys Trp Lys Lys
            35                  40

<210> SEQ ID NO 74
<211> LENGTH: 129
<212> TYPE: DNA
<213> ORGANISM: Artificial Sequence
<220> FEATURE:
<223> OTHER INFORMATION: NUCLEOTIDE SEQUENCE CORRESPONDING TO SYNTHETIC
      PEPTIDE

<400> SEQUENCE: 74
atggctgtgc cacccacgta tgccgatctt ggcaaatctg ccagggatgt cttcaccaag    60
ggctatggat ttggcttaat gcgtcagatt aaaatttggt tcagaatcg tcgtatgaaa    120 tggaaaaaa                                                           129

<210> SEQ ID NO 75
<211> LENGTH: 7
<212> TYPE: PRT
<213> ORGANISM: Artificial Sequence
<220> FEATURE:
<223> OTHER INFORMATION: SYNTHETIC PEPTIDE

<400> SEQUENCE: 75

His Ala Ile Tyr Pro Arg His
1               5

<210> SEQ ID NO 76
<211> LENGTH: 11
<212> TYPE: PRT
<213> ORGANISM: Artificial Sequence
<220> FEATURE:
<223> OTHER INFORMATION: SYNTHETIC PEPTIDE

<400> SEQUENCE: 76

Arg Lys Lys Arg Arg Gln Arg Arg Gly Gly
1               5                   10

<210> SEQ ID NO 77
<211> LENGTH: 38
<212> TYPE: PRT
<213> ORGANISM: Artificial Sequence
<220> FEATURE:
<223> OTHER INFORMATION: SYNTHETIC PEPTIDE

<400> SEQUENCE: 77

Arg Lys Lys Arg Arg Gln Arg Arg Gly Gly Ser Trp Thr Trp Glu
1               5                   10                  15

Lys Lys Leu Glu Thr Ala Val Asn Leu Ala Trp Thr Ala Gly Asn Ser
            20                  25                  30

Asn Lys Trp Thr Trp Lys
            35

<210> SEQ ID NO 78
<211> LENGTH: 34
<212> TYPE: PRT
<213> ORGANISM: Artificial Sequence
<220> FEATURE:
<223> OTHER INFORMATION: SYNTHETIC PEPTIDE

```
<400> SEQUENCE: 78

His Ala Ile Tyr Pro Arg His Ser Trp Thr Trp Glu Lys Lys Leu Glu
1               5                   10                  15

Thr Ala Val Asn Leu Ala Trp Thr Ala Gly Asn Ser Asn Lys Trp Thr
            20                  25                  30

Trp Lys
```

VDAC1 COMPOSITIONS AND METHODS OF USE THEREOF FOR REGULATING APOPTOSIS

CROSS-REFERENCE TO RELATED APPLICATIONS

The present application is a continuation in part of U.S. patent application Ser. No. 11/817,869, filed on Sep. 5, 2007, now U.S. Pat. No. 8,119,601, which is the U.S. national stage of PCT/IL2006/000311 filed on Mar. 9, 2006, which is based on and claims the benefit of U.S. Provisional Patent Application Nos. 60/736,291 filed on Nov. 15, 2005 and 60/659,876 filed on Mar. 10, 2005, the contents of each of which are expressly incorporated herein in their entireties by this reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 78,891 byte ASCII (text) file named "Seq_List" created on Feb. 15, 2012.

FIELD OF THE INVENTION

The present invention relates generally to the mitochondrial protein, voltage-dependent anion channel (VDAC), polynucleotides encoding same and variants thereof, as well as peptide fragments, peptide derivatives and analogs. In particular, the present invention is directed to VDAC1 and specific amino acid and polynucleotide sequences thereof useful in inducing or regulating apoptosis and to pharmaceutical compositions comprising same useful in the treatment of diseases associated with aberrant apoptosis.

BACKGROUND OF THE INVENTION

VDAC

Voltage-dependent anion channel (VDAC; mitochondrial porin) is a pore-forming protein found in the outer mitochondrial membrane in all eukaryotic cells controlling the fluxes of ions and metabolites between the mitochondria and the cytosol. VDAC is recognized as a key protein in mitochondria-mediated apoptosis due to its function in the release of apoptotic proteins located in the inter-membranal space and its interaction with apoptotic proteins. VDAC also serves as binding sites for several cytosolic enzymes and mitochondrial intermembranal space proteins, including hexokinase, creatine kinase and glycerol kinase.

Three mammalian isoforms of VDAC are known, VDAC1, VDAC2, VDAC3, where VDAC1 is the major isoform expressed in mammalian cells. Blachly-Dysion et al (1993) disclosed the cloning and functional expression in yeast of two human VDAC isoforms, VDAC1 and VDAC2. Human VDAC1 was shown to specifically bind hexokinase. U.S. Pat. No. 5,780,235 discloses two novel VDAC sequences, which were named HACH (Human voltage-dependent Anion CHannel), subsequently identified as VDAC2 and VDAC3. That patent provides genetically engineered expression vectors, host cells containing the vector, a method for producing HACH and a method for identifying pharmaceutical compositions inhibiting the expression and activity of HACH and for the use of such compositions for the treatment of cancer and proliferative diseases.

Apoptosis

Apoptosis, also known as programmed cell death, plays a central role in, inter alia, development, immune cell regulation and tissue homeostasis in multicellular organisms. Genetic and molecular analysis from various species has indicated that the apoptotic pathway is highly conserved. In addition to being essential for normal development and maintenance, apoptosis is important in the defense against viral infection and in preventing cancer.

Mitochondria play an important role in the regulation of apoptotic cell death. The release of apoptogenic intermediates such as cytochrome c from the intermembranal space into the cytoplasm of a cell initiates a cascade of caspase activation that executes the cell death program. Substantial evidence links VDAC to apoptosis and suggests that VDAC is a critical player in the release of apoptogenic proteins from mitochondria in mammalian cells (Shoshan-Barmatz and Gincel, 2003).

Anti-Apoptotic and Pro-Apoptotic Proteins

Diverse intrinsic cell death signals emanating from various subcellular organelles can induce the release of cytochrome c from mitochondria. The Bcl-2 family of pro- and anti-apoptotic proteins constitutes a decisive control point for apoptosis. Proteins in the Bcl-2 family are major regulators of apoptosis (reviewed in Kim, 2005). Members of this family include both pro- and anti-apoptotic proteins and share homology in up to four conserved regions termed Bcl-2 homology (BH) 1-4 domains. The family can be divided into three main sub-classes: anti-apoptotic proteins, pro-apoptotic proteins and BH3-only proteins.

The anti-apoptotic proteins, which include hexokinase-I (HK-I), Bcl-2 and Bcl-xL, share homology throughout all four BH domains. The pro-apoptotic proteins can be further subdivided and include multidomain proteins, such as Bax and Bak, which possess sequence homology in BH1-3 domains.

The more distantly related BH3-only proteins appear to be only pro-apoptotic and share sequence homology within the BH3 region, which is required for their apoptotic function. The BH3-only proteins include, for example, BID, NOXA, PUMA and BAD.

It is currently held that anti-apoptotic members of the Bcl-2 family of proteins, such as HK-I, HK-II, Bcl-2 and Bcl-xL, act to promote cell survival by interacting with VDAC. Conversely, pro-apoptotic members of the Bcl-2 family of proteins, including Bak and Bax, may interact with VDAC to promote release of cytochrome c. Because of the pivotal role that mitochondria play in apoptotic cell death, mitochondrial proteins serve as potential targets for apoptosis regulating therapies.

One major obstacle in cancer chemotherapy is inherent, or acquired, resistance, apparently due to the suppression of apoptosis. Hexokinase-I (HK-I) is an anti-apoptotic mitochondrial protein that binds to VDAC. Many tumor cells exhibit a high glycolytic rate, which is correlated with a high level of HK-I expression. It is believed that the overexpression of anti-apoptotic proteins such as HK-I in cancer cells is a self-defense mechanism of those cells and is related to the cell's resistance to chemotherapy. It would be useful to develop agents that overcome apoptosis suppression in cancer cells, including HK-I suppression.

Certain compositions related to VDAC and use thereof for either inhibiting or inducing apoptosis are known in the art. US Patent Application Publication No. 2005/0085420 discloses methods of inhibiting apoptosis by promoting formation of a BAK/VDAC2 complex, and methods of promoting apoptosis by disrupting formation of a BAK/VDAC2 complex. The VDAC2/BAK inhibitor compound is, for example, a BH3 domain peptide, a BH3 domain-only mutein, an anti-VDAC2 antibody, a VDAC2 mutein and the like.

US Patent Application Publication No. 2005/0234116 discloses small molecule compounds with utility as VDAC regulators, in particular as apoptosis suppressors.

There remains an unmet need for therapeutic agents effective in regulating apoptosis and specifically in inducing apoptosis in hyperproliferative disease and inhibiting apoptosis in neurodegenerative, cardiac and ophthalmic diseases. The art neither teaches nor suggests inducing apoptosis by expression of exogenous VDAC1 or the modulation of VDAC1 interaction with its associated proteins using VDAC1 derived peptides.

SUMMARY OF THE INVENTION

The present invention provides, for the first time, VDAC1 molecules including polypeptide variants, peptide fragments thereof and derivatives, analogs and salts thereof, their nucleotide sequences, compositions comprising same and methods useful in treating diseases and disorders associated with aberrant apoptosis.

Unexpectedly, it is now shown that expression of exogenous VDAC1 amino acid sequence modulates apoptosis. Suitable sequences include VDAC1 polypeptide, polypeptide variant or an isolated peptide, or derivative or analog thereof, comprising an amino acid sequence derived from the mitochondrial VDAC1 protein. Specifically, the ectopic or exogenous expression of a VDAC1 amino acid sequence or of peptides derived from VDAC1 causes a dramatic increase in apoptosis of human cancer cell lines and in chemo and radio-resistant cancer cells.

The present invention is based in part on the discoveries that (a) overexpression of VDAC1 polypeptide or VDAC1 polypeptide variant triggers apoptosis in cancer cell lines; (b) HK-I, an anti-apoptosis protein, protects cells against apoptosis via its interaction with VDAC1; and (c) expression of peptides derived from VDAC1 or of a VDAC1 polypeptide comprising an amino acid substitution in VDAC1 eliminates HK-I or ruthenium red (RuR) protection against staurosporine-, curcumin-, $As_2O_3$— or VDAC1 overexpression-induced apoptosis.

Accordingly, the present invention provides VDAC1 amino acid sequences, pharmaceutical compositions comprising same and methods of use thereof. In particular, the present invention provides a VDAC1 molecule selected from a VDAC1 polypeptide variant, and a VDAC1 peptide, derivative, analog or salt thereof useful for inducing apoptotic cell death in cancer cells and in particular, in chemo- and radio-therapy-resistant cells.

The principles of the present invention are exemplified in both in vitro and in vivo model systems of diseases associated with aberrant apoptosis. In various embodiments VDAC1 is selected from the group consisting of a rat VDAC1 isoform, a mouse VDAC1 isoform, a yeast VDAC1 isoform, a plant VDAC1 and a human VDAC1 isoform.

According to a first aspect, the present invention provides a VDAC1 molecule capable of modulating apoptosis in a cell, the molecule selected from: (i) an isolated VDAC1 polypeptide variant having at least one amino acid substitution in an amino acid residue residing in a VDAC1 cytosolic domain and (ii) an isolated VDAC1 peptide fragment, analog, chemical derivative and a salt thereof, wherein the peptide fragment, analog, chemical derivative and a salt thereof is derived from a VDAC1 cytosolic domain or partial sequence thereof.

In some embodiments the molecule induces apoptosis or enhances sensitivity to an apoptosis-inducing reagent. Non-limiting examples of apoptosis-inducing reagents include STS, curcumin, doxorubicin and Taxol®.

In one embodiment the VDAC1 molecule is a peptide fragment comprising an amino acid sequence of a VDAC1 cytosolic domain or comprising a partial sequence of the VDAC1 cytosolic domain.

The defenition of VDAC1 cytosolic domains is not always consistent. According to one of the propsed VDAC1 membrane topology, the cytosolic domains include the N-terminus (amino acids M1 to about D9 or to about L26) and three β-loops, β-loop 1 (from amino acid W63 to about N79) β-loop 2 (from amino acid S100 to about R119), β-loop 4 (from amino acid K199- to about N215). The β-loop 3 is exposed to the intermembrane space (from amino acid E157 to about T174). A peptide fragment derived from a cytosolic domain may include the amino acid sequence of the entire cytosolic domain or a partial sequence thereof. The peptide fragment derived from a cytosolic domain may comprise up to about 30 consecutive amino acids, up to about 25 amino acids, up to about 20 amino acids, or up to about 10 amino acid residues.

In one embodiment the VDAC1 peptide fragment comprises an amino acid sequence that modulates the interaction between VDAC1 and a mitochondrial anti-apoptotic protein. Certain mitochondrial anti-apoptotic proteins are known in the art and include hexokinase-I (HK-I), HK-II, Bcl2, Bcl2A1, Bcl2L1, Bcl2L10, Bcl2L11, Bcl2L2, Bcl-xL and Bcl-W.

In one embodiment the VDAC1 peptide of the invention comprises a VDAC1 amino acid sequence up to about 70 amino acid residues. In some embodiment the VDAC1 peptide comprises an amino acid sequence up to about 60 amino acid residues, up to about 40 amino acid residues, up to about 30 amino acid residues, and preferably from about 15 to about 30 amino acid residues.

In some embodiments the VDAC1 peptide is selected from the group of peptides having the amino acid sequence as set forth in SEQ ID NO:1, SEQ ID NO:2, SEQ ID NO:3, and SEQ ID NO:5. In certain embodiments the VDAC1 peptide comprises an amino acid sequence as set forth in SEQ ID NO:2. In other embodiments the VDAC1 peptide comprises an amino acid sequence as set forth in SEQ ID NO:1.

In some embodiments the peptide of the invention is linked to a cell penetrating peptide (CPP). In one exemplary embodiment the CPP is an amino acid sequence comprising the *Drosophila* antennapedia (ANTP) domain or a fragment thereof. In certain embodiments the VDAC peptides further comprise an ANTP amino acid sequence as set forth in SEQ ID NO:39. In one embodiment the VDAC peptide further comprises tryptophan zipper amino acid sequences and a fragment of the ANTP amino acid domain. In some embodiments the peptide is selected from the group of peptides having amino acid sequence as set forth in SEQ ID NO:11, SEQ ID NO:12, SEQ ID NO:13, SEQ ID NO:15 and SEQ ID NO:73. In one embodiment the peptide comprises an amino acid sequence as set forth in SEQ ID NO:12. In another embodiment, the peptide comprises an amino acid sequence as set forth in SEQ ID NO:73.

In other embodiments the peptide is selected from a VDAC1 peptide derivative and VDAC1 peptide analog. In one embodiment the VDAC1 peptide derivative is an amidated VDAC1 peptide.

In certain embodiments the VDAC1 molecule is selected from a VDAC1 polypeptide variant having at least one amino acid substitution in an amino acid residue residing in a VDAC1 protein domain exposed to the cytosol. The cytosolic domains of VDAC1 have been identified as the N-terminus, first, second and fourth β-loop domains of VDAC1. In one embodiment the amino acid substitution replaces a charged amino acid selected from aspartate (D), glutamate (E) and lysine (K) with a non-charged amino acid. In one embodiment the VDAC1 polypeptide variant is selected from any one of SEQ ID NO:43-SEQ ID NO:48. The VDAC1 polypeptide variant may comprise further structural changes including additional amino acid substations, amino acid deletions and additions. Accordingly the present invention provides a polypeptide variant having about 80%, about 90% about 95%, about 98% or about 99% homology to any one of SEQ ID NO:43-SEQ ID NO:48.

In another aspect, the present invention provides isolated nucleotide sequences encoding a VDAC1 polypeptide variant or peptide capable of modulating apoptosis in a cell. In one embodiment a nucleotide sequence is selected from the group consisting of the sequences set forth in any one of SEQ ID NO:6-SEQ ID NO:8, SEQ ID NO:10, SEQ ID NO:16-SEQ ID NO:18, SEQ ID NO:20 or SEQ ID NO:74. In another aspect the present invention provides a polynucleotide construct comprising a nucleic acid sequence encoding a VDAC1 polypeptide variant or peptide derivative, analog or salt thereof capable of modulating apoptosis in a cell. In one embodiment the VDAC1 polypeptide variant or peptide induces apoptosis. In some embodiments the construct comprises a nucleotide sequence selected from the group consisting of sequences set forth in any one of SEQ ID NO:6-SEQ ID NO:8, SEQ ID NO:10, SEQ ID NO:16-SEQ ID NO:18, SEQ ID NO:20 or SEQ ID NO:74.

In some embodiments the polynucleotide construct is an expression vector.

Further provided is a host cell comprising a polynucleotide construct comprising a nucleotide sequence encoding a VDAC1 polypeptide variant or peptide, derivative, analog or salt thereof capable of modulating apoptosis in a cell. In one embodiment the VDAC1 polypeptide variant or peptide, derivative, analog or salt thereof can induce apoptosis.

According to another aspect the present invention provides a pharmaceutical composition comprising a VDAC1 sequence. In one embodiment the VDAC1 sequence is an amino acid sequence selected from the group consisting of a VDAC1 polypeptide, a VDAC1 polypeptide variant, a VDAC1 peptide, derivative, analog or salt thereof and a pharmaceutically acceptable diluent or excipient. In some embodiments VDAC1 is human VDAC1. In one embodiment, the pharmaceutical composition comprises a VDAC1 peptide comprising amino acid sequence as set forth in anyone of SEQ ID NO:1-SEQ ID NO:3, SEQ ID NO:5, SEQ ID NO:11-SEQ ID NO:14, SEQ ID NO:15 and SEQ ID NO:72. In certain embodiments the VDAC1 peptide is selected from the group consisting of a peptide comprising an amino acid sequence set forth in any one of SEQ ID NO:2 and SEQ ID NO:12, encoded by a nucleotide set forth in SEQ ID NO:7 and SEQ ID NO:17, respectively. In other embodiments, the VDAC1 peptide is selected from the group consisting of a peptide comprising an amino acid sequence set forth in any one of SEQ ID NO:1 and SEQ ID NO:73, encoded by a nucleotide set forth in SEQ ID NO:6 and SEQ ID NO:74, respectively.

In one embodiment the pharmaceutical composition of the invention provides a VDAC1 amino acid sequence selected from a VDAC1 polypeptide or VDAC1 polypeptide variant. In one embodiment the polypeptide is selected from SEQ ID NO:21, SEQ ID NO:24 and SEQ ID NO:27. In one preferred embodiment the polypeptide has SEQ ID NO:21. In one embodiment the VDAC1 polypeptide variant comprises at least one amino acid substitution within a cytosolic β-loop domain of VDAC1. In one embodiment the VDAC1 polypeptide variant comprises an amino acid substitution of a charged amino acid residue. In one embodiment the VDAC1 polypeptide variant is selected from any one of SEQ ID NO:43-SEQ ID NO:48.

In one embodiment the present invention further provides a pharmaceutical composition comprising an isolated nucleic acid sequence encoding a VDAC1 polypeptide, VDAC1 polypeptide variant or a VDAC1 peptide of the invention. In one embodiment the nucleic acid has a sequence selected from SEQ ID NO:6-SEQ ID NO:8, SEQ ID NO:10, SEQ ID NO:16-SEQ ID NO:18, SEQ ID NO:20, SEQ ID NO:30, SEQ ID NO:33, SEQ ID NO:36, SEQ ID NO:51-58 and SEQ ID NO:74. The present invention further encompasses polynucleotide constructs comprising the nucleic acid sequences according to the invention and host cells comprising said constructs.

The present invention further provides a pharmaceutical composition comprising a polynucleotide construct comprising an isolated nucleic acid sequence selected from any one of SEQ ID NO:6-SEQ ID NO:8, SEQ ID NO:10, SEQ ID NO:16-SEQ ID NO:18, SEQ ID NO:20, SEQ ID NO:30-36, SEQ ID NO:51-58 and SEQ ID NO:74. In some embodiments the polynucleotide construct comprises an expression vector. In exemplary embodiments the pharmaceutical composition comprises a polynucleotide construct comprising a nucleotide sequence selected from the group consisting of SEQ ID NO:7, SEQ ID NO:17, SEQ ID NO:30 and SEQ ID NO:50.

In certain embodiments the pharmaceutical composition comprises a VDAC1 amino acid sequence according to the present invention and a shielding particle. In certain embodiments the shielding particle comprises PEI, PEG and lipids.

In certain embodiments the pharmaceutical composition comprises an encapsulated VDAC1 amino acid sequence according to the present invention. In certain embodiments the VDAC1 amino acid sequence is encapsulated into a vesicle, or into immunoliposomes.

In yet another aspect the present invention provides a method for treating a subject suffering from a disease associated with aberrant apoptosis, the method comprising administering to a subject in need thereof a composition comprising a therapeutically effective amount of an agent selected from the group consisting of a) a VDAC1 polypeptide, b) a VDAC1 polypeptide variant, c) at least one VDAC1-derived peptide, a derivative or analog of thereof and d) a VDAC1 nucleic acid encoding a VDAC1 polypeptide, VDAC1 polypeptide variant or a VDAC1-derived peptide. In some embodiments the disease is selected from cancer including chemo- and radiotherapy-resistant cancer.

In yet another aspect the present invention provides a method for inducing apoptosis in a cell or enhancing the effect of an apoptosis-inducing reagent in a cell comprising the step of upregulating VDAC1 expression in the cell under conditions sufficient to induce apoptosis of the cell.

In one embodiment upregulating VDAC1 expression comprises the step of providing an exogenous VDAC1 molecule to the cell under conditions sufficient for said VDAC1 amino acid sequence to induce apoptosis of the cell. In some embodiments the VDAC1 molecule is selected from a VDAC1 polypeptide, a VDAC1 polypeptide variant and a VDAC1 peptide, derivative analog or salt thereof according to the principles of the present invention. In other embodiments VDAC1 molecule is selected from a VDAC1 nucleotide sequence according to the principles of the present invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 3A shows leukemic U937 cells that were transformed to express green fluorescent protein (GFP) and VDAC1-GFP. FIG. 3B shows an immunoblot using anti-VDAC or anti-GFP antibodies of extracts from cell transfected with VDAC1, VDAC1-GFP, mutated E72QVDAC1 or mutated E72QVDAC1-GFP. FIGS. 3C-3D show that over-expression of recombinant HK-I protects against apoptotic cell death induced by over-expression of native, but not of E72Q or E202Q VDAC1 variants. FIG. 3E shows the results of experiments confirming that overexpression of recombinant HK-I protects cells from apoptosis induced by staurosporine (STS).

FIGS. 4A and 4B show that over-expression of recombinant HK-I protects against apoptotic cell death induced by over-expression of native and some, but not in all mutated versions of VDAC1.

FIG. 5A shows that RuR protects against apoptotic cell death induced by over-expression of native, but not of certain VDAC1 polypeptide variants. FIGS. 5B and 5C show the protective effect of RuR against apoptosis induced by exogenous expression of native and some VDAC1 variants but not of E72Q- or E65Q-VDAC1 variants. FIG. 5D shows that RuR increases the total amount of VDAC1 protein in cells expressing native mVDAC1, but not in cells expressing E72Q-mVDAC1. FIG. 5E shows that RuR inhibited recombinant native mVDAC1 channel activity and stabilized the channel in an almost completely closed state. In contrast, the channel activity of E72Q-mVDAC1 was not inhibited by RuR.

FIG. 8 shows the alignment of the polypeptide sequences of the human, mouse and rat VDAC1 (SEQ ID NOs: 21, 24 and 27, respectively, FIG. 8A), VDAC2 (SEQ ID NOs: 22, 25 and 28, respectively, FIG. 8B) and VDAC3 (SEQ ID NOs: 23, 26 and 29, respectively, FIG. 8C) isoforms and an alignment of two cytosolic β-loop domains from those sequences (FIG. 8D). It should be noted that the according to the numbering in this figure, the amino acid count includes the first methionine, therefore E72 is presented as E73, etc.

FIG. 9 is a graph depicting the LP1 peptide (SEQ ID NO:2) induced detachment of brain mitochondrial bound HK-I.

FIG. 10 are graphs showing that LP1 peptide (SEQ ID NO:2) eliminates the HK-I inhibition of the permeability transition pore (PTP) opening FIG. 10A: effect of LP1; FIG. 10B: effect of HK-I pre-incubated for 10 min with LP1.

FIG. 11 shows the cell death induced in cancer cells by peptides of the invention.

FIG. 14 demonstartes that peptide LP4-trp (SEQ ID NO:15) selectively induce cell death of cancerous cells co-expressing the cell surface markers CD19 and CD5.

FIG. 15 demonstrates that peptide LP4-trp (SEQ ID NO:15) bearing either L- or D-amino acids induce cancer cell death (FIG. 15A: U937 cells; FIG. 15B: MOLT4 cells.

DETAILED DESCRIPTION OF THE INVENTION

Figure 1A:
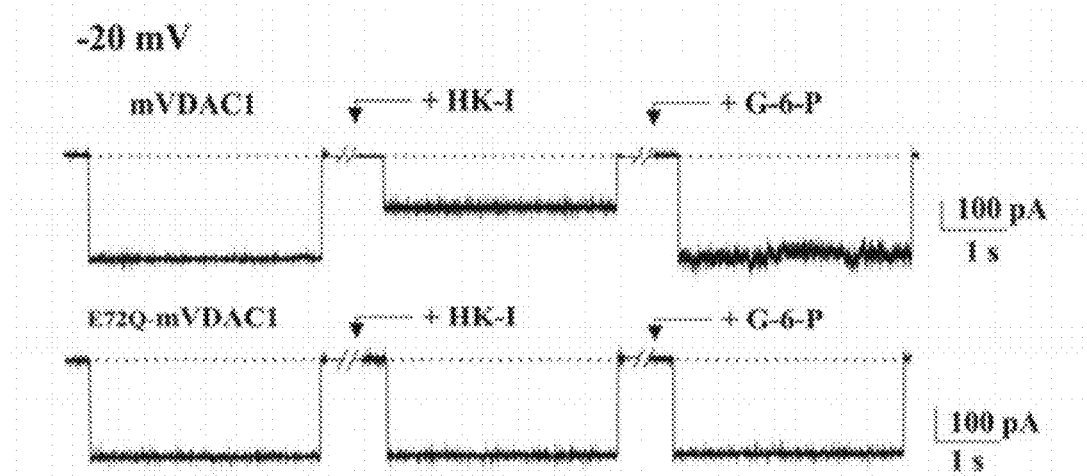
FIG. 1A shows that the interaction between HK-I and the mitochondrial VDAC1 reconstituted into a planar lipid bilayer induced decrease in the channel conductance.

The present invention relates to VDAC1 polypeptides, peptides, derivatives and analogs thereof, compositions comprising same and methods useful for modulating apoptotic cell death in diseases associated with aberrant apoptosis.

In one embodiment there is provided a peptide useful for the treatment of proliferative disease, including cancer and in particular for the stimulation of apoptosis, in cancer cells and other diseases exhibiting aberrant apoptosis. In particular the invention relates to VDAC1 specific amino acid sequences useful in inducing apoptosis. The VDAC1 peptides can induce apoptosis in primary cancers as well as in resistant cells and improve the efficacy of chemotherapeutic drugs.

Without wishing to be bound to theory the VDAC1-based peptides are designed to minimize the self-defense mechanisms in cancer cells, which involves over-expression of anti-apoptotic proteins. The present invention takes advantage of the central role that mitochondria and VDAC1, as the gatekeeper, play in apoptosis to generate potent, specific and effective VDAC1-based cancer therapies that diminish the activities of pro-survival proteins, promote apoptosis and increase chemotherapy effectiveness. Anti-apoptotic proteins are expressed in the majority of tumors, therefore the VDAC1 peptides are active in tumors regardless of the signaling pathway that controls apoptosis in the different tumor types.

DEFINITIONS

For convenience certain terms employed in the specification, examples and claims are described herein.

The term "VDAC1" as used herein and in the claims refers to the VDAC1 isoform of a highly conserved family of mitochondrial porin and the corresponding polynucleotides. Four VDAC isoforms, encoded by three genes, are known to date.

The term "VDAC1 cytosolic domains" refers to amino acid sequences that are exposed to the cytosol, as opposed to those exposed to the intermembranal space embedded within the membrane. The particular designation of VDAC1 amino acids forming parts of the protein cytosolic domain may change according to various protein structure definitions. In certain embodiments, the cytosolic domains include the VDAC1 N-terminal amino acids M1-D9 or M1-L26, β-loop 1 amino acids T64-D78 or N79, β-loop 2 amino acids S103-R119, and β-loop 4 amino acids G186-1226 or K199-N215. As used herein, a peptide derived from a cytosolic domain can include the amino acid sequence of the entire cytosolic domain or the peptide can include only a fragment of the cytosolic domain. The peptide t derived from a cytosolic domain may comprise up to about 30 consecutive amino acids, up to 26 consecutive amino acids, up to 25 consecutive amino acids, up to about 20 amino acids, or up to about 15 amino acids. In some embodiments the exemplary peptide sequences are set forth in SEQ ID NOs:1-3 and SEQ ID NO:5.

As used herein the term "apoptosis" or "apoptotic cell death" refers to programmed cell death which can be characterized by cell shrinkage, membrane blebbing and chromatin condensation culminating in cell fragmentation. Cells undergoing apoptosis also display a characteristic pattern of DNA cleavage. Alternatively, apoptosis can be characterized indirectly by changes in the activity or expression of members of the apoptotic pathway, e.g. increased mitochondrial release of cytochrome c. A non-limiting example of apoptosis-inducing reagents includes actinomycin D, antibiotic A-23187, b-lapachone, Camptothecin, ceramide, curcumin, dexamethasone, etoposide (Etopophos®, Vepesid®), Hypericin, prostaglandin A2, S-Nitrosoglutathione, staurosporin, sulindac sulfide, sulindac sulfone, Taxol®, vinblastine sulfate, vincristine sulfate, 15(S)-HPETE, 4-hydroxyphenyl retinamide, betulinic acid and the like.

As used herein, the term "modulates apoptosis" includes either upregulation or downregulation of apoptosis in a cell. Furthermore modulation of apoptosis includes enhancement of apoptosis in a cell that has previously received a signal that induces apoptosis, e.g., the cell has been subjected to a signal or chemical that induces apoptosis. Modulation of apoptosis is discussed in more detail below and can be useful in ameliorating various disorders, e.g., cancer and viral diseases.

The term "expression vector" and "recombinant expression vector" as used herein refers to a DNA molecule containing a desired coding sequence and appropriate nucleic acid sequences necessary for the expression of the operably linked coding sequence in a particular host organism. The expression vector may comprise sequences encoding heterologous domains including but not limited to protein detection, purification or cleavage sequences that may be fused at the N- or C-terminus to the desired coding sequence, to yield a fusion protein. It is contemplated that the present invention encompasses expression vectors that are integrated into host cell genomes, as well as vectors that remain unintegrated into the host genome.

Any vector selected can be constructed such that it is capable of being transferred into the cells of interest either with or without VDAC1 amino acid sequence. Methods for manipulating the vector nucleic acid are well known in the art and include for example direct cloning and site-specific recombination using recombinases. In this manner, an expression vector can be constructed such that it can be replicated in any desired cell, expressed in any desired cell, and can even become integrated into the genome of any desired cell.

The term "expression product" is used herein to denote a VDAC1 amino acid sequence. A VDAC1 expression product is preferably a translation product, or a fragment of translation product from any one or more of the VDAC1 polypeptides, polypeptide variants or peptides.

The term "exogenous" is used herein refers to a VDAC1 amino acid sequence which is introduced into a cell. For example, "exogenous VDAC1 amino acid sequence" should be construed to include a VDAC1 amino acid sequence expressed from a nucleic acid, which has been introduced into a cell using recombinant technology, a VDAC1 amino acid sequence that is added to a cell and any and all combinations thereof. Therefore, the term should not be construed to be limited solely to the addition of VDAC1 amino acid sequence to a cell per se, but should be expanded to include the expression of VDAC1 amino acid sequence in a cell when the VDAC1 amino acid sequence is expressed from a nucleic acid, which has been introduced into the cell.

The protein sequences of the human, mouse and rat VDAC isoforms are provided in the sequence listing herein below.

Human VDAC1 set forth in SEQ ID NO:21, (NP_003365) is a 283 amino acid protein. The numbering of the VDAC1 mutation begins at the alanine following the first methionine; Human VDAC2 set forth in SEQ ID NO:22 (NP_003366) is a 294 amino acid protein; Human VDAC3 set forth in SEQ ID NO:23 (NP_005653) is a 283 amino acid protein.

Mouse VDAC1 is set forth in SEQ ID NO:24 (NP_035824); Mouse VDAC2 is set forth in SEQ ID NO:25 (NP_035825); Mouse VDAC3 is set forth in SEQ ID NO:26 (NP_035826).

Rat vdac1 is set forth in SEQ ID NO:27 (NP_112643); Rat vdac2 is set forth in SEQ ID NO:28 (NP_112644); Rat vdac3 is set forth in SEQ ID NO:29 (NP_112645).

Alignment of the human amino acid sequences is shown in FIG. 8A-C. The corresponding polynucleotide sequences are set forth in SEQ ID NO:30-SEQ ID NO:38. The polynucleotide sequences of Human VDAC1, VDAC2 and VDAC3 having accession numbers NM_003374, NM_003375 and NM_005662 are set forth in SEQ ID NO:30-SEQ ID NO:32, respectively. The polynucleotide sequences of mouse VDAC1, VDAC2 and VDAC3 having accession numbers NM_011694, NM_011695 and NM_011696 are set forth in SEQ ID NO:33-SEQ ID NO:35, respectively. The polynucleotide sequences of rat VDAC1, VDAC2 and VDAC3 having accession numbers NM_031353, NM_031354 and NM_031355 are set forth in SEQ ID NO:36-SEQ ID NO:38, respectively.

Throughout the specification and the claims that follow, the terms "VDAC1 polypeptide", "VDAC1 peptide", "VDAC1 peptidomimetic" "VDAC1 peptide analog" and the like refers to molecules having a sequence which is a VDAC1 amino acid or a variant thereof, or a sequence derived from the VDAC1 family of proteins. Within the context of the present invention, a VDAC1 amino acid sequence can be or comprise one or more amino acid residue insertions, deletions, or substitutions. Preferably, any substitution is conservative in that it minimally disrupts the biochemical properties of the VDAC1 amino acid sequence polypeptide. Given the properties of the subject amino acids comprising the disclosed protein products, some rational substitutions will be recognized by the skilled worker. Amino acid substitutions, i.e. "conservative substitutions," may be made, for instance, on the basis of similarity in polarity, charge, solubility, hydrophobicity, hydrophilicity, and/or the amphipathic nature of the residues involved. Additionally, all or a part of the amino acids may be substituted with the D isoform of amino acids.

Figure 6:
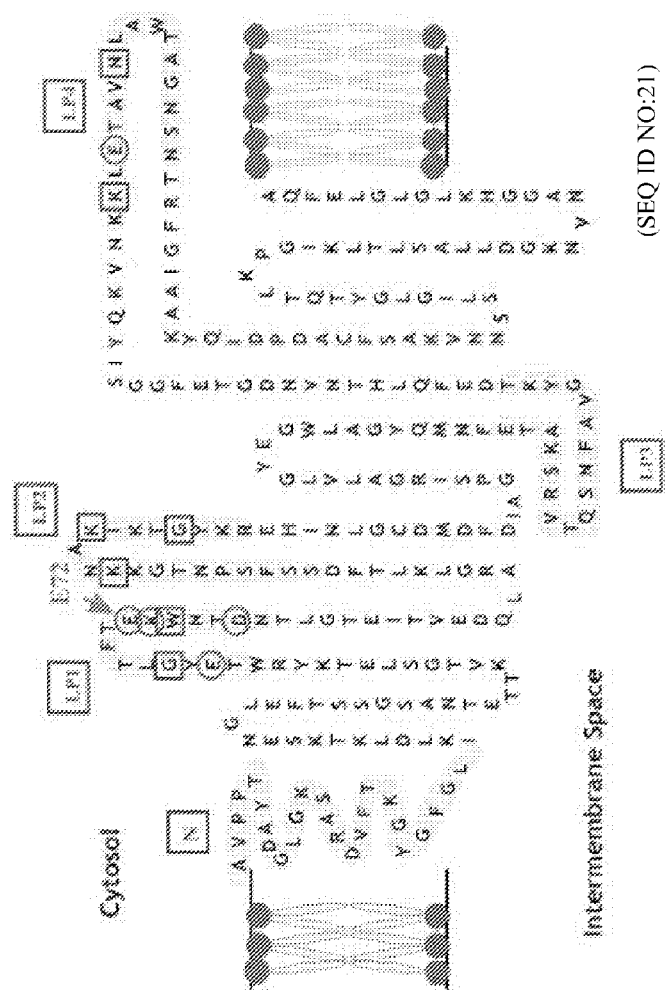
FIG. 6 is a model illustrating the proposed VDAC1 (SEQ ID NO:21) transmembrane topology and potential cytosolic, transmembrane and intermembranal domains, where the peptides and mutations are labeled.

The VDAC1 polypeptide variants according to the invention comprise a native VDAC1 polypeptide sequence having an amino acid substitution in one or more of the cytosolic domains. The cytosolic, transmembrane and intermembrane domains of VDAC1 are schematically shown in FIG. 6 (modified from Colombini, 2004).

The present invention also provides pharmaceutical formulations, both for veterinary and for human medical use, which comprise as the active agent one or more of the VDAC1 polypeptide, VDAC1 polypeptide variants, VDAC1 peptides, derivatives, analogs or salts thereof or a polynucleotide thereof described in the invention, for the manufacture of a medicament for the treatment or prophylaxis of the conditions variously described herein.

Polypeptides, Peptides, Peptide Derivatives and Peptide Analogs

Expression of exogenous VDAC1 protein and variants thereof in human cancer cell lines was shown to cause a dramatic increase in apoptosis in those cells. These results demonstrate that modulation of VDAC1 levels, either directly or indirectly, can be used to modulate apoptosis.

An "amino acid sequence", as used herein, refers to an oligopeptide, peptide, or polypeptide sequence, and fragments thereof, and to naturally occurring, recombinant or synthetic molecules. The term "polypeptide" refers to any chain of amino acids, regardless of length or post-translational modification (for example, glycosylation or phosphorylation).

The term "variant" as used herein refers to a polypeptide sequence that possesses some modified sequence of the wild type or parent protein. For example, the variant may have amino acids deleted, inserted or substituted.

The peptides, derivatives analogs and salts thereof comprise a VDAC1 amino acid sequence of up to about 70 amino acid residues, up to about 60 amino acid residues, up to about 40 amino acid residues, preferably from about 15 to about 30 amino acid residues in length.

The terms "peptide" or "peptide fragment" as used herein are meant to encompass natural, non-natural and/or chemically modified amino acid residues connected one to the other by peptide or non-peptide bonds. Therefore the term "peptide" includes a fragment, analog, derivative or a salt thereof. The amino acid residues are represented throughout the specification and claims by either one or three-letter codes, as is commonly known in the art. The compounds of the invention include linear and cyclic peptides and derivatives and analogs thereof.

The terms "analog" and "derivative" refer to a peptide comprising at least one altered amino acid residue by an amino acid substitution, addition, deletion, or chemical modification, as compared with the native peptide. Peptide analogs particularly include amino acid substitutions and/or additions with non-natural amino acid residues, and chemical modifications, which do not occur in nature. Peptide analogs include peptide variants and peptide mimetics. A peptide mimetic or "peptidomimetic" is a molecule that mimics the biological activity of a peptide but is not completely peptidic in nature. Whether completely or partially non-peptide, peptidomimetics according to this invention provide a spatial arrangement of chemical moieties that closely resembles the three-dimensional arrangement of groups in the peptide on which the peptidomimetic is based. As a result of this similar active-site geometry, the peptidomimetic has effects on biological systems, which are similar to the biological activity of the peptide.

Peptide derivatives particularly include amino acid substitutions and/or additions with naturally occurring amino acid residues, and chemical modifications such as, for example, enzymatic modifications, typically present in nature. Accordingly, the present invention encompasses both peptide derivatives and analogs of the VDAC peptides as set forth in SEQ ID NO:1-SEQ ID NO:3, SEQ ID NO:5, SEQ ID NO:11-SEQ ID NO:13, SEQ ID NO:15 and SEQ ID NO:73.

The present invention encompasses VDAC peptide derivatives or analogs of which at least one amino acid has been chemically modified. Chemical modifications of amino acid residues include, but are not limited to, amidation, methylation, acetylation, glycosylation, oxidation, reduction, myristylation, sulfation, acylation, ADP-ribosylation, cyclization, hydroxylation, iodination, derivatization by protecting/blocking groups, or any other derivatization method known in the art. Such alterations, which do not destroy, but may improve the VDAC peptide biological activity, can occur anywhere along the sequence of the VDAC peptide, including at the peptide backbone, the amino acid side-chains, and at the amino or carboxyl termini.

By using "amino acid substitution", it is meant that an amino acid residue is substituted for a residue within the sequence resulting in a functionally equivalent or in a functionally different variant. The term "functionally equivalent" means, for example, a group of amino acids having similar polarity, similar charge, or similar hydrophobicity. For example, one or more amino acid residues within the sequence can be substituted by another amino acid of a similar polarity, which acts as a functional equivalent, resulting in a silent alteration. Substitutes for an amino acid within the sequence can be selected from other members of the class to which the amino acid belongs. For example, the non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid (aspartate and glutamate). Such substitutions are known as conservative substitutions.

Additionally, a non-conservative substitution can be made in an amino acid that does not contribute to the biological activity of the peptide. Such non-conservative substitutions are also encompassed within the term "amino acid substitution", as used herein. It will be appreciated that the present invention further encompasses VDAC1 peptide derivatives or analogs, wherein at least one amino acid is substituted by another natural or non-natural amino acid to produce a peptide derivative or analog having increased stability or higher half life as compared to the native VDAC1 peptide fragment.

The present invention encompasses peptide hydrates and includes, but is not limited to, hemihydrate, monohydrate, dihydrate, trihydrate, and the like.

One aspect of the present invention provides a VDAC peptide further comprising a moiety that facilitates cell penetration. In one embodiment the moiety is a cell penetrating peptide (CPP). CPP's are typically amphipathic or cationic oligopeptides able to transport attached cargoes across cell membranes. In one embodiment the CPP comprises a fragment of the *Drosophila* antennapedia homeodomain (ANTP), comprising an amino acid sequence as set forth in SEQ ID NO: 39.

SEQ ID NO:39: MRQIKIWFQNRRMKWKK which is encoded by a nucleotide set forth in SEQ ID NO: 40 5' ATG CGT CAG ATT AAA ATT TGG TTT CAG AAT CGT CGT ATG AAA TGG AAA AAA.

In another embodiment, the CPP comprises a fragment of the HIV-1 transcriptional factor TAT having the amino acid sequence set forth in SEQ ID NO:76:

RKKRRQRRRGG.

In yet further embodiment, the CPP comprises a fragment of the TfR domain (having the amino acid sequence set forth in SEQ ID NO:75) recognised by transferrin receptor: HAIYPRH.

The peptide or polypeptide of the invention can further comprise a tryptophan zipper pentamer or other sequence to further stabilize the peptide (Cochran, 2001). The amino acid sequences of the tryptophan zipper pentamer are set forth in SEQ ID NO: 41 and SEQ ID NO:42. SEQ ID NO:41: SWTWE and SEQ ID NO:42: KWTWK.

One aspect of the present invention provides for a peptide analog such as a peptidomimetic, which mimics the structural features of the critical minimal epitope.

There are clear advantages for using a mimetic of a given peptide rather than the peptide itself, since peptide drugs often exhibit two undesirable properties: poor bioavailability and short duration of action. Peptide mimetics offer a route around these two major obstacles; since the molecules concerned have a long duration of action. Furthermore there are problems associated with stability, storage and immunoreactivity for peptides that are not experienced with peptide mimetics.

The design of the peptidomimetics may be based on the three-dimensional structure of VDAC alone with or in complex with another protein. Interaction with the peptidomimetic can either induce an interacting protein to carry out the normal function caused by such binding (agonist) or disrupts such function (antagonist, inhibitor).

A primary goal in the design of peptide mimetics has been to reduce the susceptibility of mimics to cleavage and inactivation by peptidases. In one approach, one or more amide bonds have been replaced in an essentially isosteric manner by a variety of chemical functional groups. In another approach, a variety of uncoded or modified amino acids such as D-amino acids and N-methyl amino acids have been used to modify mammalian peptides. Alternatively, a presumed bioactive conformation has been stabilized by a covalent modification, such as cyclization or by incorporation of γ-lactam or other types of bridges as disclosed for example in U.S. Pat. No. 5,811,392. In U.S. Pat. No. 5,552,534, non-peptide compounds are disclosed which mimic or inhibit the chemical and/or biological activity of a variety of peptides. Such compounds can be produced by appending to certain core species, such as the tetrahydropyranyl ring, chemical functional groups, which cause the compounds to be at least partially cross-reactive with the peptide. As will be recognized, compounds which mimic or inhibit peptides are to varying degrees cross-reactive therewith. Other techniques for preparing peptidomimetics are disclosed in U.S. Pat. Nos. 5,550,251 and 5,288,707, for example. Non-limiting examples of the use of peptidomimetics in the art include inhibitors of protein isoprenyl transferases (particularly protein farnesyltransferase and geranylgeranyltransferase) and anti-cancer drugs (U.S. Pat. No. 5,965,539) inhibitors of p21 ras (U.S. Pat. No. 5,910,478) and inhibitors of neurotropin activity (U.S. Pat. No. 6,291,247).

Whenever VDAC1 peptide fragments are mentioned in the invention, also salts and functional derivatives thereof are contemplated, as long as they are able to induce apoptosis of a target cell. Thus, the present invention encompasses peptides containing non-natural amino acid derivatives or non-protein side chains.

The term "derivative" includes any chemical derivative of the peptide fragments of the invention having one or more residues chemically derivatized by reaction of side chains or functional groups. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. For example, free carboxyl groups may be derivatized to form salts, methyl and ethyl esters or other types of esters or hydrazides; free hydroxyl groups may be derivatized to form O-acyl or O-alkyl derivatives; the imidazole nitrogen of histidine may be derivatized to form N-im-benzylhistidine. The C-terminus of the peptide of the invention may be presented in the free carboxy form or, preferably, it is amidated to facilitate the synthesis and increase the stability of the peptide, for example to increase the resistance of the peptides to enzymatic cleavage in the organism, or modified in a way that increases its solubility.

Also included as chemical derivatives are those peptides, which contain one or more naturally occurring amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted for serine; and ornithine may be substituted for lysine.

In addition, a VDAC peptide can differ from the natural sequence of the peptides of the invention by chemical modifications including, but are not limited to, terminal-$NH_2$ acylation, acetylation, or thioglycolic acid amidation, and by terminal-carboxlyamidation, e.g., with ammonia, methylamine, and the like. Peptides can be linear, cyclic or branched and the like, which conformations can be achieved using methods well known in the art.

Addition of amino acid residues may be performed at either terminus of the polypeptides or peptides of the invention for the purpose of providing a "linker" by which the peptides of this invention can be conveniently bound to a carrier. Such linkers are usually of at least one amino acid residue and can be of 40 or more residues, more often of 1 to 10 residues. Typical amino acid residues used for linking are tyrosine, cysteine, lysine, glutamic and aspartic acid, or the like.

Peptide Synthesis

The peptides, peptide derivatives and peptide analogs of the invention may be synthesized using any recombinant or synthetic method known in the art, including, but not limited to, solid phase (e.g. Boc or f-Moc chemistry) and solution phase synthesis methods. For solid phase peptide synthesis, a summary of the many techniques may be found in Stewart and Young, 1963; and Meienhofer, 1973. For a review of classical solution synthesis, see Schroder and Lupke, 1965.

The amino acid residues described herein are preferred to be in the "L" isomeric form. However, residues in the "D" isomeric form can be substituted for any L-amino acid residue, as long as the peptide substantially retains the desired functional property. Use of "D" amino acids may be used as is known in the art to increase the stability or half-life of the resultant peptide.

Nucleic Acids

In another aspect, the invention provides nucleic acid molecules encoding the native or mutated VDAC1 polypeptide or peptides of the invention.

The nucleic acid molecules may include DNA, RNA, or derivatives of either DNA or RNA. An isolated nucleic acid sequence encoding a peptide can be obtained from its natural source, for example as a portion of a gene. A nucleic acid molecule can also be produced using recombinant DNA technology (e.g., polymerase chain reaction (PCR) amplification, cloning) or chemical synthesis. Nucleic acid sequences include natural nucleic acid sequences and homologs thereof, comprising, but not limited to, natural allelic variants and modified nucleic acid sequences in which nucleotides have been inserted, deleted, substituted, and/or inverted in such a manner that such modifications do not substantially interfere with the nucleic acid molecule's ability to encode a functional peptide of the present invention.

A nucleic acid molecule homolog can be produced using a number of methods known to those skilled in the art (see, for example, Sambrook et al., 1989). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologs can be selected from a mixture of modified nucleic acids by screening for the function of the protein encoded by the nucleic acid with respect to the induction of an anti-viral response, for example by the methods described herein.

A polynucleotide or oligonucleotide sequence can be deduced from the genetic code of a protein, however, the degeneracy of the code must be taken into account, and nucleic acid sequences of the invention also include sequences, which are degenerate as a result of the genetic code, which sequences may be readily determined by those of ordinary skill in the art.

The terms "nucleic acid" and "polynucleotide" and "nucleotide sequence" as used herein refer to an oligonucleotide, polynucleotide or nucleotide and fragments or portions thereof, and to DNA or RNA of genomic or synthetic origin, which may be single- or double-stranded, and represent the sense or antisense strand. The term should also be understood to include, as equivalents, analogs of either RNA or DNA made from nucleotide analogs, and, as applicable to the embodiment being described.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomers", and "probes", as commonly defined in the art.

As used herein, highly stringent conditions are those, which are tolerant of up to about 5% to about 25% sequence divergence, preferably up to about 5% to about 15%. Without limitation, examples of highly stringent ($-10°$ C. below the calculated Tm of the hybrid) conditions use a wash solution of 0.1×SSC (standard saline citrate) and 0.5% SDS at the appropriate Ti (incubation temperature) below the calculated Tm of the hybrid. The ultimate stringency of the conditions is primarily due to the washing conditions, particularly if the hybridization conditions used are those, which allow less stable hybrids to form along with stable hybrids. The wash conditions at higher stringency then remove the less stable hybrids. A common hybridization condition that can be used with the highly stringent to moderately stringent wash conditions described above is hybridization in a solution of 6×SSC (or 6×SSPE), 5×Denhardt's reagent, 0.5% SDS, 100 µg/ml denatured, fragmented salmon sperm DNA at an appropriate incubation temperature Ti. See generally Sambrook et al., Molecular Cloning: A Laboratory Manual, 2d edition, Cold Spring Harbor Press (1989)) for suitable high stringency conditions.

Stringency conditions are a function of the temperature used in the hybridization experiment and washes, the molarity of the monovalent cations in the hybridization solution and in the wash solution(s) and the percentage of formamide in the hybridization solution. In general, sensitivity by hybridization with a probe is affected by the amount and specific activity of the probe, the amount of the target nucleic acid, the detectability of the label, the rate of hybridization, and the duration of the hybridization. The hybridization rate is maximized at a Ti of 20-25° C. below Tm for DNA:DNA hybrids and 10-15° C. below Tm for DNA:RNA hybrids. It is also maximized by an ionic strength of about 1.5M $Na^+$. The rate is directly proportional to duplex length and inversely proportional to the degree of mismatching.

Specificity in hybridization, however, is a function of the difference in stability between the desired hybrid and "background" hybrids. Hybrid stability is a function of duplex length, base composition, ionic strength, mismatching, and destabilizing agents (if any).

The Tm of a perfect hybrid may be estimated for DNA: DNA hybrids using the equation of Meinkoth et al (1984), as $$Tm = 81.5° C. + 16.6(\log M) + 0.41(\% GC) - 0.61(\% \text{form}) - 500/L$$

and for DNA:RNA hybrids, as $$Tm = 79.8° C. + 18.5(\log M) + 0.58(\% GC) - 11.8(\% GC)^2 - 0.56(\% \text{form}) - 820/L$$

where

M, molarity of monovalent cations, 0.01-0.4 M NaCl,

% GC, percentage of G and C nucleotides in DNA, 30%-75%,

% form, percentage formamide in hybridization solution, and

L, length hybrid in base pairs.

Tm is reduced by 0.5-1.5° C. (an average of 1° C. can be used for ease of calculation) for each 1% mismatching. The Tm may also be determined experimentally. As increasing length of the hybrid (L) in the above equations increases the Tm and enhances stability, the full-length rat gene sequence can be used as the probe.

Filter hybridization is typically carried out at 68° C., and at high ionic strength (e.g., 5-6×SSC), which is non-stringent, and followed by one or more washes of increasing stringency, the last one being of the ultimately desired high stringency. The equations for Tm can be used to estimate the appropriate Ti for the final wash, or the Tm of the perfect duplex can be determined experimentally and Ti then adjusted accordingly.

The present invention further includes a nucleic acid sequence of the present invention operably linked to one or more transcription control sequences to form a recombinant molecule. The phrase "operably linked" refers to linking a nucleic acid sequence to a transcription control sequence in a manner such that the molecule is able to be expressed when transfected (i.e., transformed, transduced or transfected) into a host cell. Transcription control sequences are sequences, which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in animal, bacteria, helminth, yeast and insect cells.

A nucleic acid molecule of the invention may be inserted into appropriate expression vector, i.e., a vector which contains the necessary elements for the transcription and translation of the inserted coding sequence.

Vectors can be introduced into cells or tissues by any one of a variety of known methods within the art, including in vitro recombinant DNA techniques, synthetic techniques, and in vivo genetic recombination. Such methods are generally described in Sambrook et al., Molecular Cloning: A Laboratory Manual, Cold Springs Harbor Laboratory, New York 1989, 1992; in Ausubel et al., Current Protocols in Molecular Biology, John Wiley and Sons, Baltimore, Md. 1989.

A recombinant cell of the present invention comprises a cell transfected with a nucleic acid molecule that encodes a polypeptide or peptide of the invention. A variety of expression vector/host systems may be utilized to contain and express sequences encoding the viral antigens of the invention. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not meant to be limited by the host cell employed. The expression of the construct according to the present invention within the host cell may be transient or it may be stably integrated in the genome thereof.

Upregulation of Activity/Expression Level of VDAC1

In one embodiment VDAC1 expression can be upregulated using a method that comprises the step of providing an exogenous VDAC1 molecule to the cell under conditions sufficient for said VDAC1 amino acid sequence to induce apoptosis of the cell. In some embodiments the VDAC1 molecule is selected from a VDAC1 polypeptide, a VDAC1 polypeptide variant and a VDAC1 peptide, derivative analog or salt thereof according to the principles of the present invention. In other embodiments VDAC1 molecule is selected from a VDAC1 nucleotide sequence according to the principles of the present invention.

In addition to administering a VDAC polypeptide, VDAC polypeptide variant, or polynucleotide directly to the cell, the upregulation VDAC1 level can be effected at one of three levels within a cell: at the genomic level for example by activation of transcription by means of tissue specific or cell specific promoters, enhancers, or other regulatory elements; at the transcript level for example by polyadenylation or activation of translation, or at the protein level for example via post-translational modifications or interaction with inhibitory proteins and the like.

Following is a non-comprehensive list of agents capable of upregulating the expression level and/or activity of VDAC1.

An agent capable of upregulating expression of a VDAC1 may be an exogenous polynucleotide sequence designed and constructed to express VDAC1, VDAC1 variant or at least a functional fragment thereof. Accordingly, the exogenous polynucleotide sequence may be a DNA or RNA sequence encoding a VDAC1 molecule, capable of regulating apoptosis.

The phrase "functional fragment" as used herein refers to part of the VDAC 1 protein (i.e., a peptide) that exhibits functional properties of the protein, such as inducing or preventing apoptosis in a cell. According to preferred embodiments of the present invention, the functional portion of VDAC1 is a polypeptide or peptide having a sequence selected from SEQ ID NO:21, SEQ ID NO:24 or SEQ ID NO:27, or a variant form thereof which retains the ability to induce apoptosis can be used. VDAC1 has been cloned from human, rat, mouse, yeast and plant sources, therefore coding sequence information for VDAC1 is available from gene and protein databases, including the GenBank database.

To express exogenous VDAC1 in mammalian cells, a polynucleotide sequence encoding a VDAC1 or a variant SEQ ID NO:30, SEQ ID NO:33, SEQ ID NO:36, SEQ ID NO:51-SEQ ID NO:56) is preferably ligated into a nucleic acid construct suitable for mammalian cell expression. Such a nucleic acid construct includes a promoter sequence for directing transcription of the polynucleotide sequence in the cell in a constitutive or inducible manner.

It will be appreciated that the nucleic acid construct of the present invention can also utilize VDAC1 homologues, which exhibit the desired activity (i.e. modulation of apoptosis) can be, for example, at least about 75%, 80%, 85%, 90%, 95%, 96%, 97%, 98%, 99% or more identical to a nucleotide sequence encoding a protein of the invention (e.g., to the entire length of the nucleotide sequence encoding the protein), or a biologically active portion or complement of any of these nucleotide sequences as determined using the BestFit software of the Wisconsin sequence analysis package, utilizing the Smith and Waterman algorithm.

Constitutive promoters suitable for use with the present invention are promoter sequences that are active under most environmental conditions and most types of cells, such as the cytomegalovirus (CMV) and Rous sarcoma virus (RSV). Inducible promoters suitable for use with the present invention include for example the tetracycline-inducible promoter (Zabala, M. et al., 2004).

The nucleic acid construct (also referred to herein as an "expression vector") of the present invention includes additional sequences that render this vector suitable for replication and integration in prokaryotes, eukaryotes, or preferably both (e.g., shuttle vectors). A typical cloning vector may also contain transcription and translation initiation sequences, transcription and translation terminators, and a polyadenylation signal.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated. Enhancer elements can stimulate transcription from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus or human or murine cytomegalovirus (CMV) and the long tandem repeats (LTRs) from various retroviruses, such as murine leukemia virus, murine or Rous sarcoma virus, and HIV. In constructing the expression vector, the promoter can be accommodated at various distances from the transcription start site without loss of promoter function.

Polyadenylation sequences can also be added to the expression vector in order to increase the efficiency of VDAC1 mRNA translation, including a GU- or U-rich sequence located downstream from the polyadenylation site and a highly conserved sequence of six nucleotides, namely AAUAAA, located 11-30 nucleotides upstream of the site. Termination and polyadenylation signals suitable for the present invention include those derived from SV40.

In addition to the embodiments already described, the expression vector of the present invention may also contain other specialized elements intended to increase the level of expression of cloned nucleic acids or to facilitate the identification of cells that carry the recombinant DNA. For example, a number of animal viruses contain DNA sequences that promote extra-chromosomal replication of the viral genome in permissive cell types. Plasmids bearing these viral replicons are replicated episomally as long as the appropriate factors are provided by genes either carried on the plasmid or with the genome of the host cell.

The expression vector of the present invention may or may not include a eukaryotic replicon. If a eukaryotic replicon is present, the vector is capable of amplification in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of the present invention may further comprise polynucleotide sequences that allow, for example, the translation of several proteins from a single mRNA, such as an internal ribosome entry site (IRES) and sequences for genomic integration of the promoter-chimeric polypeptide.

Mammalian expression vectors are commercially available.

Viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by the present invention will depend on the cell type transformed. The ability to select suitable vectors according to the cell type transformed is well within the capabilities of the ordinarily skilled artisan and as such, no general description of selection considerations is provided herein.

Recombinant viral vectors are useful for in vivo expression of VDAC1 since they offer advantages such as lateral infection and targeting specificity of targeted cells.

Introduction of nucleic acids by viral infection offers several advantages over other methods such as lipofection and electroporation, since higher transfection efficiency can be obtained due to the infectious nature of viruses.

An agent capable of upregulating a VDAC1 may also comprise any compound capable of increasing the transcription and/or translation of an endogenous DNA or mRNA encoding the VDAC1 and thus increasing endogenous VDAC1 activity.

An agent capable of upregulating a VDAC1 may also comprise an exogenous polypeptide, including at least a functional portion (as described hereinabove) of the VDAC1

Pharmaceutical Compositions

The present invention provides pharmaceutical compositions comprising a polypeptide or nucleic acid as described above and a physiologically acceptable carrier.

Depending on the location of the tissue of interest, VDAC1 amino acid sequence can be supplied in any manner suitable for the provision of VDAC1 amino acid sequence. Thus, for example, a composition containing a source of VDAC1 amino acid sequence (i.e., a VDAC1 polypeptide or a VDAC1 expression vector, or cells expressing a VDAC1 amino acid sequence, as described herein) can be introduced into tissue of interest (e.g., injected, or pumped as a continuous infusion, or as a bolus within a tumor or intercutaneous or subcutaneous site, applied to all or a portion of the surface of the skin, dropped onto the surface of the eye, etc.).

Apart from other considerations, the fact that the novel active ingredients of the invention are polypeptides, peptides, peptide analogs or peptidomimetics, dictates that the formulation be suitable for delivery of these types of compounds. In general, peptides are less suitable for oral administration due to susceptibility to digestion by gastric acids or intestinal enzymes, but it is now disclosed that the compositions according to the present invention may be administered orally. The pharmaceutical composition of this invention may be administered by any suitable means, such as topically, or parenterally including intranasal, subcutaneous, intramuscular, intravenous, intra-arterial, intraarticular, or intralesional administration. Ordinarily, intravenous (i.v.), intraarticular or oral administration will be preferred.

The molecules of the present invention as active ingredients are dissolved, dispersed or admixed in a diluent or excipient that is pharmaceutically acceptable and compatible with the active ingredient as is well known. Suitable excipients are, for example, water, saline, phosphate buffered saline (PBS), dextrose, glycerol, ethanol, or the like and combinations thereof. Other suitable carriers are well known to those in the art. (See, for example, Ansel et al., 1990 and Gennaro, 1990). In addition, if desired, the composition can contain minor amounts of auxiliary substances such as wetting or emulsifying agents, pH buffering agents.

Pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active compounds into preparations which, can be used pharmaceutically. Proper formulation is dependent upon the route of administration chosen.

For injection, the compounds of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants for example, polyethylene glycol are generally known in the art.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration. For buccal administration, the compositions may take the form of tablets or lozenges formulated in conventional manner.

For administration by inhalation, the variants for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the peptide and a suitable powder base such as lactose or starch.

Pharmaceutical compositions for parenteral administration include aqueous solutions of the active ingredients in water-soluble form. Additionally, suspensions of the active compounds may be prepared as appropriate oily injection suspensions. Suitable natural or synthetic carriers are well known in the art (Pillai et al., 2001). Optionally, the suspension may also contain suitable stabilizers or agents, which increase the solubility of the compounds, to allow for the preparation of highly concentrated solutions. Alternatively, the active ingredient may be in powder form for reconstitution with a suitable vehicle, e.g., sterile, pyrogen-free water, before use.

The compounds of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of a compound effective to prevent, delay, alleviate or ameliorate symptoms of a disease of the subject being treated. Determination of a therapeutically effective amount is well within the capability of those skilled in the art.

Toxicity and therapeutic efficacy of the polypeptides, fragments and analogs described herein can be determined by standard pharmaceutical procedures in cell cultures or experimental animals, e.g., by determining the $IC_{50}$ (the concentration which provides 50% inhibition) and the LD50 (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition (e.g. Fingl, et al., 1975, in "The Pharmacological Basis of Therapeutics", Ch. 1 p. 1).

Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on the subject being treated, the severity of the affliction, the manner of administration, the judgment of the prescribing physician, and all other relevant factors.

In one particularly preferred embodiment according to the present invention, the peptides are administered orally (e.g. as a syrup, capsule, or tablet). In certain embodiments, peptide delivery can be enhanced by the use of protective excipients. This is typically accomplished either by complexing the peptide with a composition to render it resistant to acidic and enzymatic hydrolysis or by packaging the polypeptide in an appropriately resistant carrier such as a liposome. Means of protecting polypeptides for oral delivery are well known in the art (see, e.g., U.S. Pat. No. 5,391,377 describing lipid based formulations for oral delivery of therapeutic agents).

Elevated serum half-life can be maintained by the use of sustained-release protein "packaging" systems. Such sustained release systems are well known to those of skill in the art. In one preferred embodiment, a biodegradable microsphere delivery system for proteins and peptides such as the ProLease® system (reviewed in Tracy, 1998) a dry powder composed of biodegradable polymeric microspheres containing the peptide in a polymer matrix that can be compounded as a dry formulation with or without other agents. Serum half-life can also be extended by conjugating the peptide or polypeptide of the invention to a moiety such as PEG using reagents and methods known to those with skill in the art.

The foregoing formulations and administration methods are intended to be illustrative and not limiting. It will be appreciated that, using the teaching provided herein, other suitable formulations and modes of administration can be readily devised.

A tablet may be made by compression or molding, optionally with one or more accessory ingredients. Compressed tablets may be prepared by compressing in a suitable machine the active peptide(s) in a free-flowing form such as a powder or granules, optionally mixed with a binder, (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose), surface active or dispersing agent. Molded tablets may be made by molding in a suitable machine a mixture of the powdered peptide(s) moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile.

A syrup may be made by adding the active peptide(s) to a concentrated, aqueous solution of a sugar, for example, sucrose, to which may also be added any necessary ingredients. Such accessory ingredients may include flavorings, an agent to retard crystallization of the sugar or an agent to increase the solubility of any other ingredients, such as a polyhydric alcohol, for example, glycerol or sorbitol.

In addition to the aforementioned ingredients, the formulations of this invention may further include one or more accessory ingredient(s) selected from diluents, buffers, flavoring agents, binders, surface active agents, thickeners, lubricants, preservatives, (including antioxidants) and the like.

According to some embodiments of the invention, the therapeutically effective amount of the VDAC1 polypeptide, polypeptide variant, peptide, derivative or analog is a dosage in a range from about 0.02 mg/kg to about 10 mg/kg. Preferably, the dosage of the VDAC1 amino acid sequence according to the present invention is in a range from about 0.05 mg/kg to about 2 mg/kg, more preferably, the dosage of the VDAC1 peptide, derivative or analog is in a range from about 0.1 mg/kg to about 1 mg/kg. It will be understood that the dosage may be an escalating dosage so that low dosage may be administered first, and subsequently higher dosages may be administered until an appropriate response is achieved. Also, the dosage of the composition can be administered to the subject in multiple administrations in the course of the treatment period in which a portion of the dosage is administered at each administration.

Without wishing to be bound to theory, the peptide, derivative or analog thereof is designed to interfere with VDAC1 protein-protein interactions. Preferably, the peptide, derivative or analog thereof is designed to inhibit interactions between VDAC1 protein and a mitochondrial anti-apoptosis protein.

The art discloses examples of peptides and analogs thereof designed to interfere with protein-protein interactions. For example, SAHB (stabilized a helix of BCL2 domains) is a helical, protease resistant, cell permeable peptidomimetic useful for activation of apoptosis in cancer cells (Walensky et al., 2004). Another example is a peptidomimetic designed to mimic the protein-protein interactions of an apoptotic activator, SMAC (Li et al, 2004).

It will be apparent to those of ordinary skill in the art that the therapeutically effective amount of the molecule according to the present invention will depend, inter alia upon the administration schedule, the unit dose of molecule administered, whether the molecule is administered in combination with other therapeutic agents, the immune status and health of the patient, the therapeutic activity of the molecule administered and the judgment of the treating physician. As used herein, a "therapeutically effective amount" refers to the amount of a molecule required to alleviate one or more symptoms associated with a disorder being treated over a period of time.

In some embodiments the peptides and derivatives and analogs thereof of the present invention are delivered to cells as modified peptides. In one embodiment the peptides of the invention are linked to a cell penetrating peptide (CPP). In one preferred embodiment the CPP is an amino acid sequence comprising the *Drosophila* antennapedia (ANTP) domain or a fragment thereof.

In other embodiments the peptides of the present invention are delivered to cells as nucleic acids encoding the peptides in a non-viral gene delivery system. Particulate gene transfer systems are usually based on oligo- or polycationic carrier molecules which can condense nucleic acids by electrostatic interactions with their negatively charged phosphate backbone. The positive charge of cationic lipids leads to electrostatic interaction with the DNA, the lipidic moiety enables the hydrophobic collapse and the formation of so called lipoplexes'. Polycationic carrier molecules, like polylysine or polyethyleneimine (PEI) bind and condense DNA due to their high density of positive charges and result in the formation of so called 'polyplexes'. The surface of the delivery particle can be coated with hydrophilic polymers, e.g. polyethyleneglycol (PEG), which prevent binding to plasma proteins, blood cells and the RES and also enables a prolonged circulation time in the blood stream.

In yet another embodiment, the peptides of the present invention are delivered to cells in vesicles. Immunoliposomes have been described to allow targeted delivery of anticancer drugs into solid tumors (for review see Sapra and Allen et al, 2004).

Polypeptides and peptides, and polynucleotide sequences of the present invention can be administered to a subject following microencapsulation. Methods of preparing microcapsules are known in the art and include preparation from an assortment of materials including natural and synthetic materials.

Therapeutic Use

Without wishing to be bound to theory, the mitochondrial pathway serves as an excellent target for apoptosis-inducing therapies for several reasons:

Mitochondria are integrators of the apoptotic signal: they store apoptotic molecules and release them to the cytosol to initiate caspase cascades;

Mitochondria-directed agents are predicted to be effective at low concentrations, since only a fraction of a cell's mitochondria need to be involved for apoptosis to ensue;

Downstream effectors of mitochondrial apoptosis are present in all cell types, and seem to be conserved in tumor cells; and Mitochondrial apoptosis induction is known to kill cells effectively.

Accordingly, the present invention provides VDAC1 polypeptides, polypeptide variants, peptides, and analogs, derivatives and salts thereof useful in promoting or inhibiting apoptosis in the treatment of diseases associated with aberrant apoptosis.

As used herein, the phrase "diseases associated with aberrant apoptosis" includes diseases and disorders in which timely apoptosis does not ensue and cells proliferate without restraint, for example in proliferative diseases including cancer and tumor growth.

In one preferred embodiment the VDAC1 compounds of the invention are useful in preventing or alleviating a cell-proliferative disorder or a symptom of a cell-proliferative disorder. Cell-proliferative disorders and/or a symptom of a cell-proliferative disorder are prevented or alleviated by administering a VDAC1 polypeptide, polypeptide variant, or peptide to a subject. The cell-proliferative disorder is, for example, neoplasias including solid tumor cancers of the lung, pancreas, stomach, colon, rectum, kidney, breast, cervical/uterine, ovarian, testicular, melanoma, head and neck, and esophagus, as well as hematological cancers, such as leukemias and lymphomas, non-malignant neoplasias, cellular expansions due to DNA viruses such as Epstein-Barr virus, African swine fever virus and adenovirus, lymphoproliferative conditions, arthritis, inflammation, or autoimmune diseases.

Methods of Promoting Apoptosis

The present invention provides compounds, compositions and methods of promoting, inducing or enhancing apoptosis. Promotion or induction of apoptosis is useful in the treatment of various disorders associated with aberrant cell proliferation, such as, for example, neoplasias including solid and non-solid cancers and non-malignant neoplasias. Diseases and disorders such as lymphoproliferative conditions, cancer including drug resistant cancer, arthritis, inflammation, autoimmune diseases and the like result from a defect in cell death regulation. Furthermore, certain viruses including Epstein-Barr virus and adenovirus, utilize the host cellular machinery to drive their own replication while repressing host cell death. Accordingly, it would be desirable to promote, induce or enhance apoptotic mechanisms in such disease conditions.

The present invention provides a method for inducing apoptotic cell death comprising contacting a cell with a VDAC1 derived peptide or VDAC1 polypeptide.

In one preferred embodiment of the invention, the compounds of the present invention are useful for the preparation of a medicament for inhibiting proliferative diseases or disorders including tumor growth and tumor progression. In another embodiment of the invention, the compounds are useful for preventing, treating or inhibiting a cell proliferative disease or disorder. The cell proliferative disease can be malignant or benign. The compositions are useful for the treatment or prevention of non-solid cancers, e.g. hematopoietic malignancies such as, but not being limited to, all types of leukemia, e.g. chronic myelogenous leukemia (CML), acute myelogenous leukemia (AML), mast cell leukemia, chronic lymphocytic leukemia (CLL) and acute lymphocytic leukemia, lymphomas, and multiple myeloma, as well as of solid tumors such as, but not being limited to, mammary, ovarian, prostate, colon, cervical, gastric, esophageal, papillary thyroid, pancreatic, bladder, colorectal, melanoma, small-cell lung and non-small-cell lung cancers, granulosa cell carcinoma, transitional cell carcinoma, vascular tumors, all types of sarcomas, e.g. osteosarcoma, chondrosarcoma, Kaposi's sarcoma, myosarcoma, hemangiosarcoma, and glioblastomas.

It is to be understood that the terms "treating a proliferative disease or disorder" as used herein in the description and in the claims, are intended to encompass tumor formation, primary tumors, tumor progression or tumor metastasis.

In one preferred embodiment of the invention, the compounds of the present invention are useful for the preparation of a medicament for inhibiting proliferative diseases or disorders including tumor growth and tumor progression. In another embodiment of the invention, the compounds are useful for preventing, treating or inhibiting a cell proliferative disease or disorder. The cell proliferative disease can be malignant or benign. The compositions are useful for the treatment or prevention of non-solid cancers, e.g. hematopoietic malignancies such as, but not being limited to, all types of leukemia, e.g. chronic myelogenous leukemia (CML), acute myelogenous leukemia (AML), mast cell leukemia, chronic lymphocytic leukemia (CLL) and acute lymphocytic leukemia, lymphomas, and multiple myeloma, as well as of solid tumors such as, but not being limited to, mammary, ovarian, prostate, colon, cervical, gastric, esophageal, papillary thyroid, pancreatic, bladder, colorectal, melanoma, small-cell lung and non-small-cell lung cancers, granulosa cell carcinoma, transitional cell carcinoma, vascular tumors, all types of sarcomas, e.g. osteosarcoma, chondrosarcoma, Kaposi's sarcoma, myosarcoma, hemangiosarcoma, and glioblastomas.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Materials and Methods

Materials

Carboxymethyl (CM)-cellulose, glucose-6-phosphate, glucose-6-phosphate dehydrogenase (G-6-PDH), HEPES, leupeptin, mannitol, PMSF, Ru360, soybean asolectin, staurosporine, sucrose and Tris were purchased from Sigma (USA). Cibacron blue-agarose was purchased from Amersham Biosciences (Sweden). n-Octyl-b-D-glucopyranoside (β-OG) was obtained from Bachem AG (Bubendorf, Switzerland). Lauryl-(dimethyl)-aminooxide (LDAO) and ruthenium red (97% pure) were obtained from Fluka (Switzerland). Hydroxyapatite (Bio-Gel HTP) was purchased from Bio-Rad Laboratories (USA) and Celite from the British Drug Houses (UK). Monoclonal anti-VDAC antibodies raised against the N-terminal region of 31HL human porin were purchased from Calbiochem (clone no. 173/045, Cat. No. 529538-B, Calbiochem-Novobiochem, UK). Monoclonal antibodies against actin and against the green fluorescence proteins (GFP) were obtained from Santa Cruz Biotechnology (USA). Polyclonal antibodies against HK were kindly provided by Dr. John E. Wilson (University of Michigan, Ann Arbor, Mich.). Horseradish peroxidase (HRP)-conjugated goat anti-rabbit antibodies were obtained from Zymed (USA). HRP-conjugated anti-mouse antibodies were obtained from Promega (USA).

Plasmids and Site-Directed Mutagenesis mVDAC1 (mouse VDAC1) cDNAs (obtained from W. J. Craigen, University of Houston, Tex.) were subcloned into plasmid pEGFP-N1 (Clontech) for construction of the VDAC1-GFP or VDAC1 expressing mammalian vector with a neomycin resistant gene serving as marker. Rat muscle VDAC1 cDNA was cloned and sequenced (Shoshan-Barmatz, V. and Ashley R., unpublished). Site-directed mutagenesis of mVDAC1 was carried out in vitro by overlapping PCR amplification. Recombinant plasmid pSEYC58, carrying wild type mVDAC1 gene, served as the template for amplification of the VDAC1 variant genes. The variant mVDAC1 genes were constructed using the T7 and T3 universal primers, together with the primers shown in table 1 to introduce the various point mutations.

Cell Types

The U937 human monocytic cell line was grown under an atmosphere of 95% air and 5% $CO_2$ in RPMI 1640 supplemented with 10% fetal calf serum (FCS), 1 mM L-glutamine, 100 U/ml penicillin, and 100 μg/ml streptomycin.

T-REx-293 cells: A transformed primary human embryonal kidney cell line (Invitrogen) was grown under an atmosphere of 95% air and 5% $CO_2$ in DMEM supplemented with 10% fetal calf serum (FCS), 2 mM L-glutamine, 1000 U/ml penicillin, 1 mg/ml streptomycin and 5 μg/ml blasticidin. Other cell lines used were stably transfected derivatives of T-REx-293 that express the tetracycline repressor. hVDAC1-shRNA T-REx-293 cells: T-REx-293 cells, stably transfected with the pSUPERretro plasmid encoding shRNA targeting hVDAC1 were grown with 0.5 μg/ml puromycin and 5 μg/ml blasticidin. The pc-mVDAC1-hVDAC1-shRNA T-REx-293 cells: hVDAC1-shRNA-T-REx-293 cells were transfected with plasmid mVDAC1- or E72Q-mVDAC1-pcDNA4/TO, expressing mVDAC1 or E72Q-mVDAC1 under the tetracycline control. Cells were grown with 200 μg/ml zeocin, 0.5 μg/ml puromycin and 5 μg/ml blasticidin.

All constructs were confirmed by sequencing. The VDAC1 polypeptide variant sequences are denoted herein as follows: E72Q: SEQ ID NO:43; E87Q D88N: SEQ ID NO:44; E65Q: SEQ ID NO:45; K73L: SEQ ID NO:46; D77N: SEQ ID NO:47; E202Q: SEQ ID NO:48; N75A: SEQ ID NO:49; G67A: SEQ ID NO:50. The corresponding nucleotide sequences are denoted herein SEQ ID NO:51-SEQ ID NO:58, respectively.

TABLE 1

Primers used in synthesizing the VDAC1 variants

| VDAC1 Variant | Primer sequences |
|---|---|
| E72Q-mVDAC1 | Forward 5'-GACGTTTACACAGAAGTGGAAC-3' (SEQ ID NO: 59)<br>Reverse 5'-GTTCCACTTCTGTGTAAACGTC-3' (SEQ ID NO: 60) |
| E65Q-mVDAC1 | Forward 5'-TGGACTCAGTATGGGCTGACG-3' (SEQ ID NO: 61)<br>Reverse 5'-GCCCATACTGAGTCCATCTG-3' (SEQ ID NO: 62) |
| K73L-mVDAC1 | Forward 5'-ACAGAGCTGTGGAACACAGAC-3' (SEQ ID NO: 63)<br>Reverse 5'-GTTCCACAGCTCTGTAAACGTC-3' (SEQ ID NO: 64) |
| D77N-mVDAC1 | Forward 5'-GAACACACAGAACACCCTGGG-3' (SEQ ID NO: 65)<br>Reverse 5'-GTGTTCTGTGTGTTCCACTTCTC-3' (SEQ ID NO: 66) |
| E202Q-mVDAC1 | Forward 5'-GAAGTTGCAGACTGCTGTCAATCTC-3' (SEQ ID NO: 67)<br>Reverse 5'-GCGAGATTGACAGCAGTCTGCAAC-3' (SEQ ID NO: 68) |
| N75A-mVDAC1 | Forward 5'-GAACACAGACGCCACCC-3' (SEQ ID NO: 69)<br>Reverse 5'-GTGGCGTCTGTGTTCC-3' (SEQ ID NO: 70) |
| G67A-mVDAC1 | Forward 5'-GATGGACTGAGTATGCCCTGACG-3' (SEQ ID NO: 71)<br>Reverse 5'-GTCAGGGCATACTCAGTCCATCTG-3' (SEQ ID NO: 72) |

Underlined nucleotides introduce the relevant mutation.

Non-transformed cell lines were maintained in a humidified atmosphere, at 37° C. with 5% $CO_2$. CT26, B16, MCF-7, HepG2, HCT116, HeLa, Panc-1 and T-Rex-293 cells were maintained in Dulbecco's modified Eagle's medium (Biological Industries, Beit-Haemek, Israel), supplemented with 10% fetal calf serum, 2 mM L-glutamine, 100 U/ml penicillin, 100 μg/ml streptomycin, 1 mM sodium pyruvate and nonessential amino acids (all from Biological Industries). Molt4 and BCL1 cells were maintained in RPMI-1640 medium (Biological Industries, Beit Haemek, Israel), supplemented with 10% FCS, 2 mM L-glutamine, 100 U/ml penicillin and 100 μg/ml streptomycin.

Mitochondrial Preparation

Mitochondria were isolated rat liver, brain (Johnson and Lardy 1967) or human leukemic U937 cells using published procedures (Bouregeron, et al, 1992).

Protein Determination

Mitochondrial protein content was determined by the Biuret method; hexokinase concentration was determined using the Bradford method with ovalbumin as standard.

$Ca^{2+}$ Accumulation $Ca^{2+}$ uptake by freshly prepared rat liver mitochondria (0.5 mg/ml) was assayed for 1 to 20 minutes at 30° C. in the presence of 225 mM mannitol, 75 mM sucrose, 120 μM $CaCl_2$ (containing $3\times10^4$ cpm/nmol [$^{45}Ca^{2+}$]), 5 mM HEPES/KOH, 5 mM succinate and 0.1 mM Pi, pH 7.0. Uptake of $^{45}Ca^{2+}$ was terminated by rapid Millipore filtration followed by a wash with 5 ml of 150 mM KCl.

Mitochondrial Swelling $Ca^{2+}$-induced mitochondria large amplitude swelling was assayed in freshly-prepared mitochondria under the same conditions as for $Ca^{2+}$ accumulation, except that the temperature was 24° C. Cyclosporine A (CsA)-sensitive mitochondrial swelling was initiated upon addition of $Ca^{2+}$ (0.2 mM) to the sample. Absorbance changes at 520 nm were monitored every 15-20 sec with an Ultraspec 2100 spectrophotometer.

Release of Cytochrome C

Mitochondria (0.5 mg/ml) were incubated with or without 1 U/ml of HK-I for 20 min in a solution containing 150 mM KCl, 25 mM $NaHCO_3$, 5 mM succinate, 1 mM $MgCl_2$, 3 mM $KH_2PO_4$, 20 mM HEPES, pH 7.4. Swelling was monitored after the addition of 200 μM $Ca^{2+}$. Following complete swelling, the samples were centrifuged and mitochondrial pellets (25 μg) or supernatant (40 μl) were subjected to SDS-PAGE and Western blot analyses using monoclonal anti-cytochrome C antibodies.

Rat Brain HK-I Purification, Activity and Binding to Mitochondria

Rat brain HK-I was purified as described previously (Wilson, J. E., 1989; see also Azoulay-Zohar et al., 2004). HK-I activity was assayed by coupling NADH formation to the production of G-6-P by HK-I and its subsequent oxidation by G-6-PDH in a reaction mixture containing: 4 mM Mg-HEPES, 1 mM K-EDTA, 0.6 mM NAD+, 10 mM glucose, 1 mM ATP, 1 mg/ml BSA, 20 mM K-HEPES, pH 7.8. HK-I binding to mitochondria isolated from the different yeast strains (2 mg/ml) was carried out by a 1 h incubation on ice of the mitochondria with HK-I (0-2 U/ml) in 0.1 ml of a solution containing 420 mM mannitol, 140 mM sucrose, 1 mg/ml BSA, 5 mM Mg-HEPES, pH 7.8. Soluble and mitochondria-bound HK-I-containing fractions were separated and analyzed for HK-I activity (Azoulay-Zohar et al., 2004). HK-I binding was defined as the percent of activity present in the bound fraction relative to the total activities found in the bound and free fractions combined.

Purification of VDAC

Native and mutated mVDAC1 were extracted with lauryldimethylamine N-oxide (LDAO) from mitochondria isolated from yeast expressing various VDACs, and purified by chromatography on hydroxyapatite followed by carboxymethyl (CM)-cellulose where LDAO was replaced by β-OG (β-octylglucoside).

VDAC Channel Recording and Analysis

Reconstitution of purified VDAC into a planar lipid bilayer (PLB) multi-channel current recording and data analyses were carried as follows. Briefly, PLB were prepared from soybean asolactin dissolved in n-decane (50 mg/ml) in a chamber containing 10 mM HEPES/KOH pH 7.4 and 0.5 or 1M NaCl (cis/trans). Only PLBs with a resistance greater than 100 GΩ were used. Purified VDAC (about 1 ng) was added to the chamber defined as the cis side. After one or a few channels inserted into the PLB, excess protein was removed by perfusion of the cis chamber with 20 volumes of a solution (with the same composition as before perfusion), in order to prevent further protein incorporation. Currents were recorded under voltage-clamp mode using a Bilayer Clamp amplifier (Warner Instrument, USA). The currents were measured with respect to the trans side of the membrane (ground). The currents were low-pass filtered at 1 kHz, using a Bessal filter (Frequency Devices, USA) and digitized on-line using a Digidata 1200 interface board and pCLAMP 6 software (Axon Instruments). Sigma Plot 2000 scientific software was used for data analyses. Experiments were performed at 23-25° C.

Gel Electrophoresis and Immunoblot Analyses

SDS-PAGE was performed according to Laemmli. Gels were stained with Coomassie Brilliant blue or electroblotted onto nitrocellulose membranes and immunostained using monoclonal anti-VDAC, anti-GFP, anti-actin or polyclonal anti-HK-I antibodies followed by incubation with HRP-conjugated anti-mouse IgG for anti-VDAC, anti-GFP or anti-actin antibodies, and HRP-conjugated goat anti-rabbit IgG for anti-HK-I as secondary antibodies. Antibody binding was detected using chemiluminescence (Santa Cruz Biotechnology, USA).

Tissue Culture and Cell Transfection

Logarithmically-growing U937 cells were resuspended in RPMI 1640 supplemented with 10% FCS, 100 U/ml penicillin and 100 mg/ml streptomycin at a concentration of $2.5 \times 10^7$ cells/ml. Cells were transfected to express rat or murine VDAC1 using the vectors pEGFP, pEGFP-VDAC1, pEGFP-E72Q-mVDAC1, pE-mVDAC1 or pE-E72Q-mVDAC1. Transfection of the U937 cells was performed by electroporation with a single pulse from a Bio-Rad micropulser II with a capacitance extender unit (200 V, 950 mF). Cells were incubated on ice for 10 min before and after transfection, and then resuspended in 20 ml of RPMI 1640 supplemented with 10% FCS, 1 mM l-glutamine, 100 U/ml penicillin and 100 mg/ml streptomycin. Transfection efficiencies were 68-72%, as assessed by GFP expression. GFP-positive cells were viewed under a microscope using a blue filter.

Other cells were transfected using metafectene. In summary, cells ($3 \times 10^5$) growing at 37° C. in a $CO_2$ incubator were cultured to 30-50% confluence 24 h before transfection. For transfection, two separate solutions were prepared: solution A: 5 μg DNA in 50 μl of serum and antibiotics free DMEM medium; solution B: 2.4 μl metafectene reagent (Biontex, Munich, Del.) in 50 μl serum and antibiotic-free DMEM medium. The two solutions were combined, mixed gently and incubate at room temperature for 20 min (DNA lipid complexes). After incubation, the cells were resuspended in 1 ml of serum and the DMEM medium, followed by addition of the DNA lipid complexes and gentle mixing. After 5 hours, the transfection mixture was replaced with a complete DMEM medium and cells were allowed to grow at 37° C. in a $CO_2$ incubator.

Double-Transfection

U937 cells were transfected with pcDNA3.1-HisA or pcDNA3.1-HisA-HK-I (neomycin resistance; provided by Dr. J. E. Wilson, University of Michigan) by electroporation, and grown in complete RPMI 1640 with neomycin (400 mg/ml). After 12 days, the selected cells were transfected with pEGFP, pEGFP-mVDAC1 or pEGFP-E72Q-mVDAC1 and were grown in the presence of neomycin (400 mg/ml). The viability of double-transfected cells was analyzed during 48 to 76 hr.

Cell Treatment

Cells were plated at a density of $5.4 \times 10^4$ cells/cm$^2$ in 24-well plates, washed once with PBS and placed in serum-free medium. Cells were then incubated with or without RuR or Ru360. Cells were also treated with 1.25 mM staurosporine (STS) to induce apoptosis and analyzed for viability 3, 5 and 7 hrs after STS addition. Treatments with curcumin (120 μM) or $As_2O_3$ (20 μM) were carried out for 48 hrs.

Acridine Orange (AcOr)/Ethidium Bromide (EtBr) Staining of Cells

To determine cell viability, cells were stained with 100 μg/ml acridine orange (AcOr) and 100 μg/ml ethidium bromide (EtBr) in PBS. Cells were centrifuged at 1500×g for 5 min at room temperature and resuspended in 25 μl of complete medium, to which 2 μl of AcOr/EtBr solution were added. The cells were then visualized by fluorescence microscopy (Olympus IX51) and images were recorded on an Olympus DP70 camera, using a SWB filter.

Patients

Blood samples were provided from the Institute of Hematology, Soroka University Medical Center. Beer Sheva, Israel. Blood samples were taken from 40 CLL patients.

Data relevant to the research, such as stage of disease (I-IV, Rai staging system), white blood count (WBC), age, and gender, of each patient were provided by the Institute of Hematology and are presented in Table 1.

Isolation of PBMCs and Cell Cultures

Peripheral blood mononuclear cells (PBMCs) were isolated from venous blood of patients with chronic lymphocytic leukemia (CLL) by Ficoll-Paque PLUS (GE Healthcare, Israel) density gradient centrifugation. After informed consent, venous blood (10 ml) was drawn from CLL patients satisfying diagnostic criteria for CLL or from normal adult donors. Blood was collected into heparin tubes and diluted 1:1 with balance solution (composed of two stock solutions, A and B, in 1:9 ratio, respectively. Solution A contained: D-glucose 1%, $CaCl_2$ $5 \times 10^{-5}$M, $MgCl_2$ $9.8 \times 10^{-4}$M, KCl $5.4 \times 10^{-3}$M, Tris 0.145M, pH 7.6. Solution B contained NaCl 0.14M. The balance solution was prepared freshly every week. The diluted blood sample was subsequently carefully layered on Ficoll-Paque Plus (10 ml of diluted blood: 15 ml Ficoll) in 50 ml conical tubes. Tubes were centrifuged at 400×g (with minimal acceleration and deceleration) for 40 minutes at 18-20° C. The mononuclear cells fine layer was transferred to a new centrifuge tube. Cells were washed 3 times with balance solution and re-suspended in a culture medium appropriate to the application.

The proportion of cancerous B cells of total PBMCs was determined by analyzing the relative quantity of the CD19/CD5 double positive cells, characteristic of B-CLL cells using flow cytometry, and CD19/CD5 specific antibodies. Fresh PBMCs isolated from CLL patients were used for the different experiments. In addition, PBMCs were maintained up to one week in Dulbecco's modified Eagle's medium (DMEM), supplemented with 10% fetal calf serum, 2 mM L-glutamine, 100 U/ml penicillin, 100 μg/ml streptomycin, 1 mM sodium pyruvate, nonessential amino acids, 10 mM Hepes, 11 μM β-mercaptoethanol (all from Biological Industries, Beit-Haemek, Israel), in a humidified chamber of 95% air and 5% $CO_2$ at 37° C., and were used for the different experiments. Finally, fractions of PBMCs were cryopreserved in liquid nitrogen in 90% FCS, 10% dimethyl sulfoxide (DMSO) at a concentration of $25 \times 10^6$ cells/ml. After thawing, the frozen PBMCs were maintained as described above. No significant difference in the various conducted assays was observed between freshly used cells, tissue culture maintained cells, or frozen cells.

Molt4 human T lymphoblastic leukemia cell line was from ATCC (Manassas, Va., USA). Cells were grown in RPMI-1640 medium (Biological Industries) supplemented with 10% FBS, 1 mM L-glutamine, 100 U/ml penicillin, 100 μg/ml streptomycin (all from Biological Industries, Beit-Haemek, Israel). Cells were maintained in a humidified chamber of 95% air and 5% $CO_2$ at 37° C.

Flow-Cytometry Analysis of Cell Death

PBMCs ($2\times10^6$ cells/sample) from CLL patients and healthy donors were treated with various concentrations of the peptide Antp-LP4-trp for 90 minutes. Cells were then gently washed once with PBS and stained with propidium iodide (PI) by adding 2.5 µl (1 mg/ml) and immediately analyzed for cell death. The level of cell death, reflected by the percentage of PI-positive cells, was determined by a flow cytometry analysis.

Apoptosis Assay Using Acridine Orange/Ethidium Bromide Staining of Cells

To determine apoptosis, cells were subjected to staining with 100 µg/ml acridine orange (AcOr) and 100 µg/ml ethidium bromide (EtBr) in PBS. Cells were centrifuged at 1500×g for 5 min at room temperature and resuspended in 25 µl complete medium, to which 2 µl of an AcOr/EtBr solution were added. The cells were then visualized by fluorescence microscopy (Olympus IX51) and images were recorded with an Olympus DP70 camera, using a SWB filter. In each independent experiment, in which early and late apoptotic cells were counted, approximately 250 cells were counted for each treatment.

Cell Viability/Metabolic Activity

Cell viability/metabolic activity was analyzed using an XTT (2,3-bis[2-methoxy-4-nitro-5-sulfophenyl]-2Htetrazolium-5-carboxanilide; tetrazolium salt)-based colorimetric assay that measures the formation of a soluble formazan dye by mitochondrial dehydrogenases. Cells were seeded at a density of 1×105 cells/well onto 96-well culture plates and then left to adhere to the plastic plates overnight before being exposed to the peptide for Ito 6 h. After the treatment, 100 µL XTT solution was added to each well and cells were then incubated for 2-4 h. Dye absorbance was read at 450 nm on a Microplate Reader.

Example 1

Mapping of the Protein-Protein Docking Surfaces in VDAC1

Recently, two domains of VDAC1 that are required for HK-I protection against cell death were identified. Using deletion analysis and site-directed mutagenesis of VDAC1, key contact surfaces on VDAC1 that are essential in its interaction with anti-apoptotic proteins were mapped. VDAC1 mutants were analyzed at the level of purified proteins reconstituted into planar lipid bilayers, isolated mitochondria and in cell culture, where the biological effects of the mutations on induction of apoptosis and protection against apoptosis by HK-I were determined.

Figures 1B, 1C:
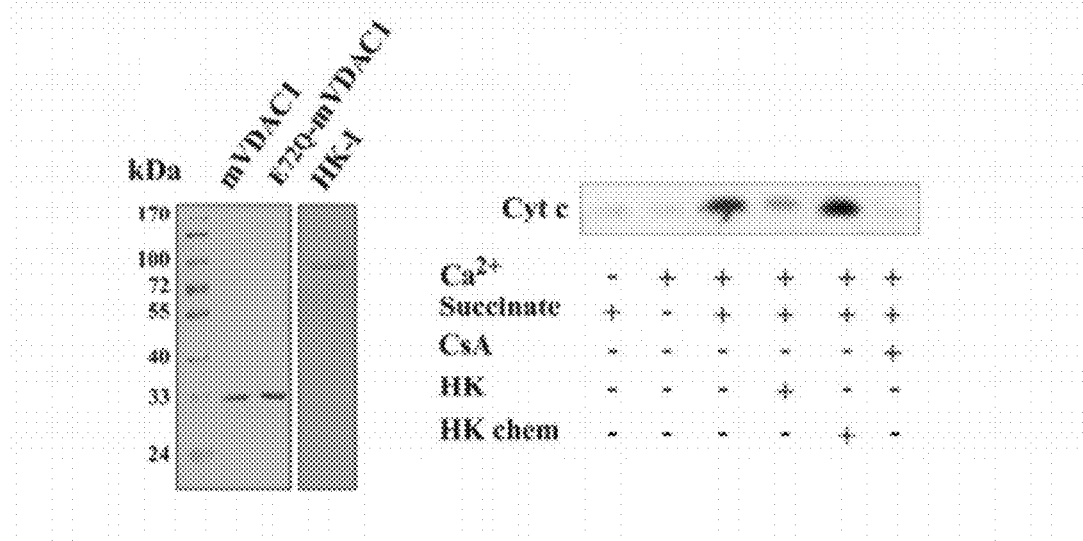
FIG. 1B shows SDS-PAGE of purified VDAC1 and HK-I.
FIG. 1C shows inhibition of cytochrome c release by HK-I.

The results presented herein in FIG. 1 show that HK-I interacts directly with VDAC1 and induces its closure. FIGS. 1A-1C show that HK-I is able to close native VDAC1 but not mutated E72Q-VDAC1 (SEQ ID NO:43). FIG. 1A: Purified recombinant native or E72Q-mutated mVDAC1 was reconstituted into a PLB (planar lipid bilayer) in symmetrical solutions of 0.5 M NaCl. Currents through VDAC1 channel in response to a voltage step from zero to −20 mV were recorded before and 5 min after the addition of HK-I (28.6 mU/ml). The dashed lines indicate the zero-current level. FIG. 1B shows a Coomassie stain of purified VDAC1 (0.2 µg) and HK-I (0.1 µg) used in these studies. FIG. 1C: Cytochrome c release was assayed, using a monoclonal anti-cytochrome c antibody, in the absence or the presence of HK-I (1 U/ml), chymotrypsin-treated HK-I (1 U/ml) or CsA (10 micro M).

Example 2

HK-I Prevents PTP Opening and Release of Cytochrome C

FIG. 2 shows the effects of HK-I on PTP opening, as monitored by $Ca^{2+}$ accumulation and swelling of energized mitochondria, and by release of cytochrome c. HK-I inhibited PTP opening and this inhibition was prevented by an antibody specific to the N-terminal of HK-I (FIG. 2C). The failure of non-binding species of HK, such as yeast HK, or trypsin- or chymotrypsin-treated HK-I (FIG. 2D) to prevent PTP opening, confirmed the specificity of the HK-I effect, and of the requirement of the HK-I N-terminal region for its interaction with VDAC.

Figure 2A:
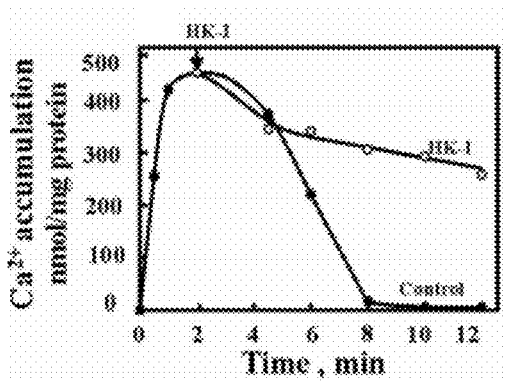
FIGS. 2A-2D shows the effects of HK-I on the permeability transition pore (PTP) opening, as monitored by Ca2+ accumulation (FIG. 2A) and swelling of energized mitochondria (FIG. 2C-2D). HK-I inhibited PTP opening and this inhibition was prevented by an antibody specific to the N-terminal of HK-I (FIG. 2C). The failure of non-binding species of HK, such as yeast HK, or chymotrypsin-treated HK-I (FIG. 2D) to prevent PTP opening, confirmed the specificity of the HK-I effect, and of the requirement of the HK-I N-terminal region for its interaction with VDAC.
Figure 2B:
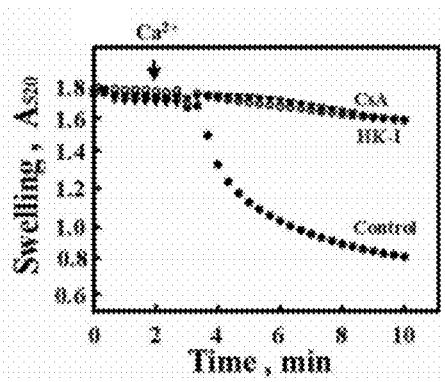
Figure 2C:
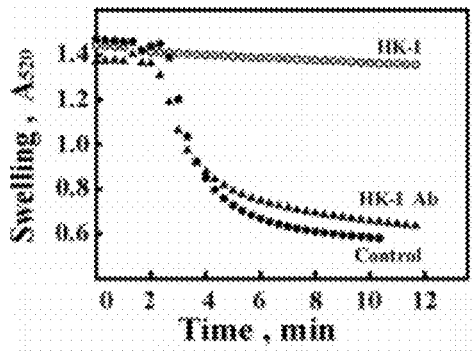
Figure 2D:
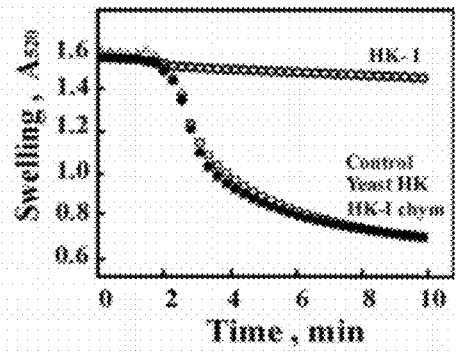

HK-I prevented the release of cytochrome c from mitochondria (as revealed by Western blot analysis, FIG. 1C). The effects of HK-I are similar to those of the well-known inhibitor of PTP, cyclosporine A (CsA) (FIGS. 1C and 2B).

Example 3

HK-I Over-Expression Protects Against Apoptotic Cell Death Induced by Over-Expression of Native and Some VDAC1 Variants, but not of E72Q- and E65Q-mVDAC1

Leukemic U937 cells were transformed to express green fluorescent protein (GFP) and VDAC1-GFP. While cells expressing GFP showed diffuse green fluorescence, cells expressing VDAC1-GFP showed mainly punctuated fluorescence confined to membranes (FIG. 3A). Immunoblot analysis of cell extracts using anti-VDAC or anti-GFP antibodies confirmed the expression of VDAC1-GFP (FIG. 3B). It is noteworthy that the fused VDAC1-GFP was highly protease-sensitive and was readily cleaved to VDAC1 and GFP, as reflected in the appearance of GFP in the VDAC1-GFP expressing cells (FIG. 3B). As shown, in cells transfected to stably over-express HK-I, with and without a second transfection with mVDAC1-GFP or E72Q-mVDAC1-GFP, the level of HK-I was about 3-4-fold higher than in HK-I non-transfected cells The effect of HK-I over-expression on apoptotic cell death of the GFP-tagged version of native and E72Q-mVDAC1 over-expressing cells was examined. Cells were first transformed to over-express HK-I and then transfected with native mVDAC1-GFP or E72Q-mVDAC1-GFP. Apoptotic cell death induced by native mVDAC1 over-expression was dramatically reduced in the cells over-expressing HK-I to a low level of apoptosis (<10%), equal to the control (FIGS. 3C and 3D).

The E72 amino acid is not conserved in the yeast VDAC1, known for its low ability to bind HK-I. Comparison of the amino acid sequence in the structural cytosolic β-loop 2 domain, which includes the E72 amino acid residue in human or murine VDAC1 with that of VDAC1 from *Saccharomyces cerevisiae*, or *Neurospora crassa* reveals that in addition to E72, the charged amino acids D77, K73, and E65 are not conserved. To verify these residues' function in HK-I binding, they were replaced by N, L, and Q, respectively, using overlapping PCR.

Since VDAC1 overexpression induces cell death, U937 cells (FIG. 4A, 4B) or T-Rex™ 293 human embryonic kidney cells (FIG. 4B) were first transformed to stably over-express HK-I and then transfected with native, E65Q, E72Q, K73L, D77N, N75A, or G67A mutated mVDAC1-GFP. Apoptotic cell death induced by native mVDAC1 and by VDAC1 mutated at non-charged amino acids N75A or G67A mutated-mVDAC1 over-expression was dramatically reduced in the cells over-expressing HK-I (FIG. 4B). On the other hand, as obtained with E72Q-expressing cells, no protective effect of HK-I against cell death was obtained in cells over-expressing E65Q-, K73L-, D77N- or E202Q-mVDAC1 variants (FIG. 4). These results suggest that HK-I interaction with VDAC1 involves charged amino acids in the cytosolic β-loop domain in which the E72 residue is located. This β-loop includes amino acid residues T64 to about N78. FIG. 3E shows that HK-I protects against apoptosis induced by STS.

Example 4

Ectopic Expression of VDAC1 Induces Apoptosis

Expression of exogenous murine or rat VDAC1 or VDAC1-GFP, E72Q- or other mutated mVDAC1 variants in various cell lines resulted in cell death characterized by nuclear fragmentation. About 70 to 85% of the cells had died 70 to 78 hrs following cell transfection (FIGS. 3-5; Tables 2-4 herein below; Zaid et al, 2005). Similar results were obtained upon transfection of Jurkat cells with rice or human VDAC (Godbole et al, 2003). These results indicate that the cellular expression level of VDAC may play a crucial factor in the process of mitochondria-mediated apoptosis.

The mechanism by which enhanced VDAC1 expression leads to cell death is not known. Without wishing to be bound to theory, it is possible that a transient increase in the VDAC1 levels produce a significant increase in the leak of the outer mitochondrial membranes and this, in turn, decreases cell viability. This suggestion is in line with the finding that expression of exogenous VDAC1 could only be observed upon exposure of the native but not VDAC1 variant transfected cells to RuR, a treatment that protects against cell death. (FIG. 5D). It thus seems that it is not an increase in the total amount of VDAC1, but rather an increase in its functionality that is responsible for the apoptotic cell death. Similarly, cells over-expressing HK-I, which interact with VDAC1 and inhibit cytochrome c release, were resistant to VDAC1 exogenous expression induced cell death (FIGS. 3 and 4).

Recently, we have shown that dynamic VDAC oligomerization is involved in the release of cytochrome c from mitochondria and suggested that cytochrome c may cross the outer mitochondrial membrane via the large flexible pore formed between individual subunits of a VDAC1 tetramer (Zalk, et al., 2005). Without wishing to be bound to theory, VDAC1 over-expression may encourage VDAC1 oligomerization and thus allow release of pro-apoptotic proteins, such as cytochrome c, from the mitochondrial intermembrane space. The apoptosis-inducing effect of the reagent $As_2O_3$, was recently attributed to an induction of homodimerization of VDAC molecules (Zheng, et al, 2004). This effect could be prevented by over-expression of the anti-apoptotic protein Bcl-xL.

FIG. 6 shows the transmembrane topology of the VDAC1 protein according to the 13 transmembrane β-strand model (modified from Colombini, M., 2004). Proposed cytoplasmic domains of VDAC1, as well as the mutated amino acids are shown schematically. The gray sequences are the proposed peptides for involvement in protein-protein interactions. Mutation of the circled amino acids E65, E72, K73, D77, E202 eliminates HK-I binding to VDAC and HK-I protection against cell death (FIGS. 3 and 4).

Example 5

RuR Protects Against Apoptotic Cell Death Induced by Over-Expression of Native, but not of Mutated mVDAC To further investigate the relationship between the protective effect of RuR and its interaction with VDAC1, leukemic U937 cells were transfected with a plasmid encoding native, E65Q, E72Q, K73L, or D77N-mVDAC1 variant. Fifty six (56) hr after transfection, cells were exposed for 20 hr to RuR (1 μM) and cell viability was analyzed using acridine orange/ethidium bromide staining. In each independent experiment, approximately 250 cells were counted for each including early and late apoptotic cells. Data shown in FIG. 5 and Table 2 are the mean±SEM (n=3). Cells transfected with native, or mutated mVDAC1 or mVDAC1-GFP, to induce over-expression, resulted in increased apoptotic cell death (70-75%), as characterized by enhanced nuclear fragmentation indicative of apoptotic cell death (FIG. 5A). In contrast, control or GFP-transfected cells showed about 14-16% nuclear fragmentation (FIGS. 5B and 5C). Pre-incubation of cells transfected to induce over-expression of VDAC1 or VDAC1-GFP with 1 μM RuR for 18 hr or with 5 μM RuR for 5 hr dramatically reduced their apoptotic cell death (64-72% protection). RuR had no effect or even slightly increased apoptotic death in control or plasmid-transfected cells (FIGS. 5B and 5C).

Strikingly, the protective effect of RuR on recombinant VDAC1 over-expression-induced cell death was not observed in cells expressing E72Q-mVDAC1, E72Q-mVDAC1-GFP or E65Q-mVDAC1 (FIGS. 5B and 5C). Given the RuR-insensitive behavior of E72Q-mVDAC1, as reflected by the inability of RuR to inhibit channel activity in this mutant (FIG. 5E), it appears that RuR protection against apoptosis is exerted through its direct interaction with VDAC. Moreover, the increase (over 5-fold) in the total level of VDAC1 protein in the transfected cells was observed only upon exposure of cells expressing native mVDAC1 to RuR, but not in cells expressing E72Q-mVDAC1 (FIG. 5D).

This indicates that the apoptotic cell death induced by exogenous VDAC1 expression leads to VDAC1 degradation that was prevented upon RuR binding to VDAC1 and protecting against apoptotic cell death.

TABLE 2

| Cells transfected with: | Apoptotic cells, % | | % of protection |
|---|---|---|---|
| | −RuR | +RuR | |
| Control | 6.1 ± 1.0 | 9.1 ± 2.1 | |
| mVDAC-GFP | 69.6 ± 2.7 | 24.7 ± 2.2 | 65 |
| E72Q-mVDAC-GFP | 71.9 ± 4.7 | 71.6 ± 4.4 | 0 |
| E65Q-mVDAC-GFP | 72.7 ± 1.0 | 73.4 ± 0.9 | 0 |
| K73L-mVDAC-GFP | 68.2 ± 3.5 | 37.7 ± 4.1 | 45 |
| D77N-mVDAC-GFP | 69.1 ± 2.7 | 38.7 ± 4.4 | 44 |

Example 6

RuR Induces Channel Closure of Native but not E72Q mVDAC1 Variant

RuR, known to interact with several $Ca^{2+}$ binding proteins and to inhibit $Ca^{2+}$ transport in mitochondria, inhibited channel activity of native but not of E72Q-mutated VDAC1 (FIG. 5E). Purified recombinant native and E72Q-mVDAC1 variant were reconstituted into a planar lipid bilayer (PLB) and the currents produced in response to voltages stepped from a holding potential of 0 mV to −20 mV were recorded. In nine of ten experiments, RuR inhibited recombinant native mVDAC1 channel activity and stabilized the channel in an almost completely closed state. The level of inhibition calculated from five different experiments was 89.2±2.8% (mean±SD, n=9). In contrast, the channel activity of E72Q-mVDAC1 was not inhibited by RuR in all ten experiments.

Example 7

Cell Type Dependent Apoptosis Induction by Various Stimuli, but not by VDAC1 Overexpression Cells were incubated with curcumin (120 μM) or $As_2O_3$ (20 μM) for 48 hrs, or with STS (1.25 μM) for 7 hrs. Cell viability was analyzed by acridine orange/ethidium Bromide staining. In each independent experiment, approximately 250 cells were counted for each treatment, in which early and late apoptotic cells were also counted. The data shown in table 3 is the mean±S.E.M. (n=3).

TABLE 3

Apoptotic cell death, % of control

| Cell type | Control | Curcumin | $As_2O_3$ | STS |
|---|---|---|---|---|
| B-16 | 2.20 ± 0.12 | 37.47 ± 2.20 | 15.0 ± 1.99 | 63.12 ± 0.71 |
| HeLa | 3.40 ± 1.03 | 36.2 ± 0.70 | 24.67 ± 2.65 | 72.37 ± 1.30 |
| Panc | 3.37 ± 0.91 | 70.77 ± 4.31 | 67.20 ± 3.87 | 84.90 ± 2.06 |
| Du-145 | 3.27 ± 0.70 | 8.93 ± 0.47 | 6.0 ± 0.80 | 13.57 ± 4.73 |

In contrast to the cell-type dependent effect of the various apoptosis stimuli (Table 3), Table 4 herein below shows that over-expression of native and E72Q variant mVDAC1 induces apoptotic cell death in all cell lines tested.

The following cell types T-Rex-293 (human embryonic kidney), HeLa (human cervical carcinoma), Panc (human pancreas adenocarcinoma), B-16 (mouse skin melanoma), Du-145 (human prostate carcinoma) and PC-12 (rat adrenal pheochromocytoma) were transfected with native or mutated E72Q mVDAC1 (5 μg) by metafectene reagent. Cell viability was analyzed 76 h after transfection by acridine orange/ethidium bromide staining. In each independent experiment, approximately 250 cells including early and late apoptotic cells were counted.

TABLE 4

% Apoptotic cell death

| Cell type | Control | pEGFP | pEGFP-mVDAC1 | pEGFP-E72Q-mVDAC1 |
|---|---|---|---|---|
| T-Rex-293 | 1.6 | 3.1 | 76.9 | 74.4 |
| HeLa | 2.6 | 2.4 | 81.1 | 75.4 |
| Panc | 2.7 | 2.3 | 84.0 | 84.7 |
| B-16 | 3.6 | 2.9 | 81.0 | 76.1 |
| Du-145 | 2.3 | 2.3 | 87.2 | 83.1 |
| PC-12 | 3.4 | 5.1 | 80.0 | 77.2 |

Example 8

Peptide Synthesis

The following VDAC1 peptides were chemically synthesized:

Peptide N (SEQ ID NO:1) is a 26 amino acid peptide which comprises an amino acid sequence derived from the N-terminal cytosolic segment of VDAC1, the peptide comprising amino acids 1-26 of VDAC1:

MAVPPTYADLGKSARDVFTKGYGFGL;

encoded by Nuc N (SEQ ID NO:6):

5'ATG GCT GTG CCA CCC ACG TAT GCC GAT CTT GGC AAA

TCT GCC AGG GAT GTC TTC ACC AAG GGC TAT GGA TTT

GGC TTA

Peptide LP1 (SEQ ID NO:2) is a 15 amino acid peptide comprising an amino acid sequence derived from the first cytosolic β-loop of VDAC1, the peptide comprising amino acids 63-78:

WTEYGLTFTEKWNTD;

encoded by Nuc LP1 (SEQ ID NO:7).

TGG ACT GAG TAC GGC CTG ACG TTT ACA GAG AAA TGG AAT

ACC GAC AAT

Peptide LP2 (SEQ ID NO:3) is a 20 amino acid peptide comprising an amino acid sequence derived from the second cytosolic β-loop of VDAC1, the peptide comprising amino acids 100-119:

SSFSPNTGKKNAKIKTGYKR;

encoded by Nuc LP2 (SEQ ID NO:8):

TCA TCC TTC TCA CCT AAC ACT GGG AAA AAA AAT GCT AAA

ATC AAG ACA GGG TAC AAG CGG GAG CAC ATT

Peptide LP3 (SEQ ID NO:4) is an 18 amino acid peptide comprising an amino acid sequence derived from an intermembranal sequence of VDAC1, the peptide comprising amino acids 157-174: ETAKSRVTQSNFAVGYKT; encoded by Nuc LP3 (SEQ ID NO:9): GAG ACT GCA AAA TCC CGA GTG ACC CAG AGC AAC TTT GCA GTT GGC TAC AAG ACT. LP3 serves as a negative control.

Peptide LP4 (SEQ ID NO:5) is a 17 amino acid peptide comprising an amino acid sequence of cytosolic β-loop 4 of VDAC1, the peptide comprising amino acids 199-215:

KKLETAVNLAWTAGNSN, encoded by Nuc LP4 (SEQ ID NO:10):

AAG AAG TTG GAG ACC GCT GTC AAT CTT GCC TGG ACA GCA

GGA AAC AGT AAC

The peptides are expressed in pRSET as His6 fusion proteins and are purified using Ni affinity chromatography and, if necessary, HPLC. The effects of these peptides on HK-I binding to isolated mitochondria and on reconstituted VDAC1 channel activity are tested. Similar studies are carried out for Bax, Bcl2, Bcl-xL and tBids to search for peptides that specifically interact with these anti-apoptotic proteins.

FIGS. 8A-8C show an alignment of the human VDAC isoforms to the corresponding mouse and rat sequences, for reference only.

Example 9

VDAC1 Peptide Detaches Bound HK-I from Brain Mitochondria

Five VDAC1 peptides were chemically synthesized (Oligonucleotide and Peptide Synthesis Unit, Weizmann Institute). Rat brain mitochondria, known to possess significant amounts of bound HK-I, were used for testing the effects of the VDAC1 peptide on detachment of bound HK-I. As shown in FIG. 9, VDAC1 loop 1 peptide (LP1), containing the E72, was able to release mitochondrial bound HK-I as its activity increased in the supernatant. The peptide induced the detachment of mitochondria-bound HK-I, suggesting that a dynamic equilibrium between free and mitochondria-bound HK-I exists.

FIGS. 10A-10B shows that peptide LP1 eliminates the HK-I prevention of PTP opening. Mitochondrial swelling was assayed in the absence (control ●) or the presence of HK-I (gray ●) and in presence HK-I pre-incubated with peptide LP1. Mitochondrial swelling was assayed as in FIG. 2 in the absence and the presence of peptide LP1 (0.1 mM or 0.3 mM), brain HK-I (0.25 U/ml) or with HK-I pre-incubated for 10 min with LP1. Dark circles represents control, light circles are HK-I alone; triangles are HK-I and LP1 (0.1 mM), dark squares are HK-I and LP1 (0.3 mM).

Detachment or prevention of HK-1 binding to the mitochondria was also demonstrated by inventors of the present invention for peptide N (SEQ ID NO:1, having the amino acids 1-26 of VDAC1). Furthermore, expression of peptide N in cells overexpressing Bcl2-GFP reversed the anti-apoptotic effect of BCl2 againsr STS-induced apoptosis (Abu Hamad et al., 2009, published after the filing of the present invention).

Example 10

Delivery of VDAC Sequences

Several types of delivery systems are being tested for the delivery of the VDAC1 specific peptides, polypeptides and nucleic acids. These delivery systems include: a) Synthetic cell type-specific cell-penetrating VDAC peptides were generated for delivery to cells; b) Non-viral system-mediated gene delivery for delivery and targeting of vectors encoding VDAC peptides and polypeptides; c) Vesicles for polypeptide, peptide and nucleic acid targeting and delivery to target cells.

Cell-penetrating VDAC peptides: The use of peptides as drugs is limited by the peptides inability to cross the cell membrane. A novel carrier system that originates from membrane shuttling proteins has advantages for targeted delivery compared with standard translocation techniques. This "transport system" is mediated by the so-called CPPs, (Cell Penetrating Peptides), which consist of short peptide sequences that rapidly translocate large molecules into the cell interior in a seemingly energy- and receptor-independent manner. CPPs have low toxicity and a high yield of delivery. Exemplary CPPs are the ANTP domain described herein above, the HIV-1 transcriptional factor TAT (having the amino acid sequence set forth in SEQ ID NO:76), VP22 from HSV-1 and a fragment of the transferrin (Tf) domain (having the amino acid sequence set forth in SEQ ID NO:75) recognised by transferrin receptor which is highly expressed in several cancerous cell types.

Most small peptides are flexible in solution and do not adopt the structure that the same sequence adopts in the native protein. Some of the selected VDAC1 peptides, according to VDAC1 topological model (see FIG. 6), exist in the form of β-loops. Therefore, the peptides were designed to contain the amino acids sequence SWTWE at the N-terminus of the peptide and KWTWK at the C-terminus (together the "Trp zipper amino acids"). These sequences can induce the formation of stable β-hairpins by tryptophan-tryptophan cross-strand pairs (TRP zipper) as demonstrated for peptide LP1 in FIG. 7. The following sequences refer to the TRP zipper and or ANTP domain peptides:

Peptide N-ANTP (SEQ ID NO:11) is a 26 amino acid peptide representing the N-terminal segment of VDAC1, further comprising the ANTP domain at its N-terminus:

MRQIKIWFQNRRMKWKKMAVPPTYADLGKSARDVFTKGYGFGL;

encoded by Nuc N-ANTP as set forth in SEQ ID NO:16:

5'ATGCGTCAGATTAAAATTTGGTTTCAGAATCGTCGTATGAAATGGAAA

AAAATGGCTGTGCCACCCACGTATGCCGATCTTGGCAAATCTGCCAGGGA

TGTCTTCACCAAGGGCTATGGATTTGGCTTATGA;

Alternatively, peptide N-ANTP (SEQ ID NO:73) is a 26 amino acid peptide representing the N-terminal segment of VDAC1, further comprising the ANTP domain at its C-terminus:

MAVPPTYADLGKSARDVFTKGYGFGLMRQIKIWFQNRRMKWKK;

encoded by Nuc N-ANTP as set forth in SEQ ID NO:74:
ATGGCTGTGCCACCCACGTATGC-
CGATCTTGGCAAATCTGCCAGGGATGTCTT CAC-
CAAGGGCTATGGATTTGGCTTAATGCGT-
CAGATTAAAATTTGGTTTCAGAATCG
TCGTATGAAATGGAAAAAA; Peptide LP1-trp (SEQ ID NO:12) is a 42 amino acid peptide comprising an amino acid sequence derived from the first cytosolic loop of VDAC1, amino acids 63-78, further comprising Trp zipper amino acids and the ANTP domain:

MRQIKIWFQNRRMKWKKSWTWEWTEYGLTFTEKWNTDKWTWK;

encoded by Nuc LP1-trp as set forth in SEQ ID NO:17:

5'ATGCGTCAGATTAAAATTTGGTTTCAGAATCGTCGTATGAAATGGAA

AAAATCCTGGACCTGGGAATGGACTGAGTACGGCCTGACGTTTACAGAG

AAATGGAATACCGACAATAAATGGACCTGGAAATGA

Peptide LP2-trp (SEQ ID NO:13) is a 47 amino acid peptide comprising an amino acid sequence derived from the second cytosolic loop of VDAC1, amino acids 100-119, further comprising Trp zipper amino acids and the ANTP domain:

MRQIKIWFQNRRMKWKKSWTWESSFSPNTGKKNAKIKTGYKRKWTWK;

encoded by Nuc LP2-trp as set forth in SEQ ID NO:18):

5'ATGCGTCAGATTAAAATTTGGTTTCAGAATCGTCGTATGAAATGGAAAA

AATCCTGGACCTGGGAATCATCCTTCTCACCTAACACTGGGAAAAAAATG

CTAAAATCAAGACAGGGTACAAGCGGGAGCACATTAAATGGACCTGGAAAT

GA

Peptide LP3-trp (SEQ ID NO:14) is an 45 amino acid peptide comprising an amino acid sequence derived from the inter-membranal β-loop (loop 3) of VDAC1, amino acids 157-174, further comprising Trp zipper amino acids and the ANTP domain:

MRQIKIWFQNRRMKWKKSWTWEETAKSRVTQSNFAVGYKTKWTWK;

encoded by Nuc LP3-trp as set forth in SEQ ID NO:19:

5'ATGCGTCAGATTAAAATTTGGTTTCAGAATCGTCGTATGAAATGGAAA

AAATCCTGGACCTGGGAAGAGACTGCAAAATCCCGAGTGACCCAGAGCAA

CTTTGCAGTTGGCTACAAGACTAAATGGACCTGGAAATGA

Peptide LP4-trp (also designated ANT-LP4-trp or antp-LP4-trp, having SEQ ID NO:15) is a 44 amino acid peptide comprising an amino acid sequence derived from the fourth β-loop (cytosolic) of VDAC1, amino acids 199-215, further comprising Trp zipper amino acids and the ANTP domain:

MRQIKIWFQNRRMKWKKSWTWEKKLETAVNLAWTAGNSNKWTWK, encoded by Nuc LP4-trp as set forth in SEQ ID NO:20:

5'ATGCGTCAGATTAAAATTTGGTTTCAGAATCGTCGTATGAAATGGAAA

AAATCCTGGACCTGGGAAAGAAGTTGGAGACCGCTGTCAATCTTGCCTG

GACAGCAGGAAACAGTAACAAATGGACCTGGAAATGA;

Peptide TAT-LP4-trp (SEQ ID NO:77) is a 37 amino acid peptide comprising an amino acid sequence derived from the fourth β-loop (cytosolic) of VDAC1, amino acids 199-215, further comprising Trp zipper amino acids and the TAT domain:

RKKRRQRRRGG SWTWEKKLETAVNLAWTAGNSNKWTWK

Peptide Tf-LP4-trp (SEQ ID NO:78) is a 33 amino acid peptide comprising an amino acid sequence derived from the fourth β-loop (cytosolic) of VDAC1, amino acids 199-215, further comprising Trp zipper amino acids and the TfR domain:

HAIYPRHSWTWEKKLETAVNLAWTAGNSNKWTWK.

To facilitate the translocation of the peptides across the cell membrane, the sequence peptide was linked to the C or N terminus of the cell penetrating peptide (CPP) derived from the *Drosophila* homeobox protein Antennapedia (Antp). By using available antibodies against Antp, the expression/penetration of the peptide in the cell can be followed.

The peptides N-ANTP (C-terminus), ANTP-LP4-trp, TAT-LP4-trp and Tf-LP4-trp were synthesized by GL Biochem (Shanghai, China). The N-terminal peptide was water-soluble, while the other peptides were dissolved in DMSO. The concentration of DMSO in control and peptide-containing samples was up to 4%.

As shown in Table 5, all examined CPP efficiently introduced the VDAC-1 derived peptides into cancerous cells, enabeling the peptide to exert their pro-apoptotic activity (measured by the peptide concentration required to induce apoptosis in 50% of the celols (IC$_{50}$, μM). The cells examined were peripheral blood mononuclear cells (PMBC) isolated from pateints having chronic lymphocytic leukemia (CLL) and MEC-1 cell lines (human chronic B-cell leukemia).

TABLE 5

Cancer cell death induced by cell-penetrating VDAC-1-based peptides

| | | | IC$_{50}$ μM | |
| --- | --- | --- | --- | --- |
| CPP | Peptide | SEQ ID NO. | CLL | MEC-1 |
| ANTP | LP4-trp | 15 | 0.2-0.25 | 0.-2.0 |
| TAT | LP4-trp | 77 | 3.5-4.0 | 6.0-7.0 |
| Tf | LP4-trp | 78 | 1.5-2.0 | 2.4-3.0 |
| ANTP | Peptide-N | 73 | 3.0-4.0 | 3.0-4.0 |

Figure 7:
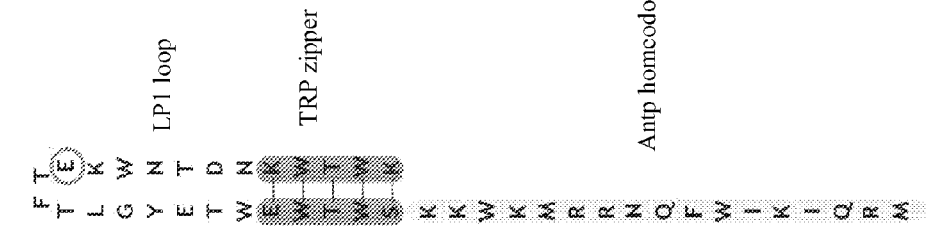
FIG. 7 is a schematic illustration of a peptide comprising amino acid sequences derived from the cytosolic β-loop 1 domain (LP1) peptide (SEQ ID NO:2) comprising the tryptophan zipper sequences (SEQ ID NOS:41 and 42) and an antennapedia homeodomain (SEQ ID NO:39).

Thus, by linking VDAC1 peptide sequences, for example VDAC1 peptide sequences to a CPP, as depicted in FIG. 7, the peptides can be introduced into the cell. Without wishing to be bound to theory, the peptide disrupt the existing VDAC1-HK-I, or HK-II and/or VDAC1-Bcl2 interactions and thereby reduces their anti-apoptotic activity. Control cells and HK-I, HK-II or Bcl2 over-expressing B-16 cells are incubated without and with different concentrations of VDAC1 peptides or ANTP-VDAC1-based peptides, and apoptosis induced by staurosporine and other reagents is monitored. The peptides with the highest activity in preventing the HK-I or Bcl2 anti-apoptotic activity are further tested in cancer cell lines, including prostate, breast, lung, kidney, neuroblastoma, leukemia, glioblastoma cell lines.

Non-Viral Peptide Delivery: Another tool for delivery and targeting VDAC peptides is the use of "shielding particles". The particle surface of these delivery particles can be coated with hydrophilic polymers, e.g. polyethylene glycol (PEG), which prevent binding to, for example, plasma proteins and blood cells and also enable prolonged circulation time in the bloodstream (Oupicky et al., 2002) To provide vectors with the ability to distinguish between target and non-target tissue, cell-binding ligands that recognize target-specific cellular receptors can be added to the particle. Numerous cell-targeting ligands, including peptides, growth factors, antibodies or other proteins, are incorporated into polyplexes (Wagner, et al, 2005) after chemical conjugation to cationic polymers (Schatzlein, 2003). Thus, tailor-made synthetic vectors can be used to achieve targeting to tumor tissue. Therapeutic concepts based, for example, on suicide genes or cytokines, showed encouraging results in preclinical and also in first clinical evaluations. The aim of this proposal is to use a novel targeted gene transfer systems based on DNA/ligand-polycation complexes with tumor targeting ligands to deliver VDAC peptides and derivatives and analogs thereof to cancer cells.

Delivery Vesicles The delivery vesicles are preferably designed to prevent binding of the VDAC1 peptide and derivatives and analogs thereof to plasma proteins or to blood cells and will enable a prolonged circulatory time in the blood stream. To provide vectors with the ability to distinguish between target and non-target tissue, cell-binding ligands that recognize target-specific cellular receptors are introduced. For tumor specific targeting, receptor-targeted polyplexes based on PEI and using transferrin (Tf), epidermal growth factor (EGF) or other ligand for targeting. Depending on the cell type, part of the PEI polymer in the complex is replaced by ligand-PEI conjugate (for example, Tf-PEI or EGF-PEI). All formulations contain PEG-PEI conjugate for shielding purposes.

Example 11

Formulation and Stabilization of Peptide Drugs

Pharmaceutical macromolecules may be damaged during bio-processing and storage; thus, analytical tools are needed for the stage of formulation development and stabilization of peptides. Strategies for solubility optimization, storage, the use of stabilizing agents and stability-indicating assays are developed for the VDAC1 peptides.

Moreover, certain peptides, when introduced to the cell interior, are rapidly degraded, and thus the effect of the peptide might not be as long lasting as desired. To make the peptides more effective drugs, the preparation of peptide analogs, including peptide derivatives and peptidomimetics, having increased stability, including protection against proteolysis, is required. Peptide analogs containing for example N (alpha)-methylamino acids are increasingly recognised as potentially useful therapeutics (Jarver and Langel, 2004).

In addition, the use of an analog of the VDAC effective peptides comprising some or all D-amino acids fused to a D-configured amino acid analog of the Antp are constructed and tested.

Liposomes containing lipid-linked maleinimide is generated by standard loading technique with VDAC1-derived peptides (Derycke and Witte, 2002). Following separation of peptide loaded liposomes from free peptide by size exclusion chromatography, transferrin is modified with hetero-bifunctional cross linker introducing a free thiol group into the transferrin molecule. Covalent coupling to the liposome surface is carried out by reaction of the thiol group with maleinimide residues on the liposome surface.

Example 12

Pro-Apoptotic Activity of VDAC1 Peptide Fragments in Cancer Cells

The effect of VDAC1 peptides in minimizing the self-defense mechanisms of cancer cells, which involve over-expression of anti-apoptotic proteins such as HK-I, are tested in several cancer cell lines, among them recombinant HK-I over-expressing cells. The ability to increase the efficacy of chemotherapeutic drugs by VDAC-based peptides is a step toward developing practical therapies to minimize the self-defense mechanisms of cancer cells involving over-expression of anti-apoptotic proteins such as HK-I.

In a non-limiting example, peptides are introduced into cells by one of at least three ways:

Cells are transfected with mammalian expression vector encoding a VDAC peptide or peptide analog.

VDAC1 polypeptides or peptides fused to penetrating peptides are added to the cells. Alternatively, VDAC1 polypeptide or peptide packed in shield particles containing targeting ligand are added to the cells.

Cell viability and apoptotic cell death of control, HK-I and peptide containing cells is followed by staining cells with acridine orange (AcOr) and ethidium bromide (EtBr) and by Flow Cytometry (FACS) analysis. The expression levels of HK-I, HK-II, Bcl2, Bcl-xL and Bax in these cells are estimated using antibodies specific to each protein. In addition, the level of VDAC peptide in the cells is analyzed using anti-Antp antibodies (anti-HK antibodies from Santa Cruz; anti-VDAC antibodies from Calbiochem; anti-ANTP antibodies from GentTex Inc.)

Example 13

Pro-Apoptotic Activity of VDAC Peptides in Animal Models

Imaging and follow up of synthetic VDAC peptides in vivo by non-invasive measurement of apoptosis and monitoring of glucose metabolism, with positron emission tomography (PET) and $^{18}$-fluorodeoxyglucose, respectively are essential components of a study of this nature. Thus, in vitro and in vivo studies with the most effective VDAC peptides are carried out. Stability of the peptides is evaluated in vivo in this study by utilizing scintographic imaging and HPLC.

First, to evaluate their uptake kinetics, the peptides or peptide analogs are labeled with $^{131}$I and bio-distribution of the labeled peptides is determined in tumor-bearing animals. Complementary animal models are performed including different subcutaneous tumor models, either in immune competent mice (e.g. neuroblastoma in A/J, melanoma in C57/BL6, CT26 in Balb/c) or SCID mice (hepatoma and others).

Example 14

VDAC Peptides Enhance Sensitivity of Cancer Cells to Chemotherapy

The molecular events responsible for chemotherapy resistance of cancer cells remain largely unknown. Pro-survival members of the Bcl-2 family are expressed in many tumors and are associated with the repression of apoptosis induced by chemotherapeutic drugs in vitro. Since the anti-apoptotic Bcl-2 proteins are thought to act via interaction with VDAC, the effect of VDAC-based peptides on Bcl2 over-expressing cells to sensitivity to chemotherapy is studied.

The Bcl-2 protein is produced at high levels in many types of cancer, including about 90% of colorectal, 30-60% of prostate, 70% of breast, 20% of non-small cell lung cancers, and 65% of lymphomas. The in vivo, expression of Bcl-2 has been associated with a poor response to therapy in certain subgroups of cancer patients, including some patients with lymphoma, acute leukemia, and prostate cancer.

Example 15

Pro-Apoptotic Activity of VDAC Peptides in Apoptosis-Defective and Chemotherapy-Resistant Cancer Cell Models To test the effect of the VDAC-based peptides in apoptosis-defective and chemotherapy-resistant cancer cells, an apoptosis-resistance model is used. For example, the non-small cell lung carcinoma (NSCLC) cell lines exhibit an intrinsic resistance to chemo- and radiotherapy, are used to study the mechanisms of apoptosis resistance and to find ways of overcoming this resistance with the VDAC peptides and analogs thereof.

Example 16

Effect of VDAC-1-N-Terminal Peptide
(Peptide-N-ANTP) on Cancer Cells

Figures 11A, 11B:
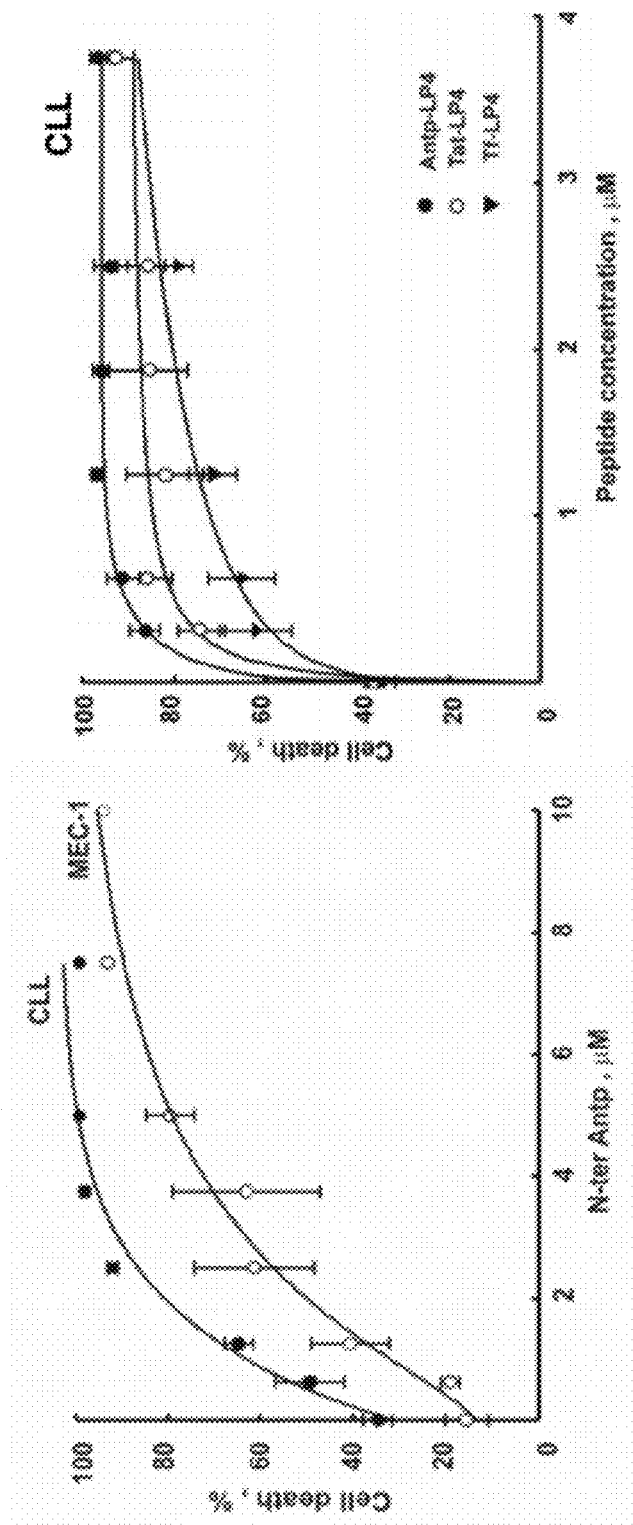
FIG. 11A shows cell death induced by peptide-N linked to the cell penetrating peptide ANTP (the full peptide having SEQ ID NO:73).
FIG. 11B shows cell death induced by ANTP-LP4-trp (SEQ ID NO:15), TAT-LP4-trp (SEQ ID NO:76) and by Tf-LP4-trp (SEQ ID NO:78). Peripheral blood mononuclear cells (PBMCs) isolated from chronic lymphocitic leukeimia (CLL) patient and MEC-1 cell line were treated with the indicated concentreation of the peptide. The level of cell death was determined by FACS analysis.

Preipheral blood mononuclear cells (PMBC) isolated from pateints having chronic lymphocytic leukemia (CLL) and MEC-1 cell lines (human chronic B-cell leukemia) were incubated for 90 min with Peptide N-ANTP (SEQ ID NO:73) at concentrations of 10-40 μM. Cell death was measured by PI staning and FACS analysis. As is shown in FIG. 11, the N-terminal VDAC1 derived peptide induced the death of both cancer cell types.

Figure 12:
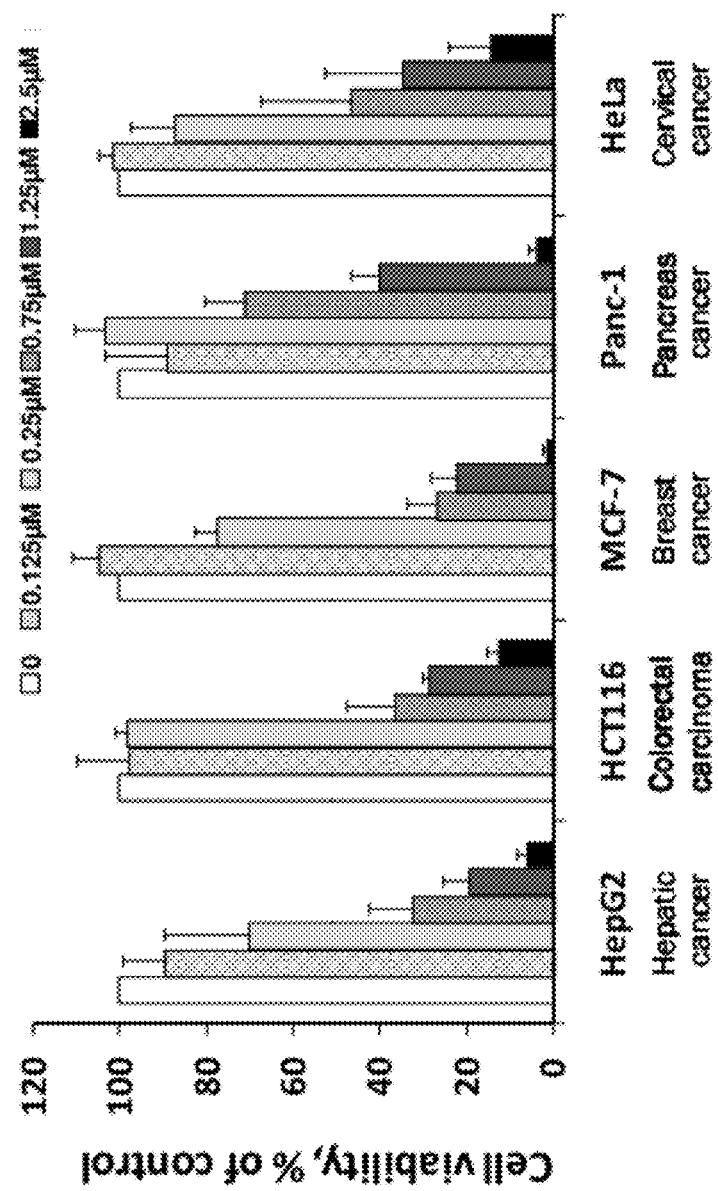
FIG. 12 demonstartes that peptide-N linked to the cell penetrating peptide ANTP (the full pepetide having SEQ ID NO:73) dramatically decreases cell survival in a concentration dependent manner of various cancer cell lines.

The effect of peptide N-ANTP was further examined with a serias of cancer cells including HepG2 cells (hepatic cancer); HCT116 cells (Colorectal carcinoma); MCF-7 (breast cancer), PANC-1 cells (Pancreas cancer) and HeLa cells (cervical cancer). The cells were incubated with the N-terminal-ANTP peptide for 3 h at the concentration range of 0.5-10 μM. Cell vialbility was determinded by XTT (N=3). As is shown in FIG. 12, peptide N-ANTP also dramatically reduced the viability of the examined cancer cells.

Example 17

Effect of Peptide LP4-trp on Cancer Cells

Figure 13:
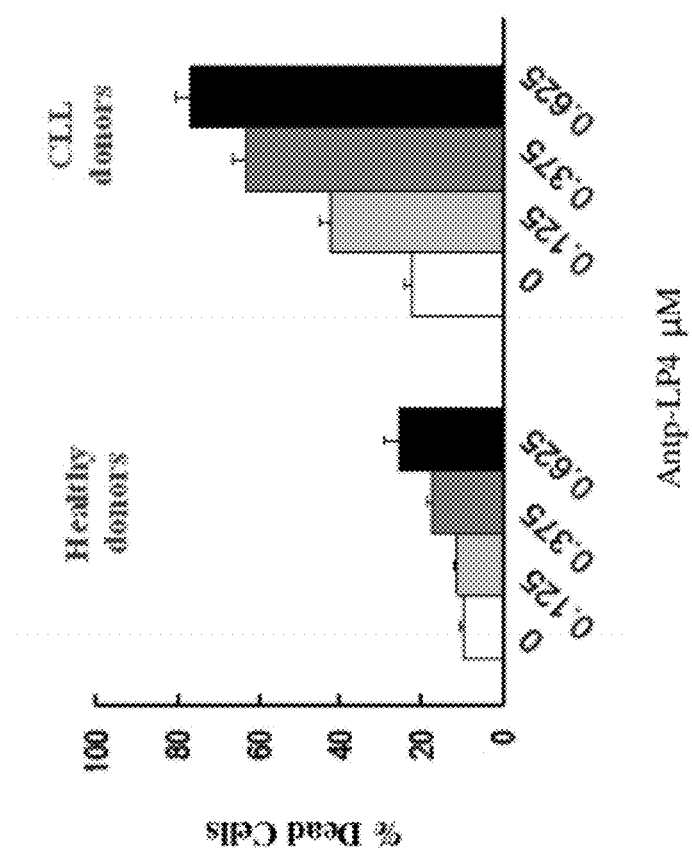
FIG. 13 shows that peptide ANTP-LP4-trp (SEQ ID NO:15) induce dramatic apoptotic cell death in CLL-derived PBMCs. The effect of the peptide on PBMCs isolated from healthy donors was marginal. The peptide cell death induction appears to be specific to CLL cancerous cells as it spared PBMCs isolated from healthy volunteers.

Peptide ANTP-LP4-trp (having SEQ ID NO:15) was also found to be highly effective in inducing cancer cell death (FIG. 13). In ex vivo experiments, peripheral blood mononuclear cells (PBMCs) isolated from healthy individuals or CLL patients were incubated for 90 min with the indicated concentration of the ANTP-LP4-trp peptide. Cell death was assayed by PI staining and FACS analysis (healthy donors, n=34; CLL donors, n=39).

Figures 14A, 14B:
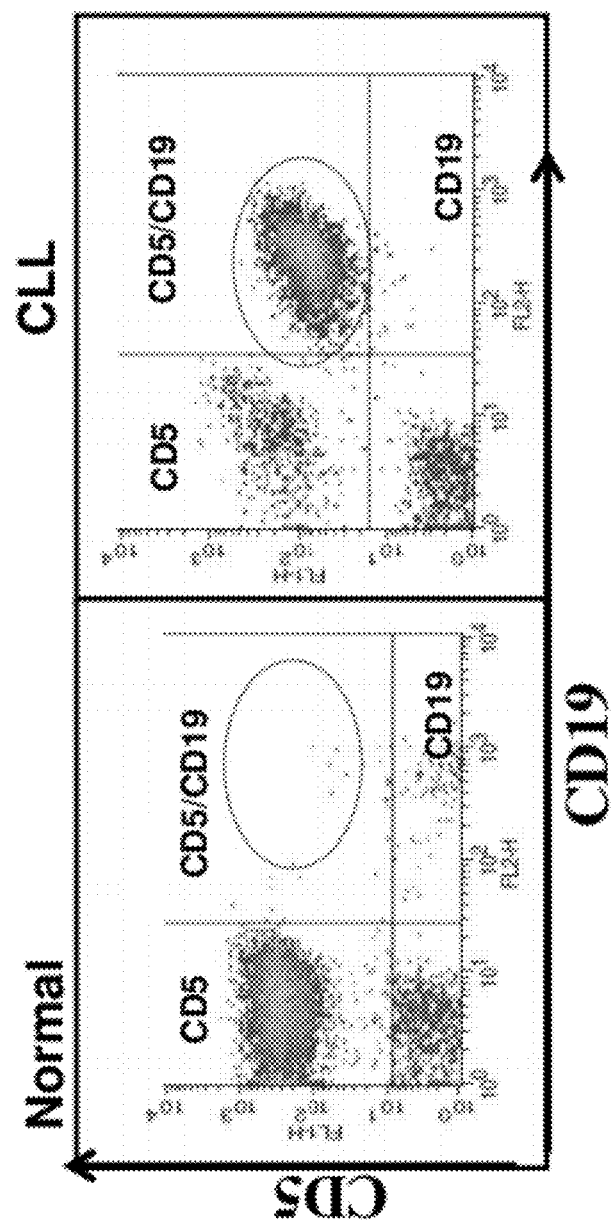
FIG. 14A-B: The percentage of CD19+/CD5+ double positive cells in a healthy donor and CLL patient, respectively, as determined using monoclonal antibodies directed to CD19, a B lymphocyte marker, and CD5, a T lymphocyte marker, followed by FACS analysis.
Figure 14C:
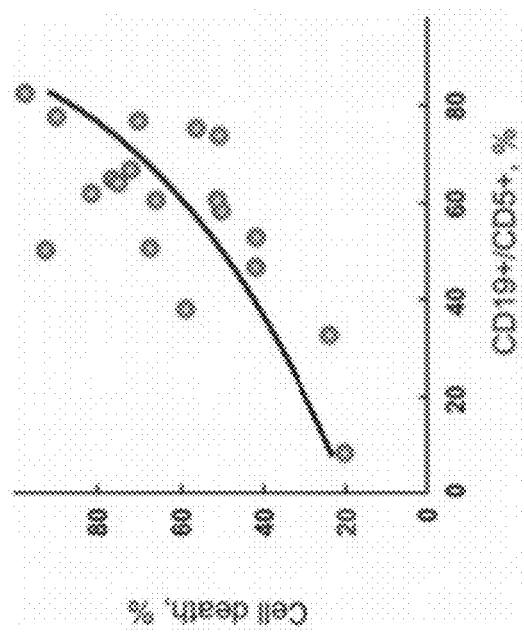
FIG. 14C: correlation between the cell expressing level of CD19 and CD5 (cancer cells) in various patients and the extend of cell death induced by ANTP-LP4.

Furthermore, the activity of this peptide was shown to have specificty to cancer cells. Normal B lymphocytes and cancerous B cells can be differentaited according to the expression of CD19 and CD5: Normal B cells express only the cell surface marker CD5 while the cancerous cells express both CD19 and CD5. As is shown in FIG. 14C, there was a tight correlation between the relative amount of cancer cells and cell death induced by peptide ANTP-LP4-trp (0.375 μM).

Figure 15C:
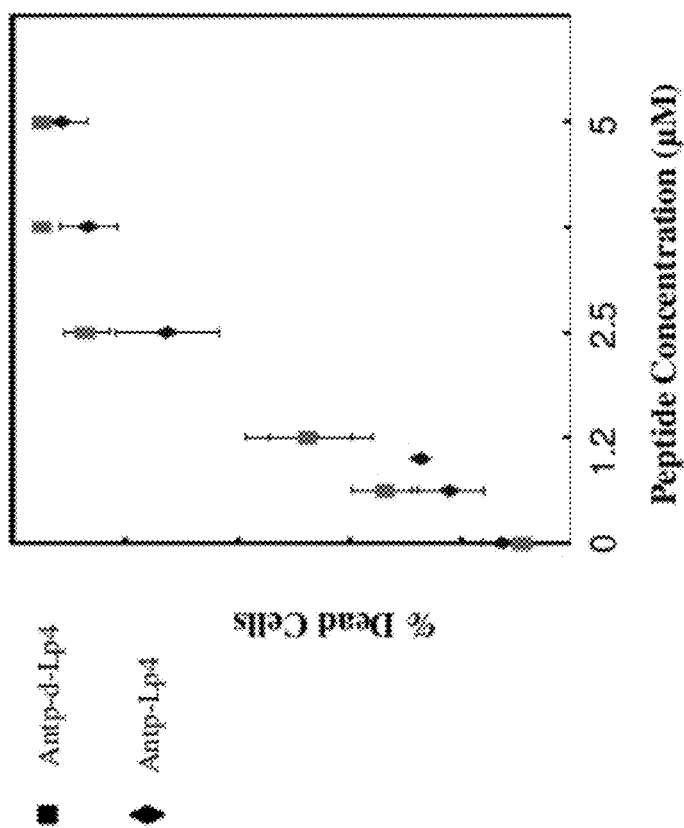
FIG. 15C: MEC-1 cells). The results are average of two experiments

The cell-death induction by ANTP-LP4-trp was irrespective to the D/L configuration of the amino acids composing the synthesized peptide (FIG. 15).

Example 18

Apoptotic Effect of the Peptides N-ANTP and ANTP-LP4-trp on Cancer Cells

The effect of the peptides N-ANTP (having the amino acid sequence of SEQ ID NO:73) and ANTP-LP4-trp (having the amino acid sequence of SEQ ID NO:15) on apoptotic cell death was examined with cancer cells of various trypes. Table 6 below summarizes the cell line examined and concentration of each pepetide that gave 50% apoptotic cell death ($IC_{50}$, μM).

All cells were grown in DMEM accept PC3, D-U145, Molt-4, Jurkat, Mec-1, U937 grown in RPMI medium and HUH7 grown in F12/DMEM medium.

The results show that VDAC1-based peptides efficiently induce cell death with $IC_{50}$ of submicromollar concentration, even in cells resistant to chemotherapy or expressing mutated P53. The most sensitive cells found are from hematological malignancies and prostate cancer cell line. Pancreatic cancer and non-cancerous cell lines were found ro be the most resistant to peptide-induced cell death. Our study shows a promising therapeutic strategy to effectively kill cancer cells and overcome drug resistance, since the peptides effectively kill drug-resistant and P53 mutant cells that usually lead to untreatable tumors.

TABLE 6

Apoptosis induction by the peptides N-ANTP and Antp-LP4-trp

| Cell line | Origin | Mutation status | N-ANTP $IC_{50}$, μM | Antp-LP4-trp $IC_{50}$, μM |
|---|---|---|---|---|
| K562 | Myelogenous leukemia | P53-null | 0.60 ± 0.4 | 0.26 ± 0.1 |
| U937 | Histiocytic lymphoma | Mut-p53 | 0.58 ± 0.2 | 0.28 ± 0.1 |
| JURKAT | Acute T-cell leukemia | Mut-p53 | 0.35 ± 0.5 | 0.23 ± 0.1 |
| MOLT-4 | Acute lymphoblastic leukemia | P53-null | 1.10 ± 0.3 | 0.76 ± 0.2 |
| Mec-1 | B-chronic lymphocytic leukemia | Bcl-xL ↑ | 0.93 ± 0.1 | 0.53 ± 0.1 |
| THP-1 | Acute monocytic leukemia | Mut-P53 | 0.53 ± 0.03 | 0.30 ± 0.1 |
| MDA-MB-231 | Breast adenocarcinoma | Mut-p53, ER null | 1.50 ± 0.3 | 1.60 ± 0.6 |
| MCF7 | Breast adenocarcinoma | Wt-p53, ER↑ mut-caspase 3 | 2.50 ± 0.6 | 1.90 ± 0.04 |
| HUH7 | Hepatocellular carcinoma | Mut-P53 | 1.30 ± 0.3 | 0.60 ± 0.3 |
| Hep-G2 | Hepatocellular carcinoma | Mut-β-catenin | 3.60 ± 1.3 | 1.60 ± 0.6 |
| A549 | Alveolar adenocarcinoma | Bax ↓Mut: CDS, KRAS | 2.70 ± 0.5 | 1.50 ± 0.2 |
| H358 | Bronchoalveolar carcinoma | P53-null | 2.70 ± 0.2 | 1.50 ± 0.5 |
| Panc-1 | Pancreatic carcinoma | Mut: P53, KRAS, p16 | 6.20 ± 0.6 | 6.40 ± 0.6 |
| AsPC1 | Pancreatic adenocarcinoma | Mut: P53, KRAS, p16 | 6.10 ± 0.1 | 2.70 ± 1.7 |
| T3M4 | Pancreatic adenocarcinoma | Mut: P53, p16 | 1.30 ± 0.4 | 0.50 ± 0.2 |
| U87 | Human Glioblastoma | Mut-p53 | 1.40 ± 0.6 | 1.40 ± 0.5 |
| HeLa | Cervix adenocarcinoma | P53-null | 2.70 ± 0.8 | 0.90 ± 0.03 |
| SKOV-3 | Ovarian adenocarcinoma | Mut: BRAF, KRAS | 2.00 ± 0.8 | 1.00 ± 0.2 |
| A375 | Amelanotic melanoma | Mut-BRAF- | 2.80 ± 0.4 | 6.40 ± 0.6 |
| PC-3 | Prostate adenocarcinoma | Mut-P53, Androg↑ | 0.40 ± 0.1 | 1.10 ± 0.3 |
| T-Rex | Embryonic kidney fibroblasts | Non malignant | 5.60 ± 0.9 | 6.50 ± 0.9 |
| PBMCs | Blood | Healthy cells | 10.10 ± 1.2 | |

The foregoing description of the specific embodiments will so fully reveal the general nature of the invention that others can, by applying current knowledge, readily modify and/or adapt for various applications such specific embodiments

REFERENCES

Abu-Hamad S., Arbel N., Cabo D., Arzoine L., Israelson A., Keinan N., Ben-Romano R., Friedman O and Shoshan-Barmatz V. (2009) J Cell Science 122: 1906-1916.

Ausubel, et al (Eds), *Current Protocols in Molecular Biology*, John Wiley & Sons, Inc. (New York) (1987-1999)

Azoulay-Zohar, H., Israelson, A., Abu-Hamad, S. and Shoshan-Barmatz, V. (2004) In self-defense: hexokinase promotes voltage-dependent anion channel closure and prevents mitochondria-mediated apoptotic cell death. Biochem. J. 377: 347-355.

Blachly-Dyson E, Zambronicz E B, Yu W H, Adams V, McCabe E R, Adelman J, Colombini M, Forte M. 1993. Cloning and functional expression in yeast of two human isoforms of the outer mitochondrial membrane channel, the voltage-dependent anion channel. J Biol Chem. 268(3): 1835-41.

Colombini, M. (2004) VDAC: The channel at the interface between mitochondria and the cytosol. Molecular and Cellular Biochemistry 256/257, 107-115.

Cochran, A G, Skelton, N J and Starovasnik, M A. (2001). Tryptophan zippers: Stable, monomeric-hairpins. PNAS, 98:10 pp 5578-5583.

Derycke, A S and Witte P A, (2002) "Liposomes for photodynamic therapy" Int. J. Oncology, 20, pp 181-187

Gennaro (ed.), *Remington's Pharmaceutical Sciences*, 18$^{th}$ Ed. (Mack Publishing Co., 1990)

Godbole A, Varghese J, Sarin A and Mathew MK. (2003) VDAC is a conserved element of death pathways in plant and animal systems. Biochim. Biophys. Acta. 1642: 87-96.

Jarver, P. and Langel, U. (2004) The use of cell-penetrating peptides as a tool for gene regulation. Drug Discov Today 9, 395-402.

Johnson, D. and Lardy, H. (1967) Rat liver mitochondria preparation. Meth. Enzymol., 94-96

Kim R. (2005) Unknotting the roles of Bcl-2 and Bcl-xL in cell death. Biochem Biophys Res Commun. 333(2):336-43.

Li L, Thomas R M, Suzuki H, De Brabander J K, Wang X, Harran P G. (2004). A small molecule Smac mimic potentiates TRAIL- and TNF alpha-mediated cell death. Science. 305(5689):1471-4.

Meienhofer, J (1973). "Hormonal Proteins and Peptides," vol. 2, p. 46, Academic Press (New York).

Mendoza, F J, Espino, P S, Cann, K L, Brisrow, N, McCrea, K. and Los, M. (2005) "Anti-tumor chemotherapy utilizing peptide based approaches-apoptotic pathways, kinases and proteasome targets". Arch Immunol Ther Exp 53:47-60.

Oupicky D., Ogris M. and Seymour L. W. (2002) Development of long-circulating polyelectrolyte complexes for systemic delivery of genes. J Drug Target. 10: 93-98

Pillai O, Panchagnula R. (2001) Polymers in drug delivery. Curr. Opin. Chem. Biol. 5, 447-51, Sambrook, J, Fritsch, E. F. and Maniatis, T. (1989) Molecular Cloning: A laboratory manual, Cold Spring Harbor Laboratory Press, Cold Spring Harbor, USA.

Sapra, P and Allen T M (2004) "Improved outcome when B-cell lymphoma is treated with combinations of immunoliposomal anticancer drugs targeted to both the CD19 and CD20 epitopes." Clin Cancer Res. 10(7):2530-7).

Schatzlein A G. (2003) Targeting of Synthetic Gene Delivery Systems. J Biomed Biotechnol. 2003, 149-158

Schroder, G. and Lupke, K. (1965). The Peptides, vol. 1, Academic Press (New York).

Shoshan-Barmatz, V and Gincel D. (2003) The voltage-dependent anion channel: characterization, modulation, and role in mitochondrial function in cell life and death. Cell Biochem. Biophys. 39: 279-292.

Stewart, J. M. and Young, J. D. (1963), "Solid Phase Peptide Synthesis," W.H. Freeman Co. (San Francisco).

Tracy, M A. (1998) Development and scale-up of a microsphere protein delivery system. Biotechnol. Prog. 14, 108.

Wagner E, Culmsee C, Boeckle S, (2005). "Targeting of Polyplexes: Toward Synthetic Virus Vector Systems" Adv Genet. 53PA:333-354.

Walensky L D, Kung A L, Escher I, Malia T J, Barbuto S, Wright R D, Wagner G, Verdine G L, Korsmeyer S J. Activation of apoptosis in vivo by a hydrocarbon-stapled BH3 helix. (2004). Science. 305(5689):1466-70.

Wilson, J. E. (1989). Rapid purification of mitochondrial hexokinase from rat brain by a single affinity chromatography step on Affi-Gel blue. *Prep Biochem* 19, 13-21.

Zabala M, Wang L, Hernandez-Alcoceba R, Hillen W, Qian C, Prieto J, Kramer M G. (2004), Optimization of the Tet-on system to regulate interleukin 12 expression in the liver for the treatment of hepatic tumors. Cancer Res. 64(8):2799-804.

Zalk R, Israelson A, Garty E, Azoulay-Zohar H and Shoshan-Barmatz V. (2005). Oligomeric states of the voltage-dependent anion channel and cytochrome c release from mitochondria. Biochem. J. Biochem J 386, 73-83.

Zheng Y, Shi Y, Tian C, Jiang C, Jin H, Chen J, Almasan A, Tang H and Chen Q. (2004) Essential role of the voltage-dependent anion channel (VDAC) in mitochondrial permeability transition pore opening and cytochrome c release induced by arsenic trioxide. Oncogene 23: 1239-1247.

Zaid, H., Abu-Hamad, S., Israelson, A., Nathan, I. and Shoshan-Barmatz, V. (2005) Cell Death Differ 12, 751-6.

Citation of any document herein is not intended as an admission that such document is pertinent prior art, or considered material to the patentability of any claim of the present application.

The invention claimed is:

1. An isolated voltage-dependent anion channel 1 (VDAC1) derived peptide capable of inducing apoptosis in a cell, said peptide comprising up to 70 amino acids and comprising an amino acid sequence selected from the group consisting of SEQ ID NO:1, SEQ ID NO:2, and SEQ ID NO:3.

2. The isolated VDAC1 derived peptide according to claim 1, said peptide comprising the amino acid sequence set forth in SEQ ID NO:1.

3. The isolated VDAC1 derived peptide according to claim 1, said peptide is flanked by tryptophan zipper amino acids.

4. The isolated VDAC 1 derived peptide according to claim 1, said peptide further comprises a cell penetrating peptide.

5. The isolated VDAC1 derived peptide according to claim 4, said peptide comprising an amino acid sequence selected from the group consisting of SEQ ID NO:11, SEQ ID NO:12, SEQ ID NO:13 and SEQ ID NO:73.

6. The isolated VDAC1 derived peptide according to claim 5, said peptide comprises the amino acid sequence set forth in SEQ ID NO:73.

7. A pharmaceutical composition comprising a pharmaceutically acceptable carrier or excipient and at least one isolated voltage-dependent anion channel 1 (VDAC1) derived peptide capable of inducing apoptosis in a cell, wherein the isolated VDAC1 derived peptide comprises up to 70 amino acids and comprises an amino acid sequence selected from the group consisting of SEQ ID NO:1, SEQ ID NO:2, SEQ ID NO:3, SEQ ID NO:11, SEQ ID NO:12, SEQ ID NO:13 and SEQ ID NO:73.

8. The pharmaceutical composition according to claim 7, comprising the isolated peptide having the amino acid sequence set forth in SEQ ID NO:1.

9. The pharmaceutical composition according to claim 7, comprising the isolated peptide having the amino acid sequence set forth in SEQ ID NO:73.

10. A method of treating a subject suffering from a lymphoproliferative disease associated with aberrant apoptosis comprising administering to the subject a pharmaceutical composition according to claim 7.

11. A method of inducing cancer cell death comprising applying to the cancer cells at least one isolated voltage-dependent anion channel 1 (VDAC1) derived peptide capable of inducing apoptosis in said cell, wherein the isolated VDAC1 derived peptide comprises up to 70 amino acids and comprises an amino acid sequence selected from the group consisting of SEQ ID NO:1, SEQ ID NO:2, SEQ ID NO:3, SEQ ID NO:5, SEQ ID NO:11, SEQ ID NO:12, SEQ ID NO:13, SEQ ID NO:15 and SEQ ID NO:73.

* * * * *